US009700485B2

(12) United States Patent
Weeks et al.

(10) Patent No.: US 9,700,485 B2
(45) Date of Patent: *Jul. 11, 2017

(54) DELAMINATION RESISTANT PHARMACEUTICAL GLASS CONTAINERS CONTAINING ACTIVE PHARMACEUTICAL INGREDIENTS

(71) Applicant: Corning Incorporated, Corning, NY (US)

(72) Inventors: Wendell P. Weeks, Corning, NY (US); Robert Anthony Schaut, Painted Post, NY (US); Steven Edward DeMartino, Painted Post, NY (US); John Stephen Peanasky, Big Flats, NY (US)

(73) Assignee: Corning Incorporated, Corning, NY (US)

( * ) Notice: Subject to any disclaimer, the term of this patent is extended or adjusted under 35 U.S.C. 154(b) by 86 days.

This patent is subject to a terminal disclaimer.

(21) Appl. No.: 14/259,259

(22) Filed: Apr. 23, 2014

(65) Prior Publication Data
US 2014/0341888 A1 Nov. 20, 2014

Related U.S. Application Data

(60) Provisional application No. 61/815,704, filed on Apr. 24, 2013.

(51) Int. Cl.
A61K 39/395 (2006.01)
A61J 1/00 (2006.01)
C03C 3/087 (2006.01)
C03C 3/091 (2006.01)
C03C 4/20 (2006.01)
C03C 21/00 (2006.01)
A61K 38/28 (2006.01)
A61K 38/29 (2006.01)
B65D 1/00 (2006.01)
C07K 16/18 (2006.01)
C07K 16/24 (2006.01)
C07K 16/28 (2006.01)

(52) U.S. Cl.
CPC ............. A61J 1/00 (2013.01); A61K 38/28 (2013.01); A61K 38/29 (2013.01); B65D 1/00 (2013.01); C03C 3/087 (2013.01); C03C 3/091 (2013.01); C03C 4/20 (2013.01); C03C 21/002 (2013.01); C07K 16/18 (2013.01); C07K 16/244 (2013.01); C07K 16/2863 (2013.01); C07K 16/2875 (2013.01); C07K 2317/94 (2013.01)

(58) Field of Classification Search
None
See application file for complete search history.

(56) References Cited

U.S. PATENT DOCUMENTS

| 1,115,972 | A | 11/1914 | Potter |
| 2,344,630 | A | 3/1944 | Mylchreest |
| 3,054,686 | A | 9/1962 | Hagedorn |
| RE25,456 | E | 10/1963 | Bacon et al. |
| 3,351,474 | A | 11/1967 | Hagedorn et al. |
| 3,490,885 | A | 1/1970 | Hammer |
| 3,673,049 | A | 6/1972 | Giffen et al. |
| 3,728,095 | A | 4/1973 | Grubb et al. |
| 3,772,135 | A | 11/1973 | Hara et al. |
| 3,844,754 | A | 10/1974 | Grubb et al. |
| 3,844,758 | A | 10/1974 | Wartenberg |
| 3,900,329 | A | 8/1975 | Grubb et al. |
| 3,936,287 | A | 2/1976 | Beall et al. |
| 4,021,218 | A | 5/1977 | Watanabe |
| 4,065,317 | A | 12/1977 | Baak et al. |
| 4,161,556 | A | 7/1979 | Lenard et al. |
| 4,312,953 | A | 1/1982 | Mills et al. |
| 4,689,085 | A | 8/1987 | Plueddemann |
| 4,842,630 | A | 6/1989 | Braithwaite et al. |
| 4,913,720 | A | 4/1990 | Gardon et al. |
| 5,114,757 | A | 5/1992 | Linde et al. |

(Continued)

FOREIGN PATENT DOCUMENTS

| CN | 101717189 A | 6/2010 |
| CN | 102123960 A | 7/2011 |

(Continued)

OTHER PUBLICATIONS

Adams RA. Formal discussion: the role of transplantation in the experimental; investigation of human leukemia and lymphoma. Cancer Res. Dec. 1967;27(12):2479-81.
Barrowcliffe TW, et al., Anticoagulant activities of lung and mucous heparins. Thromb Res. Jan. 1978;12(1):27-36.
Beum PV et al., Three new assays for rituximab based on its immunological activity or antigenic properties: analyses of sera and plasmas of RTX-treated patients with chronic lymphocytic leukemia and other B cell; lymphomas. J Immunol Methods. Jun. 2004; 289: 97-109.
Brunner KT et al. Quantitative assay of the lytic action of immune lymphoid cells on 51-Cr-labelled allogeneic target cells in vitro; inhibition by isoantibody and by drugs. Immunology. Feb. 1968;14(2):181-96.

(Continued)

Primary Examiner — Yunsoo Kim
(74) Attorney, Agent, or Firm — Michael G. Panian

(57) ABSTRACT

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage of pharmaceutical compositions and, specifically, a pharmaceutical solution comprising a pharmaceutically active ingredient, for example, FORTEO® (recombinant human teriparatide), DULAGLUTIDE® (LY2189265), recombinant insulin glargine, RAMUCIRUMAB® (IMC-1121B), SOLANEZUMAB® (LY2062430), IXEKIZUMAB® (LY2439821), TABALUMAB® (LY2127399), NECITUMUMAB® (IMC-11F8), or CIXUTUMUMAB® (IMC-A12).

12 Claims, 4 Drawing Sheets

(56) References Cited

U.S. PATENT DOCUMENTS

| | | |
|---|---|---|
| 5,286,527 A | 2/1994 | Blum et al. |
| 5,337,537 A | 8/1994 | Soughan |
| 5,547,929 A | 8/1996 | Anderson, Jr. et al. |
| 5,547,933 A | 8/1996 | Lin |
| 5,559,060 A | 9/1996 | Dumbaugh, Jr. et al. |
| 5,580,755 A | 12/1996 | Souza |
| 5,582,823 A | 12/1996 | Souza |
| 5,605,690 A | 2/1997 | Jacobs et al. |
| 5,656,722 A | 8/1997 | Dorschug |
| 5,721,181 A | 2/1998 | Sehgal et al. |
| 5,736,476 A | 4/1998 | Watzke et al. |
| 5,756,349 A | 5/1998 | Lin |
| 5,824,784 A | 10/1998 | Kinstler et al. |
| 5,854,153 A | 12/1998 | Kohli |
| 5,955,422 A | 9/1999 | Lin |
| RE36,755 E | 6/2000 | Smith et al. |
| 6,096,432 A | 8/2000 | Sakaguchi et al. |
| 6,156,399 A | 12/2000 | Spallek et al. |
| 6,214,429 B1 | 4/2001 | Zou et al. |
| 6,333,285 B1 | 12/2001 | Chopinet et al. |
| 6,472,068 B1 | 10/2002 | Glass et al. |
| 6,518,211 B1 | 2/2003 | Bradshaw et al. |
| 6,561,275 B2 | 5/2003 | Glass et al. |
| 6,599,594 B1 | 7/2003 | Walther et al. |
| 6,630,420 B1 | 10/2003 | Naumann et al. |
| 6,794,323 B2 | 9/2004 | Peuchert et al. |
| 6,818,576 B2 | 11/2004 | Ikenishi et al. |
| RE38,743 E | 6/2005 | Debrie |
| 6,939,819 B2 | 9/2005 | Usui et al. |
| 7,087,307 B2 | 8/2006 | Nagashima et al. |
| 7,315,125 B2 | 1/2008 | Kass |
| 7,470,999 B2 | 12/2008 | Saito et al. |
| 7,476,652 B2 | 1/2009 | Brunner-Schwarz et al. |
| 7,915,225 B2 | 3/2011 | Finck |
| 8,367,208 B2 | 2/2013 | Glaesemann et al. |
| 8,415,337 B1 | 4/2013 | Krishna |
| 8,518,545 B2 | 8/2013 | Akiba et al. |
| 8,551,898 B2 | 10/2013 | Danielson et al. |
| 8,753,994 B2 | 6/2014 | Danielson et al. |
| 8,756,994 B2 | 6/2014 | Yoneda et al. |
| 8,778,820 B2 | 7/2014 | Gomez et al. |
| 8,980,777 B2 | 3/2015 | Danielson et al. |
| 9,012,343 B2 | 4/2015 | Yamamoto et al. |
| 9,145,329 B2 | 9/2015 | Drake et al. |
| 9,186,295 B2 | 11/2015 | Weeks et al. |
| 9,198,829 B2 | 12/2015 | Weeks et al. |
| 9,241,869 B2 | 1/2016 | Weeks et al. |
| 9,340,447 B2 | 5/2016 | Danielson et al. |
| 2004/0096588 A1 | 5/2004 | Brandt |
| 2006/0008466 A1 | 1/2006 | Elahi et al. |
| 2006/0014670 A1 | 1/2006 | Green et al. |
| 2006/0154891 A1 | 7/2006 | Schridde et al. |
| 2006/0189533 A1* | 8/2006 | Quay .............. A61K 9/0043 514/11.8 |
| 2006/0246004 A1 | 11/2006 | Adams et al. |
| 2007/0004580 A1 | 1/2007 | Kass |
| 2007/0010700 A1 | 1/2007 | Bensmann et al. |
| 2007/0065366 A1 | 3/2007 | Soliani Raschini et al. |
| 2007/0123410 A1 | 5/2007 | Morena et al. |
| 2007/0157919 A1 | 7/2007 | Marandon |
| 2007/0191207 A1 | 8/2007 | Danielson et al. |
| 2007/0293388 A1 | 12/2007 | Zuyev et al. |
| 2008/0213282 A1 | 9/2008 | Jacob et al. |
| 2008/0281260 A1 | 11/2008 | William et al. |
| 2008/0308444 A1 | 12/2008 | McClain et al. |
| 2009/0131367 A1 | 5/2009 | Gore et al. |
| 2009/0163342 A1 | 6/2009 | Kolberg et al. |
| 2009/0197088 A1 | 8/2009 | Murata |
| 2009/0275462 A1 | 11/2009 | Murata |
| 2009/0291062 A1 | 11/2009 | Fraunhofer et al. |
| 2009/0325776 A1 | 12/2009 | Murata |
| 2010/0034850 A1 | 2/2010 | De Hemptinne et al. |
| 2010/0035038 A1 | 2/2010 | Barefoot et al. |
| 2010/0035745 A1 | 2/2010 | Murata |
| 2010/0047521 A1 | 2/2010 | Amin et al. |
| 2010/0074918 A1 | 3/2010 | Poolman |
| 2010/0120603 A1 | 5/2010 | Morena et al. |
| 2010/0226937 A1 | 9/2010 | Contorni |
| 2010/0255061 A1 | 10/2010 | de Juan, Jr. et al. |
| 2010/0304090 A1 | 12/2010 | Henn et al. |
| 2010/0317506 A1 | 12/2010 | Fechner et al. |
| 2011/0014475 A1 | 1/2011 | Murata |
| 2011/0017297 A1 | 1/2011 | Aitken et al. |
| 2011/0045960 A1 | 2/2011 | Fechner et al. |
| 2011/0045961 A1 | 2/2011 | Dejneka et al. |
| 2011/0062619 A1 | 3/2011 | Laine et al. |
| 2011/0066111 A1 | 3/2011 | Teschner et al. |
| 2011/0071012 A1 | 3/2011 | Kondo et al. |
| 2011/0091704 A1 | 4/2011 | Akiba et al. |
| 2011/0098172 A1 | 4/2011 | Brix |
| 2011/0123832 A1 | 5/2011 | Matsumoto et al. |
| 2011/0135938 A1 | 6/2011 | Kim et al. |
| 2011/0159318 A1 | 6/2011 | Endo et al. |
| 2011/0177987 A1 | 7/2011 | Lenting et al. |
| 2011/0226658 A1 | 9/2011 | Tata-Venkata et al. |
| 2011/0274916 A1 | 11/2011 | Murata |
| 2011/0281093 A1 | 11/2011 | Gulati et al. |
| 2011/0287046 A1 | 11/2011 | Oloo et al. |
| 2012/0052088 A1 | 3/2012 | Davis et al. |
| 2012/0100329 A1 | 4/2012 | Baratta |
| 2012/0135226 A1 | 5/2012 | Bookbinder et al. |
| 2012/0135853 A1 | 5/2012 | Amin et al. |
| 2012/0148770 A1 | 6/2012 | Rong et al. |
| 2012/0183812 A1 | 7/2012 | Kajita |
| 2012/0199203 A1 | 8/2012 | Nishizawa et al. |
| 2012/0208309 A1 | 8/2012 | Tsujimura et al. |
| 2012/0234368 A1 | 9/2012 | Cintora et al. |
| 2012/0277085 A1 | 11/2012 | Bookbinder et al. |
| 2012/0297829 A1 | 11/2012 | Endo et al. |
| 2013/0004758 A1 | 1/2013 | Dejneka et al. |
| 2013/0011650 A1 | 1/2013 | Akiba et al. |
| 2013/0045375 A1 | 2/2013 | Gross |
| 2013/0101596 A1 | 4/2013 | DeMartino et al. |
| 2013/0101764 A1 | 4/2013 | Schaut et al. |
| 2013/0101766 A1 | 4/2013 | Danielson et al. |
| 2013/0101853 A1 | 4/2013 | Drake et al. |
| 2013/0122284 A1 | 5/2013 | Gross |
| 2013/0196094 A1 | 8/2013 | Weeks et al. |
| 2013/0196095 A1 | 8/2013 | Weeks et al. |
| 2013/0196096 A1 | 8/2013 | Weeks et al. |
| 2013/0196097 A1 | 8/2013 | Weeks et al. |
| 2013/0202823 A1 | 8/2013 | Weeks et al. |
| 2013/0213848 A1 | 8/2013 | Weeks et al. |
| 2013/0216742 A1 | 8/2013 | DeMartino et al. |
| 2013/0344263 A1 | 12/2013 | Danielson et al. |
| 2014/0023865 A1 | 1/2014 | Comte et al. |
| 2014/0120279 A1 | 5/2014 | DeMartino et al. |
| 2014/0154440 A1 | 6/2014 | Iida et al. |
| 2014/0272215 A1 | 9/2014 | Danielson et al. |
| 2014/0339122 A1 | 11/2014 | Weeks et al. |
| 2014/0339125 A1 | 11/2014 | Weeks et al. |
| 2014/0339126 A1 | 11/2014 | Weeks et al. |
| 2014/0341883 A1 | 11/2014 | Weeks et al. |
| 2014/0341888 A1 | 11/2014 | Weeks et al. |
| 2014/0341889 A1 | 11/2014 | Weeks et al. |
| 2014/0341890 A1 | 11/2014 | Weeks et al. |
| 2014/0341891 A1 | 11/2014 | Weeks et al. |
| 2014/0341945 A1 | 11/2014 | Weeks et al. |
| 2014/0342979 A1 | 11/2014 | Weeks et al. |
| 2015/0037571 A1 | 2/2015 | Danielson et al. |
| 2015/0071913 A1 | 3/2015 | Weeks et al. |
| 2015/0079318 A1 | 3/2015 | Danielson et al. |
| 2015/0157533 A1 | 6/2015 | DeMartino et al. |
| 2015/0232374 A1 | 8/2015 | Danielson et al. |
| 2015/0366756 A1 | 12/2015 | Weeks et al. |
| 2015/0374582 A1 | 12/2015 | Weeks et al. |
| 2016/0095795 A1 | 4/2016 | Weeks et al. |
| 2016/0095796 A1 | 4/2016 | Weeks et al. |

FOREIGN PATENT DOCUMENTS

| | | |
|---|---|---|
| DE | 29702816 U1 | 4/1997 |
| DE | 102004011009 A1 | 9/2005 |
| EP | 0515801 A1 | 12/1992 |

(56) References Cited

FOREIGN PATENT DOCUMENTS

| | | |
|---|---|---|
| EP | 1074521 A2 | 2/2001 |
| EP | 2031124 A1 | 3/2009 |
| EP | 2540682 A1 | 1/2013 |
| EP | 2771295 A1 | 9/2014 |
| GB | 966731 A | 8/1964 |
| GB | 1115972 A | 6/1968 |
| GB | 1334828 A | 10/1973 |
| GB | 2335423 A | 9/1999 |
| IN | 231117 | 3/2009 |
| JP | 7223845 | 8/1995 |
| JP | H09-124338 A | 5/1997 |
| JP | H09-124339 A | 5/1997 |
| JP | H09-241033 A | 9/1997 |
| JP | 11314931 | 11/1999 |
| JP | 2000007372 A | 1/2000 |
| JP | 2001180969 A | 7/2001 |
| JP | 2001192239 A | 7/2001 |
| JP | 2001229526 A | 8/2001 |
| JP | 2001236634 A | 8/2001 |
| JP | 2002003241 A | 1/2002 |
| JP | 2002025762 A | 1/2002 |
| JP | 2002249340 A | 9/2002 |
| JP | 2004067443 A | 3/2004 |
| JP | 2004131314 A | 4/2004 |
| JP | 2008195602 A | 8/2008 |
| JP | 2010059038 A | 3/2010 |
| JP | 2010202413 A | 9/2010 |
| JP | 2011093728 A | 5/2011 |
| JP | 2011136895 A | 7/2011 |
| JP | 2012184118 A | 9/2012 |
| KR | 630309 | 5/2006 |
| RO | 83460 A2 | 3/1984 |
| SU | 990700 A1 | 1/1983 |
| WO | WO-9624559 A1 | 8/1996 |
| WO | WO-9725932 A1 | 7/1997 |
| WO | WO-9905070 A1 | 2/1999 |
| WO | WO-2007025932 A2 | 3/2007 |
| WO | WO-2008050500 A1 | 5/2008 |
| WO | WO-2008143999 A1 | 11/2008 |
| WO | WO-2009002660 A2 | 12/2008 |
| WO | WO-2009053947 A2 | 4/2009 |
| WO | WO-2009097123 A1 | 8/2009 |
| WO | WO-2010084670 A1 | 7/2010 |
| WO | WO-2011007785 A1 | 1/2011 |
| WO | WO-2011049146 A1 | 4/2011 |
| WO | WO-2011069338 A1 | 6/2011 |
| WO | WO-2011103798 A1 | 9/2011 |
| WO | WO-2011103799 A1 | 9/2011 |
| WO | WO-2011145661 A1 | 11/2011 |
| WO | WO-2011151760 A2 | 12/2011 |
| WO | WO-2012026290 A1 | 3/2012 |
| WO | WO-2012124757 A1 | 9/2012 |
| WO | WO-2013021975 A1 | 2/2013 |
| WO | WO-2013/063277 A1 | 5/2013 |
| WO | WO-2013063275 A1 | 5/2013 |
| WO | WO-2013063280 A1 | 5/2013 |
| WO | WO-2013063283 A1 | 5/2013 |
| WO | WO-2013063287 A1 | 5/2013 |
| WO | WO-2013063290 A1 | 5/2013 |
| WO | WO-2013063292 A1 | 5/2013 |

OTHER PUBLICATIONS

Casset et al., "A peptide mimetic of an anti-CD4 monoclonal antibody by rational design", Biochem Biophys Res Commun. Jul. 18, 2003; vol. 307, No. 1, pp. 198-205.
Corrected Notice of Allowance mailed Sep. 11, 2013, relating to U.S. Appl. No. 13/660,394, filed Oct. 25, 2012.
Cortez-Retamozo et al., "Efficient cancer therapy with a nanobody-based conjugate", Cancer Research, Apr. 15, 2004, vol. 64, No. 8, pp. 2853-2857.
Cotes PM, et al., Bio-assay of erythropoietin in mice made polycythaemic by exposure to air at a reduced pressure. Nature. Sep. 9, 1961;191:1065-7.
Database WPI Week 198434 Thomsen Scientific, London, GB; AN 1984-211366 XP002690017.
Davis-Smyth T et al., The second immunoglobulin-like domain of the VEGF tyrosine kinase receptor Flt-1 determines ligand binding and may initiate a signal transduction cascade. EMBO J. Sep. 16, 1996;15(18):4919-27.
Drugs.com, Enbrel, May 28, 2010.
Drugs.com, Neulasta®, Sep. 13, 2010.
Fassina, G., "Complementary peptides as antibody mimetics for protein purification and assay", Immunomethods, Oct. 1994; vol. 5, No. 2, pp. 121-129.
Ferrara N, et al., Vascular endothelial growth factor is essential for corpus luteum angiogenesis. Nat Med. Mar. 1998;4(3):336-40.
Goldwasser E, et al., An assay for erythropoietin in vitro at the milliunit level. Endocrinology. Aug. 1975;97(2):315-23.
Hammond D, et al., Production, utilization and excretion of erythropoietin. I. Chronic anemias. II. Aplastic crisis. 3. Erythropoietic effects of normal plasma. Ann N Y Acad Sci. Mar. 29, 1968;149(1):516-27.
Holash J, et al., VEGF-Trap: a VEGF blocker with potent antitumor effects. Proc Natl Acad Sci U S A. Aug. 20, 2002;99(17):11393-8.
Horton RM et al., Engineering hybrid genes without the use of restriction enzymes: gene splicing by overlap extension. Gene. Apr. 15, 1989;77(1):61-8.
Humana Abbreviated Formulary List of Covered Drugs, 2010 Prescription Drug Guide.
International Search Report & Written Opinion relating to PCT/US2012/061940 filed Oct. 25, 2012; Mail Date: Jan. 30, 2013.
International Search Report & Written Opinion relating to PCT/US2012/061943 filed Oct. 25, 2012; Mail Date: Jan. 30, 2013.
International Search Report & Written Opinion relating to PCT/US2012/061946 filed Oct. 25, 2012; Mail Date: Jan. 30, 2013.
International Search Report & Written Opinion relating to PCT/US2012/061949 filed Oct. 25, 2012; Mail Date: Jan. 30, 2013.
International Search Report & Written Opinion relating to PCT/US2012/061953 filed Oct. 25, 2012; Mail Date: Jan. 30, 2013.
International Search Report & Written Opinion relating to PCT/US2012/061956 filed Oct. 25, 2012; Mail Date: Jan. 30, 2013.
International Search Report & Written Opinion relating to PCT/US2012/061958 filed Oct. 25, 2012; Mail Date: Jan. 30, 2013.
International Search Report & Written Opinion relating to PCT/US2013/048589 filed Jun. 28, 2013; Mail Date: Oct. 28, 2013.
International Search Report relating to PCT/US2012/061867; Mail Date: Jan. 30, 2013.
International Search Report relating to PCT/US2012/061939; Mail Date: Jan. 30, 2013.
IPRP & Written Opinion relating to PCT/US2012/061867 filed Oct. 25, 2012; Mail Date: May 8, 2014.
IPRP & Written Opinion relating to PCT/US2012/061939 filed Oct. 25, 2012; Mail Date: May 8, 2014.
IPRP & Written Opinion relating to PCT/US2012/061940 filed Oct. 25, 2012; Mail Date: May 8, 2014.
IPRP & Written Opinion relating to PCT/US2012/061943 filed Oct. 25, 2012; Mail Date: May 8, 2014.
IPRP & Written Opinion relating to PCT/US2012/061946 filed Oct. 25, 2012; Mail Date: May 8, 2014.
IPRP & Written Opinion relating to PCT/US2012/061949 filed Oct. 25, 2012; Mail Date: May 8, 2014.
IPRP & Written Opinion relating to PCT/US2012/061953 filed Oct. 25, 2012; Mail Date: May 8, 2014.
IPRP & Written Opinion relating to PCT/US2012/061956, filed Oct. 25, 2012; Mail date: May 8, 2014.
IPRP & Written Opinion relating to PCT/US2012/061958 filed Oct. 25, 2012; Mail Date: May 8, 2014.
IPRP & Written Opinion relating to PCT/US2013/048589 filed Jun. 28, 2013; Mail Date: Jan. 8, 2015.
Karch, AM, "2006 Lippincott's Nursing Drug Guide," Publisher: Lippincott Williams & Wilkins, ISBN: 1582554382, 2006.
Lane DA, et al., Anticoagulant activities of four unfractionated and fractionated heparins. Thromb Res. Feb. 1978;12(2):257-71.
Lichtlen P, Lam TT, Nork TM, Streit T, Urech DM. Relative contribution of VEGF and TNF-alpha in the cynomolgus laser-

(56) References Cited

OTHER PUBLICATIONS induced CNV model: comparing the efficacy of bevacizumab, adalimumab, and SBA105. Invest Ophthalmol Vis Sci. Sep. 2010;51(9):4738-45.

Lytle et al., "Predicted Inactivation of Viruses of Relevance to Biodefense by Solar Radiation," J. Virol. 79(22): 14244-14252 (2005).

Metcalf D. Clonal extinction of myelomonocytic leukemic cells by serum from; mice injected with endotoxin. Int J Cancer. Feb. 15, 1980;25(2):225-33.

Murphy, D. B. and Davidson, M. W., "Differential Interference Contrast (DIC) Microscopy and Modulation Contrast" form Fundamentals of Light Microscopy and Electronic Imaging Published 2001, Publisher, Wiley, pp. 153-168.

Nandi et al., "Development and Applications of Varieties of Bioactive Glass Compositions in Dental Surgery, Third Generation Tissue Engineering, Orthopaedic Surgery and as Drug Delivery System," Biomaterial Applications for Nanomedicine, Professor Rosario Pignatello (Ed.), 2011, ISBN: 978-953-307-661-4, InTech, available at cdn.intechopen.com/pdfs/23619/InTech-Development_and_applications_of_varieties_of_bioactive_glass_compositions_in_dental_surgery_third_generation_tissue_engineering_orthopaedic_surgery_and_as_drug_delivery_system.pdf, last accessed Nov. 25, 2015.

Non-Final Office Action mailed Mar. 14, 2013, relating to U.S. Appl. No. 13/660,394, filed Oct. 25, 2012.

Notice of Allowance mailed Jun. 27, 2013, relating to U.S. Appl. No. 13/660,394, filed Oct. 25, 2012.

Pharmaceutical Drug Manufacturers, Erythropoietin Injection, Sep. 18, 2008.

Randle PJ., "Assay of plasma insulin activity by the rat-diaphragm method", British Medical Journal, May 29, 1954, vol. 1 (4873), pp. 1237-1240.

Reynolds et al., "Glass Delamination and Breakage", Bioprocess International, Dec. 1, 2011, vol. 9, No. 11, pp. 52-57.

Ribel U, Subcutaneous absorption of insulin analogues. In Frontiers in Insulin Pharmacology, Berger M, Gries FA (eds), Thieme Verlag, pp. 70-77 (1993).

Ribel U., et al., The pig as a model for subcutaneous insulin absorption in man. Serrano_Rios, M and Lefebvre, P.J. 891-896. 1985. Amsterdam; New York; Oxford, Elsevier Science Publishers. 1985 (Conference Proceeding).

Roche Consumer Medicine Information, Neupogen®, Feb. 3, 2010.

Saragovi et al., "Design and synthesis of a mimetic from an antibody complementarity-determining region", Science, Aug. 16, 1991, vol. 253, No. 5021, pp. 792-795.

Silva M, et al., Erythropoietin can induce the expression of bcl-x(L) through Stat5 in erythropoietin-dependent progenitor cell lines. J Biol Chem. Aug. 6, 1999;274(32):22165-9.

Tarrant, "Production and Properties of Glass Containers," Journal of the Society for Cosmetic Chemists, vol. 13, No. 1:15-42 (1962).

Teien AN, et al., Evaluation of an amidolytic heparin assay method: increased sensitivity by adding purified antithrombin III. Thromb Res. Mar. 1977;10(3):399-410.

Ternant D, et al., An enzyme-linked immunosorbent assay for therapeutic drug monitoring of infliximab. Ther Drug Monit. Apr. 2006;28(2):169-74.

U.S. Food and Drug Administration, Package Insert HUMIRA (adalimumab) Abbott Laboratories, 2010.

Ueda et al., "Age-dependent changes in phenotypes and candidate gene analysis in a polygenic animal model of Type II diabetes mellitus; NSY mouse" Diabetologia, Jul. 2000, vol. 43, Issue 7, pp. 932-938.

Veer et al., "The strength of glass, a nontransparent value," HERON vol. 52, No. 1/2, pp. 87-104 (2007).

Wen, Zai-Qing et al., "Nondestructive detection of glass vial inner surface morphology with differential interference contrast microscopy", Journal of Pharmaceutical Sciences, Apr. 2012, vol. 101, Issue 4, pp. 1378-1384.

Yu L et al., Interaction between bevacizumab and murine VEGF-A: a reassessment. Invest Ophthalmol Vis Sci. Feb. 2008;49(2):522-7.

[No Author Listed] European Pharmacopeia, 5th edition, Council of Europe, Jul. 2004, Preface pp. i-iii and Section 3.2 Containers, p. 303.

[No Author Listed] U.S. Pharmacopeial Convention Medicines Compendium, Monographs, Section 660, Containers—Glass, retrieved from mc.usp.org/general-chapters, 5 pages, last accessed Aug. 21, 2014.

Ciullo, PA, "Industrial Minerals and Their Uses—A Handbook & Formulary," William Andrew Publishing/Noyes, Westwood, New Jersey, 1996, Chapter 11: Ceramics and Glass, pp. 459-463.

Lucentis product information, Novartis, 2007, p. 1-35.

Varshneya, A. K., "Chemical Strengthening of Glass: Lessons Learned and Yet to Be Learned", International Journal of Applied Glass Science 1 [2] 131-142 (2010).

Gomez, et al., "A look at the chemical strengthening process: alkali aluminosilicate glasses vs. soda-lime glass," 71st Conference on Glass Problems, Editro: Charles H. Drummond, III, The American Society, 2011, p. 62-66.

International Search Report & Written Opinion relating to PCT/US2012/061911 filed Oct. 25, 2012; Mail Date: Jan. 30, 2013.

International Search Report & Written Opinion relating to PCT/US2013/028184 filed Feb. 28, 2013; Mail Date: Jul. 11, 2013.

IPRP & Written Opinion relating to PCT/US2013/028184 filed Feb. 28, 2013; Mail Date: Sep. 12, 2014.

\* cited by examiner

SEQUENCE LISTING

```
<160> NUMBER OF SEQ ID NOS: 3

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30
```

DELAMINATION RESISTANT PHARMACEUTICAL GLASS CONTAINERS CONTAINING ACTIVE PHARMACEUTICAL INGREDIENTS

CROSS REFERENCE TO RELATED APPLICATIONS

The present application is related to U.S. Provisional Application No. 61/815,704, filed Apr. 24, 2013, entitled "Delamination Resistant Pharmaceutical Glass Containers Containing Active Pharmaceutical Ingredients", the entirety of which is hereby incorporated by reference herein.

SEQUENCE LISTING

The instant application contains a Sequence Listing which has been submitted electronically in ASCII format and is hereby incorporated by reference in its entirety. Said ASCII copy, created on Apr. 21, 2014, is named 122467-01402_SL.txt and is 1,608 bytes in size.

FIELD OF THE INVENTION

The present specification generally relates to pharmaceutical containers and, more specifically, to chemically and mechanically durable pharmaceutical containers that are delamination resistant and formed, at least in part, of a glass composition.

BACKGROUND

The design of a packaged pharmaceutical composition generally seeks to provide an active pharmaceutical ingredient (API) in a suitable package that is convenient to use, that maintains the stability of the API over prolonged storage, and that ultimately allows for the delivery of efficacious, stable, active, nontoxic and nondegraded API.

Most packaged formulations are complex physico-chemical systems, through which the API is subject to deterioration by a variety of chemical, physical, and microbial reactions. Interactions between drugs, adjuvants, containers, and/or closures may occur, which can lead to the inactivation, decomposition and/or degradation of the API.

Historically, glass has been used as the preferred material for packaging pharmaceuticals because of its hermeticity, optical clarity and excellent chemical durability relative to other materials. Specifically, the glass used in pharmaceutical packaging must have adequate chemical durability so as not to affect the stability of the pharmaceutical compositions contained therein. Glasses having suitable chemical durability include those glass compositions within the ASTM standard 'Type 1B' glass compositions which have a proven history of chemical durability.

However, use of glass for such applications is limited by the mechanical performance of the glass. Specifically, in the pharmaceutical industry, glass breakage is a safety concern for the end user as the broken package and/or the contents of the package may injure the end user. Further, non-catastrophic breakage (i.e., when the glass cracks but does not break) may cause the contents to lose their sterility which, in turn, may result in costly product recalls.

One approach to improving the mechanical durability of the glass package is to thermally temper the glass package. Thermal tempering strengthens glass by inducing a surface compressive stress during rapid cooling after forming. This technique works well for glass articles with flat geometries (such as windows), glass articles with thicknesses >2 mm, and glass compositions with high thermal expansion. However, pharmaceutical glass packages typically have complex geometries (vial, tubular, ampoule, etc.), thin walls (~1-1.5 mm), and are produced from low expansion glasses (30–55×$10^{-7}K^{-1}$) making glass pharmaceutical packages unsuitable for strengthening by thermal tempering.

Chemical tempering also strengthens glass by the introduction of surface compressive stress. The stress is introduced by submerging the article in a molten salt bath. As ions from the glass are replaced by larger ions from the molten salt, a compressive stress is induced in the surface of the glass. The advantage of chemical tempering is that it can be used on complex geometries, thin samples, and is relatively insensitive to the thermal expansion characteristics of the glass substrate. However, glass compositions which exhibit a moderate susceptibility to chemical tempering generally exhibit poor chemical durability and vice-versa.

Finally, glass compositions commonly used in pharmaceutical packages, e.g., Type 1a and Type 1b glass, further suffer from a tendency for the interior surfaces of the pharmaceutical package to shed glass particulates or "delaminate" following exposure to pharmaceutical solutions. Such delamination often destabilizes the active pharmaceutical ingredient (API) present in the solution, thereby rendering the API therapeutically ineffective or unsuitable for therapeutic use.

Delamination has caused the recall of multiple drug products over the last few years (see, for example, Reynolds et al., (2011) BioProcess International 9(11) pp. 52-57). In response to the growing delamination problem, the U.S. Food and Drug Administration (FDA) has issued an advisory indicating that the presence of glass particulate in injectable drugs can pose a risk.

The advisory states that, "[t]here is potential for drugs administered intravenously that contain these fragments to cause embolic, thrombotic and other vascular events; and subcutaneously to the development of foreign body granuloma, local injections site reactions and increased immunogenicity."

Accordingly, a recognized need exists for alternative glass containers for packaging of pharmaceutical compositions which exhibit a reduced propensity to delaminate.

SUMMARY

In one aspect, the present invention is directed to a delamination resistant pharmaceutical container formed, at least in part, of a glass composition including from about 70 mol. % to about 80 mol. % $SiO_2$; from about 3 mol. % to about 13 mol. % alkaline earth oxide; X mol. % $Al_2O_3$; and Y mol. % alkali oxide, wherein the alkali oxide includes $Na_2O$ in an amount greater than about 8 mol. %, wherein the ratio of Y:X is greater than 1, and the glass composition is free of boron and compounds of boron.

In one embodiment, the $SiO_2$ is present in an amount less than or equal to 78 mol. %.

In one embodiment, the amount of the alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) that is less than or equal to 0.5. In a particular embodiment, the alkaline earth oxide includes from about 0.1 mol. % to less than or equal to about 1.0 mol. % CaO. In a particular embodiment, the alkaline earth oxide includes from about 3 mol. % to about 7 mol. % MgO.

In another embodiment, the alkali oxide includes greater than or equal to about 9 mol. % $Na_2O$ and less than or equal to about 15 mol. % $Na_2O$. In another embodiment, the alkali oxide further includes $K_2O$ in an amount less than or equal to about 3 mol. %. In a particular embodiment, the alkali oxide includes $K_2O$ in an amount greater than or equal to about 0.01 mol. % and less than or equal to about 1.0 mol. %.

In one embodiment, X is greater than or equal to about 2 mol. % and less than or equal to about 10 mol. %. In a particular embodiment, the ratio of Y:X is less than or equal to 2. In a particular embodiment, the ratio of Y:X is greater than or equal to 1.3 and less than or equal to 2.0.

In another embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 μm and a surface compressive stress greater than or equal to 250 MPa.

In another aspect, the present invention provides a delamination resistant pharmaceutical container formed, at least in part, of a glass composition including from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %.; and Y mol. % alkali oxide, wherein the alkali oxide includes $Na_2O$ in an amount greater than or equal to about 9 mol. % and less than or equal to about 15 mol. %, wherein the ratio of Y:X is greater than 1, and the glass composition is free of boron and compounds of boron.

In a particular embodiment, the ratio of Y:X is less than or equal to about 2. In a particular embodiment, the ratio of Y:X is greater than or equal to about 1.3 and less than or equal to about 2.0.

In one embodiment, the alkaline earth oxide includes MgO and CaO and has a ratio (CaO (mol. %)/(CaO (mol. %)+MgO (mol. %))) less than or equal to 0.5.

In another embodiment, the alkali oxide includes $K_2O$ in an amount greater than or equal to about 0.01 mol. % and less than or equal to about 1.0 mol. %.

In another aspect, the present invention provides a delamination resistant pharmaceutical container formed, at least in part, of a glass composition including from about 68 mol. % to about 80 mol. % $SiO_2$; from about 3 mol. % to about 13 mol. % alkaline earth oxide; X mol. % $Al_2O_3$; Y mol. % alkali oxide, wherein the alkali oxide includes $Na_2O$ in an amount greater than about 8 mol. %; and $B_2O_3$, wherein the ratio ($B_2O_3$ (mol. %)/(Y mol. %–X mol. %) is greater than 0 and less than 0.3, and the ratio of Y:X is greater than 1.

In one embodiment, the amount of $SiO_2$ is greater than or equal to about 70 mol. %.

In one embodiment, the amount of alkaline earth oxide is greater than or equal to about 4 mol. % and less than or equal to about 8 mol. %. In a particular embodiment, the alkaline earth oxide includes MgO and CaO and has a ratio (CaO (mol. %)/(CaO (mol. %)+MgO (mol. %))) less than or equal to 0.5. In a particular embodiment, the alkaline earth oxide includes CaO in an amount greater than or equal to about 0.1 mol. % and less than or equal to about 1.0 mol. %. In a particular embodiment, the alkaline earth oxide includes from about 3 mol. % to about 7 mol. % MgO.

In one embodiment, the alkali oxide is greater than or equal to about 9 mol. % $Na_2O$ and less than or equal to about 15 mol. % $Na_2O$. In a particular embodiment, the alkali oxide further includes $K_2O$ in a concentration less than or equal to about 3 mol. %. In another embodiment, the alkali oxide further includes $K_2O$ in a concentration greater than or equal to about 0.01 mol. % and less than or equal to about 1.0 mol. %.

In another embodiment, the pharmaceutical container has a ratio ($B_2O_3$ (mol. %)/(Y mol. %–X mol. %) less than 0.2. In a particular embodiment, the amount of $B_2O_3$ is less than or equal to about 4.0 mol. %. In another embodiment, the amount of $B_2O_3$ is greater than or equal to about 0.01 mol. %.

In one embodiment, X is greater than or equal to about 2 mol. % and less than or equal to about 10 mol. %. In a particular embodiment, the ratio of Y:X is less than or equal to 2. In another embodiment, the ratio of Y:X is greater than 1.3.

In one embodiment, the glass composition is free of phosphorous and compounds of phosphorous.

In one embodiment, the glass composition has a type HGB1 hydrolytic resistance according to ISO 719. Alternatively or in addition, the glass composition has a type HGA1 hydrolytic resistance according to ISO 720 after ion exchange strengthening. Alternatively or in addition, the glass composition has a type HGA1 hydrolytic resistance according to ISO 720 before and after ion exchange strengthening. Alternatively or in addition, the glass composition has at least a class S3 acid resistance according to DIN 12116. Alternatively or in addition, the glass composition has at least a class A2 base resistance according to ISO 695.

In one embodiment, the glass composition is ion exchange strengthened.

In another embodiment, the composition further includes a compressive stress layer with a depth of layer greater than or equal to 10 μm and a surface compressive stress greater than or equal to 250 MPa.

In one embodiment of any of the foregoing aspects of the invention, the pharmaceutical container further includes a pharmaceutical composition having an active pharmaceutical ingredient. In a particular embodiment, the pharmaceutical composition includes a citrate or phosphate buffer, for example, sodium citrate, SSC, monosodium phosphate or disodium phosphate. Alternatively or in addition, the pharmaceutical composition has a pH between about 7 and about 11, between about 7 and about 10, between about 7 and about 9, or between about 7 and about 8.

In one embodiment of any of the foregoing aspects of the invention, the active pharmaceutical ingredient is recombinant human parathyroid hormone analog (1-34), [rhPTH(1-34)], or analog thereof. In one embodiment, the pharmaceutical composition is FORTEO ([rhPTH(1-34)]).

In one embodiment of any of the foregoing aspects of the invention, the active pharmaceutical ingredient is a glucagon-like peptide-1 (GLP-1) immunoglobulin G (IgG4) Fc fusion protein, or an analog thereof. In one embodiment, the pharmaceutical composition is DULAGLUTIDE (LY2189265).

In one embodiment of any of the foregoing aspects of the invention, the active pharmaceutical ingredient is recombinant human insulin glargine, or an analog thereof.

In one embodiment of any of the foregoing aspects of the invention, the active pharmaceutical ingredient is a human monoclonal (IgG1) anti-vascular endothelial growth factor receptor-2 (VEGFR-2) antibody. In a particular embodiment, the pharmaceutical composition is RAMUCIRUMAB (IMC-1121B).

In one embodiment of any of the foregoing aspects of the invention, the active pharmaceutical ingredient is a humanized monoclonal anti-β-amyloid antibody. In a particular embodiment, the pharmaceutical composition is SOLANEZUMAB (LY2062430).

In one embodiment of any of the foregoing aspects of the invention, the active pharmaceutical ingredient is a humanized monoclonal anti-interleukin-17 (IL-17A) antibody. In a particular embodiment, the pharmaceutical composition is IXEKIZUMAB (LY2439821).

In one embodiment of any of the foregoing aspects of the invention, the active pharmaceutical ingredient is a human monoclonal anti-TNFSF13b antibody. In a particular embodiment, the pharmaceutical composition is TABALUMAB (LY2127399).

In one embodiment of any of the foregoing aspects of the invention, the active pharmaceutical ingredient is a human anti-epidermal growth factor receptor (EGFR) antibody. In a particular embodiment, the pharmaceutical composition is NECITUMUMAB (IMC-11F8).

In one embodiment of any one of the foregoing aspects of the invention, the active pharmaceutical ingredient is a human monoclonal (IgG1) anti-insulin-like growth factor-1 (IGF-1) receptor antibody. In a particular embodiment, the pharmaceutical composition is CIXUTUMUMAB (IMC-A12).

In a particular aspect, the present invention provides a delamination resistant pharmaceutical container formed, at least in part, of a glass composition including about 76.8 mol. % $SiO_2$; about 6.0 mol. % $Al_2O_3$; about 11.6 mol. % $Na_2O$; about 0.1 mol. % $K_2O$; about 4.8 mol. % MgO; and about 0.5 mol. % CaO, wherein the glass composition is free of boron and compounds of boron; and wherein the pharmaceutical container further comprises a pharmaceutical composition selected from the group consisting of FORTEO ([rhPTH(1-34]), DULAGLUTIDE (LY2189265), recombinant human insulin glargine, RAMUCIRUMAB (IMC-1121B), SOLANEZUMAB (LY2062430), IXEKUZUMAB (LY2439821), TABALUMAB (LY2127399), NECITUMUMAB (IMC-11F8), and CIXUTUMUMAB (IMC-A12).

In one aspect, the present invention includes a delamination resistant pharmaceutical container including a glass composition. The pharmaceutical container includes from about 70 mol. % to about 80 mol. % $SiO_2$; from about 3 mol. % to about 13 mol. % alkaline earth oxide; X mol. % $Al_2O_3$; and Y mol. % alkali oxide. The alkali oxide includes $Na_2O$ in an amount greater than about 8 mol. %, a ratio of Y:X is greater than 1, and the glass composition is free of boron and compounds of boron. The delamination resistant pharmaceutical container further includes an active pharmaceutical ingredient.

In one or more embodiments, the $SiO_2$ is present in an amount less than or equal to 78 mol. %. In some embodiments, an amount of the alkaline earth oxide is greater than or equal to about 4 mol. % and less than or equal to about 8 mol. %. In one or more embodiments, the alkaline earth oxide includes MgO and CaO and a ratio (CaO (mol. %)/(CaO (mol. %)+MgO (mol. %))) is less than or equal to 0.5. In one or more embodiments, the alkaline earth oxide includes from about 0.1 mol. % to less than or equal to about 1.0 mol. % CaO. In one or more embodiments, the alkaline earth oxide includes from about 3 mol. % to about 7 mol. % MgO. In one or more embodiments, X is greater than or equal to about 2 mol. % and less than or equal to about 10 mol. %. In embodiments, the alkali oxide includes greater than or equal to about 9 mol. % $Na_2O$ and less than or equal to about 15 mol. % $Na_2O$. In some embodiments, the ratio of Y:X is less than or equal to 2. In one or more embodiments, the ratio of Y:X is greater than or equal to 1.3 and less than or equal to 2.0. In one or more embodiments, the alkali oxide further includes $K_2O$ in an amount less than or equal to about 3 mol. %. In one or more embodiments, the glass composition is free of phosphorous and compounds of phosphorous. In one or more embodiments, the alkali oxide includes $K_2O$ in an amount greater than or equal to about 0.01 mol. % and less than or equal to about 1.0 mol. %.

In another aspect, the invention includes a delamination resistant pharmaceutical container including a pharmaceutical composition. The pharmaceutical container includes an active pharmaceutical ingredient, such that the pharmaceutical container includes a glass composition including $SiO_2$ in a concentration greater than about 70 mol. %; alkaline earth oxide including MgO and CaO, wherein CaO is present in an amount greater than or equal to about 0.1 mol. % and less than or equal to about 1.0 mol. %, and a ratio (CaO (mol. %)/(CaO (mol. %)+MgO (mol. %))) is less than or equal to 0.5; and Y mol. % alkali oxide, wherein the alkali oxide includes $Na_2O$ in an amount greater than about 8 mol. %, such that the glass composition is free of boron and compounds of boron.

In another aspect, the invention includes a delamination resistant pharmaceutical container including a pharmaceutical composition including an active pharmaceutical ingredient. The pharmaceutical container includes a glass composition including from about 72 mol. % to about 78 mol. % $SiO_2$; from about 4 mol. % to about 8 mol. % alkaline earth oxide, wherein the alkaline earth oxide includes MgO and CaO and a ratio (CaO (mol. %)/(CaO (mol. %)+MgO (mol. %))) is less than or equal to 0.5; X mol. % $Al_2O_3$, such that X is greater than or equal to about 4 mol. % and less than or equal to about 8 mol. %.; and Y mol. % alkali oxide, such that the alkali oxide includes $Na_2O$ in an amount greater than or equal to about 9 mol. % and less than or equal to about 15 mol. %, a ratio of Y:X is greater than 1, and the glass composition is free of boron and compounds of boron.

In another aspect, the invention includes a delamination resistant pharmaceutical container including a pharmaceutical composition including an active pharmaceutical ingredient. The pharmaceutical container includes a glass composition. The glass composition includes from about 70 mol. % to about 80 mol. % $SiO_2$; from about 3 mol. % to about 13 mol. % alkaline earth oxide, such that the alkaline earth oxide includes CaO in an amount greater than or equal to about 0.1 mol. % and less than or equal to about 1.0 mol. %, MgO, and a ratio (CaO (mol. %)/(CaO (mol. %)+MgO (mol. %))) is less than or equal to 0.5; X mol. % $Al_2O_3$, wherein X is greater than or equal to about 2 mol. % and less than or equal to about 10 mol. %; and Y mol. % alkali oxide, wherein the alkali oxide includes from about 0.01 mol. % to about 1.0 mol. % $K_2O$ and a ratio of Y:X is greater than 1, and the glass composition is free of boron and compounds of boron.

In one or more embodiments of any of the above aspects, the pharmaceutical composition includes FORTEO ([rhPTH (1-34]), DULAGLUTIDE (LY2189265), recombinant human insulin glargine, RAMUCIRUMAB (IMC-1121B), SOLANEZUMAB (LY2062430), IXEKUZUMAB (LY2439821), TABALUMAB (LY2127399), NECITUMUMAB (IMC-11F8), or CIXUTUMUMAB (IMC-A12).

In one aspect, the present invention includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8); or CIXUTUMUMAB (IMC-A12) and a pharmaceutically acceptable excipient, such that the pharmaceutical composition is contained within a glass pharmaceutical container including an internal homogeneous layer.

In one or more embodiments, the pharmaceutical container has a compressive stress greater than 150 MPa. In one or more embodiments, the pharmaceutical container has a compressive stress greater than 250 MPa. In one or more embodiments, the pharmaceutical container includes a depth of layer greater than 30 µm. In one or more embodiments, the depth of layer is greater than 35 µm. In one or more embodiments, the pharmaceutical composition demonstrates increased stability, product integrity, or efficacy.

In one aspect, the present invention includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8); or CIXUTUMUMAB (IMC-A12) and a pharmaceutically acceptable excipient, such that the pharmaceutical composition is contained within a glass pharmaceutical container including an internal homogeneous layer having a compressive stress greater than 150 MPa.

In one or more embodiments, the pharmaceutical container includes a depth of layer greater than 10 µm. In one or more embodiments, the pharmaceutical container includes a depth of layer greater than 25 µm. In one or more embodiments, the pharmaceutical container includes a depth of layer greater than 30 µm. In one or more embodiments, the pharmaceutical container has compressive stress greater than 300 MPa. In one or more embodiments, the pharmaceutical container includes increased stability, product integrity, or efficacy.

In another aspect, the present technology includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8), or CIXUTUMUMAB (IMC-A12) and a pharmaceutically acceptable excipient, such that the pharmaceutical composition is contained within a glass pharmaceutical container having a compressive stress greater than 150 MPa and a depth of layer greater than 10 µm, and such that the pharmaceutical composition demonstrates increased stability, product integrity, or efficacy.

In another aspect, the present technology includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8) or CIXUTUMUMAB (IMC-A12) and a pharmaceutically acceptable excipient, such that the pharmaceutical composition is contained within a glass pharmaceutical container including a substantially homogeneous inner layer, and such that the pharmaceutical composition demonstrates increased stability, product integrity, or efficacy.

In another aspect, the present technology includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8); or CIXUTUMUMAB (IMC-A12) and a pharmaceutically acceptable excipient, such that the pharmaceutical composition is contained within a glass pharmaceutical container having a delamination factor of less than 3, wherein the pharmaceutical composition demonstrates increased stability, product integrity, or efficacy.

In another aspect, the present technology includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8) or CIXUTUMUMAB (IMC-A12) and a pharmaceutically acceptable excipient, such that the pharmaceutical composition is contained within a glass pharmaceutical container which is substantially free of boron, and such that the pharmaceutical composition demonstrates increased stability, product integrity, or efficacy.

In one or more embodiments, the glass pharmaceutical container has a compressive stress greater than 150 MPa and a depth of layer greater than 25 µm. In one or more embodiments, the glass pharmaceutical container has a compressive stress greater than 300 MPa and a depth of layer greater than 35 µm. In one or more embodiments, the glass pharmaceutical container includes a substantially homogeneous inner layer. In one or more embodiments, the glass pharmaceutical container has a compressive stress greater than 150 MPa and a depth of layer greater than 25 µm.

In another aspect, the present technology includes a pharmaceutical composition. The pharmaceutical composition includes FORTEO ([rhPTH(1-34]); DULAGLUTIDE (LY2189265); recombinant human insulin glargine; RAMUCIRUMAB (IMC-1121B); SOLANEZUMAB (LY2062430); IXEKUZUMAB (LY2439821); TABALUMAB (LY2127399); NECITUMUMAB (IMC-11F8) or CIXUTUMUMAB (IMC-A12) and a pharmaceutically acceptable excipient, such that the pharmaceutical composition is contained within a glass pharmaceutical container including a delamination factor of less than 3, and such that the pharmaceutical composition includes increased stability, product integrity, or efficacy.

In one or more embodiments of any of the above aspects, the container has a compressive stress greater than 300 MPa. In one or more embodiments, the container has a depth of layer greater than 25 µm. In one or more embodiments, the container has a depth of layer greater than 30 µm. In one or more embodiments, the container has a depth of layer of at least 35 µm. In one or more embodiments, the container has a compressive stress greater than 300 MPa. In one or more embodiments, the container has a compressive stress greater than 350 MPa.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
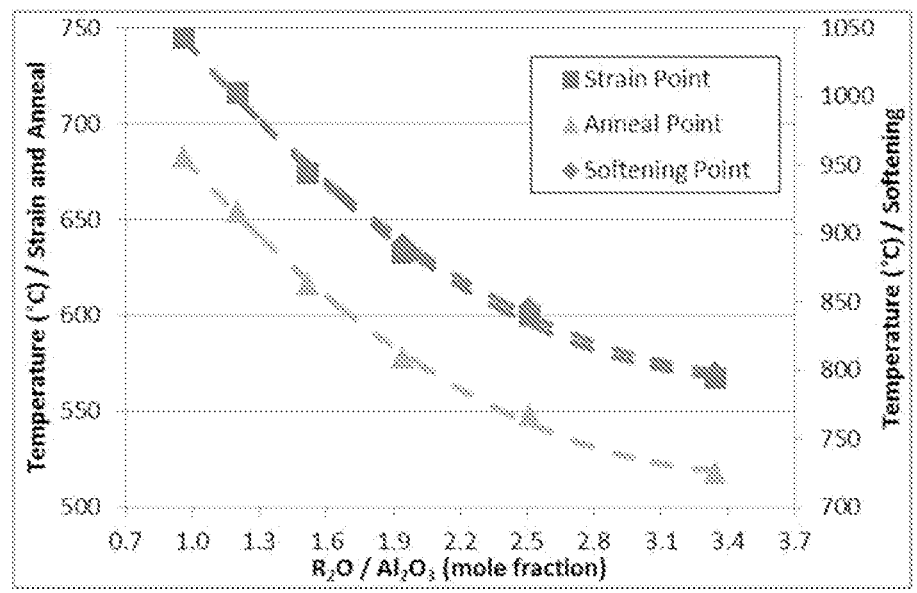
FIG. 1 graphically depicts the relationship between the ratio of alkali oxides to alumina (x-axis) and the strain point, annealing point, and softening point (y-axes) of inventive and comparative glass compositions.

The present invention is based, at least in part, on the identification of a pharmaceutical container formed, at least in part, of a glass composition which exhibits a reduced propensity to delaminate, i.e., a reduced propensity to shed glass particulates. As a result, the presently claimed containers are particularly suited for storage, maintenance and/or delivery of therapeutically efficacious pharmaceutical compositions and, in particular pharmaceutical solutions comprising active pharmaceutical ingredients, for example, FORTEO ([rhPTH(1-34)]), DULAGLUTIDE (LY2189265), recombinant human insulin glargine, RAMUCIRUMAB (IMC-1121B), SOLANEZUMAB (LY2062430), IXEKUZUMAB (LY2439821), TABALUMAB (LY2127399), NECITUMUMAB (IMC-11F8), or CIXUTUMUMAB (IMC-A12).

Conventional glass containers or glass packages for containing pharmaceutical compositions are generally formed from glass compositions which are known to exhibit chemical durability and low thermal expansion, such as alkali borosilicate glasses. While alkali borosilicate glasses exhibit good chemical durability, container manufacturers have sporadically observed silica-rich glass flakes dispersed in the solution contained in the glass containers as a result of delamination, particularly when the solution has been stored in direct contact with the glass surface for long time periods (months to years).

Delamination refers to a phenomenon in which glass particles are released from the surface of the glass following a series of leaching, corrosion, and/or weathering reactions. In general, the glass particles are silica-rich flakes of glass which originate from the interior surface of the package as a result of the leaching of modifier ions into a solution contained within the package. These flakes may generally be from about 1 nm to 2 μm thick with a width greater than about 50 μm.

It has heretofore been hypothesized that delamination is due to the phase separation which occurs in alkali borosilicate glasses when the glass is exposed to the elevated temperatures used for reforming the glass into a container shape.

However, it is now believed that the delamination of the silica-rich glass flakes from the interior surfaces of the glass containers is due to the compositional characteristics of the glass container in its as-formed condition. Specifically, the high silica content of alkali borosilicate glasses increases the melting temperature of the glass. However, the alkali and borate components in the glass composition melt and/or vaporize at much lower temperatures. In particular, the borate species in the glass are highly volatile and evaporate from the surface of the glass at the high temperatures necessary to melt and form the glass.

Specifically, glass stock is reformed into glass containers at high temperatures and in direct flames. The high temperatures cause the volatile borate species to evaporate from portions of the surface of the glass. When this evaporation occurs within the interior volume of the glass container, the volatilized borate species are re-deposited in other areas of the glass causing compositional heterogeneities in the glass container, particularly with respect to the bulk of the glass container. For example, as one end of a glass tube is closed to form the bottom or floor of the container, borate species may evaporate from the bottom portion of the tube and be re-deposited elsewhere in the tube. As a result, the areas of the container exposed to higher temperatures have silica-rich surfaces. Other areas of the container which are amenable to boron deposition may have a silica-rich surface with a boron-rich layer below the surface. Areas amenable to boron deposition are at a temperature greater than the anneal point of the glass composition but less than the hottest temperature the glass is subjected to during reformation when the boron is incorporated into the surface of the glass. Solutions contained in the container may leach the boron from the boron-rich layer. As the boron-rich layer is leached from the glass, the silica-rich surface begins to spall, shedding silica-rich flakes into the solution.

Definitions

The term "softening point," as used herein, refers to the temperature at which the viscosity of the glass composition is $1\times10^{7.6}$ poise.

The term "annealing point," as used herein, refers to the temperature at which the viscosity of the glass composition is $1\times10^{13}$ poise.

The terms "strain point" and "$T_{strain}$" as used herein, refers to the temperature at which the viscosity of the glass composition is $3 \times 10^{14}$ poise.

The term "CTE," as used herein, refers to the coefficient of thermal expansion of the glass composition over a temperature range from about room temperature (RT) to about 300° C.

In the embodiments of the glass compositions described herein, the concentrations of constituent components (e.g., $SiO_2$, $Al_2O_3$, and the like) are specified in mole percent (mol. %) on an oxide basis, unless otherwise specified.

The terms "free" and "substantially free," when used to describe the concentration and/or absence of a particular constituent component in a glass composition, means that the constituent component is not intentionally added to the glass composition. However, the glass composition may contain traces of the constituent component as a contaminant or tramp in amounts of less than 0.01 mol. %.

The term "chemical durability," as used herein, refers to the ability of the glass composition to resist degradation upon exposure to specified chemical conditions. Specifically, the chemical durability of the glass compositions described herein was assessed according to three established material testing standards: DIN 12116 dated March 2001 and entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; and ISO 720: 1985 entitled "Glass—Hydrolytic resistance of glass grains at 121 degrees C. —Method of test and classification." The chemical durability of the glass may also be assessed according to ISO 719:1985 "Glass—Hydrolytic resistance of glass grains at 98 degrees C. —Method of test and classification," in addition to the above referenced standards. The ISO 719 standard is a less rigorous version of the ISO 720 standard and, as such, it is believed that a glass which meets a specified classification of the ISO 720 standard will also meet the corresponding classification of the ISO 719 standard. The classifications associated with each standard are described in further detail herein.

Glass Compositions

Reference will now be made in detail to various embodiments of pharmaceutical containers formed, at least in part, of glass compositions which exhibit improved chemical and mechanical durability and, in particular, improved resistance to delamination. The glass compositions may also be chemically strengthened thereby imparting increased mechanical durability to the glass. The glass compositions described herein generally comprise silica ($SiO_2$), alumina ($Al_2O_3$), alkaline earth oxides (such as MgO and/or CaO), and alkali oxides (such as $Na_2O$ and/or $K_2O$) in amounts which impart chemical durability to the glass composition. Moreover, the alkali oxides present in the glass compositions facilitate chemically strengthening the glass compositions by ion exchange. Various embodiments of the glass compositions will be described herein and further illustrated with reference to specific examples.

The glass compositions described herein are alkali aluminosilicate glass compositions which generally include a combination of $SiO_2$, $Al_2O_3$, at least one alkaline earth oxide, and one or more alkali oxides, such as $Na_2O$ and/or $K_2O$. In some embodiments, the glass compositions may be free from boron and compounds containing boron. The combination of these components enables a glass composition which is resistant to chemical degradation and is also suitable for chemical strengthening by ion exchange. In some embodiments the glass compositions may further comprise minor amounts of one or more additional oxides such as, for example, $SnO_2$, $ZrO_2$, ZnO, $TiO_2$, $As_2O_3$ or the like. These components may be added as fining agents and/or to further enhance the chemical durability of the glass composition.

In the embodiments of the glass compositions described herein $SiO_2$ is the largest constituent of the composition and, as such, is the primary constituent of the resulting glass network. $SiO_2$ enhances the chemical durability of the glass and, in particular, the resistance of the glass composition to decomposition in acid and the resistance of the glass composition to decomposition in water. Accordingly, a high $SiO_2$ concentration is generally desired. However, if the content of $SiO_2$ is too high, the formability of the glass may be diminished as higher concentrations of $SiO_2$ increase the difficulty of melting the glass which, in turn, adversely impacts the formability of the glass. In the embodiments described herein, the glass composition generally comprises $SiO_2$ in an amount greater than or equal to 67 mol. % and less than or equal to about 80 mol. % or even less than or equal to 78 mol. %. In some embodiments, the amount of $SiO_2$ in the glass composition may be greater than about 68 mol. %, greater than about 69 mol. % or even greater than about 70 mol. %. In some other embodiments, the amount of $SiO_2$ in the glass composition may be greater than 72 mol. %, greater than 73 mol. % or even greater than 74 mol. %. For example, in some embodiments, the glass composition may include from about 68 mol. % to about 80 mol. % or even to about 78 mol. % $SiO_2$. In some other embodiments the glass composition may include from about 69 mol. % to about 80 mol. % or even to about 78 mol. % $SiO_2$. In some other embodiments the glass composition may include from about 70 mol. % to about 80 mol. % or even to about 78 mol. % $SiO_2$. In still other embodiments, the glass composition comprises $SiO_2$ in an amount greater than or equal to 70 mol. % and less than or equal to 78 mol. %. In some embodiments, $SiO_2$ may be present in the glass composition in an amount from about 72 mol. % to about 78 mol. %. In some other embodiments, $SiO_2$ may be present in the glass composition in an amount from about 73 mol. % to about 78 mol. %. In other embodiments, $SiO_2$ may be present in the glass composition in an amount from about 74 mol. % to about 78 mol. %. In still other embodiments, $SiO_2$ may be present in the glass composition in an amount from about 70 mol. % to about 76 mol. %.

The glass compositions described herein further include $Al_2O_3$. $Al_2O_3$, in conjunction with alkali oxides present in the glass compositions such as $Na_2O$ or the like, improves the susceptibility of the glass to ion exchange strengthening. In the embodiments described herein, $Al_2O_3$ is present in the glass compositions in X mol. % while the alkali oxides are present in the glass composition in Y mol. %. The ratio Y:X in the glass compositions described herein is greater than 1 in order to facilitate the aforementioned susceptibility to ion exchange strengthening. Specifically, the diffusion coefficient or diffusivity D of the glass composition relates to the rate at which alkali ions penetrate into the glass surface during ion exchange. Glasses which have a ratio Y:X greater than about 0.9 or even greater than about 1 have a greater diffusivity than glasses which have a ratio Y:X less than 0.9. Glasses in which the alkali ions have a greater diffusivity can obtain a greater depth of layer for a given ion exchange time and ion exchange temperature than glasses in which the alkali ions have a lower diffusivity. Moreover, as the ratio of Y:X increases, the strain point, anneal point, and softening point of the glass decrease, such that the glass is more readily formable. In addition, for a given ion exchange time and ion exchange temperature, it has been found that compressive stresses induced in glasses which have a ratio Y:X greater than about 0.9 and less than or equal to 2 are generally greater than those generated in glasses in which the ratio Y:X is less than 0.9 or greater than 2. Accordingly, in some embodiments, the ratio of Y:X is greater than 0.9 or even greater than 1. In some embodiments, the ratio of Y:X is greater than 0.9, or even greater than 1, and less than or equal to about 2. In still other embodiments, the ratio of Y:X may be greater than or equal to about 1.3 and less than or equal to about 2.0 in order to maximize the amount of compressive stress induced in the glass for a specified ion exchange time and a specified ion exchange temperature.

However, if the amount of $Al_2O_3$ in the glass composition is too high, the resistance of the glass composition to acid attack is diminished. Accordingly, the glass compositions described herein generally include $Al_2O_3$ in an amount greater than or equal to about 2 mol. % and less than or equal to about 10 mol. %. In some embodiments, the amount of $Al_2O_3$ in the glass composition is greater than or equal to about 4 mol. % and less than or equal to about 8 mol. %. In some other embodiments, the amount of $Al_2O_3$ in the glass composition is greater than or equal to about 5 mol. % to less than or equal to about 7 mol. %. In some other embodiments, the amount of $Al_2O_3$ in the glass composition is greater than or equal to about 6 mol. % to less than or equal to about 8 mol. %. In still other embodiments, the amount of $Al_2O_3$ in the glass composition is greater than or equal to about 5 mol. % to less than or equal to about 6 mol. %.

The glass compositions also include one or more alkali oxides such as $Na_2O$ and/or $K_2O$. The alkali oxides facilitate the ion exchangeability of the glass composition and, as such, facilitate chemically strengthening the glass. The alkali oxide may include one or more of $Na_2O$ and $K_2O$. The alkali oxides are generally present in the glass composition in a total concentration of Y mol. %. In some embodiments described herein, Y may be greater than about 2 mol. % and less than or equal to about 18 mol. %. In some other embodiments, Y may be greater than about 8 mol. %, greater than about 9 mol. %, greater than about 10 mol. % or even greater than about 11 mol. %. For example, in some embodiments described herein Y is greater than or equal to about 8 mol. % and less than or equal to about 18 mol. %. In still other embodiments, Y may be greater than or equal to about 9 mol. % and less than or equal to about 14 mol. %.

The ion exchangeability of the glass composition is primarily imparted to the glass composition by the amount of the alkali oxide $Na_2O$ initially present in the glass composition prior to ion exchange. Accordingly, in the embodiments of the glass compositions described herein, the alkali oxide present in the glass composition includes at least $Na_2O$. Specifically, in order to achieve the desired compressive strength and depth of layer in the glass composition upon ion exchange strengthening, the glass compositions include $Na_2O$ in an amount from about 2 mol. % to about 15 mol. % based on the molecular weight of the glass composition. In some embodiments the glass composition includes at least about 8 mol. % of $Na_2O$ based on the molecular weight of the glass composition. For example, the concentration of $Na_2O$ may be greater than 9 mol. %, greater than 10 mol. % or even greater than 11 mol. %. In some embodiments, the concentration of $Na_2O$ may be greater than or equal to 9 mol. % or even greater than or equal to 10 mol. %. For example, in some embodiments the glass composition may include $Na_2O$ in an amount greater than or equal to about 9 mol. % and less than or equal to about 15 mol. % or even greater than or equal to about 9 mol. % and less than or equal to 13 mol. %.

As noted above, the alkali oxide in the glass composition may further include $K_2O$. The amount of $K_2O$ present in the glass composition also relates to the ion exchangeability of the glass composition. Specifically, as the amount of $K_2O$ present in the glass composition increases, the compressive stress obtainable through ion exchange decreases as a result of the exchange of potassium and sodium ions. Accordingly, it is desirable to limit the amount of $K_2O$ present in the glass composition. In some embodiments, the amount of $K_2O$ is greater than or equal to 0 mol. % and less than or equal to 3 mol. %. In some embodiments, the amount of $K_2O$ is less or equal to 2 mol. % or even less than or equal to 1.0 mol. %. In embodiments where the glass composition includes $K_2O$, the $K_2O$ may be present in a concentration greater than or equal to about 0.01 mol. % and less than or equal to about 3.0 mol. % or even greater than or equal to about 0.01 mol. % and less than or equal to about 2.0 mol. %. In some embodiments, the amount of $K_2O$ present in the glass composition is greater than or equal to about 0.01 mol. % and less than or equal to about 1.0 mol. %. Accordingly, it should be understood that $K_2O$ need not be present in the glass composition. However, when $K_2O$ is included in the glass composition, the amount of $K_2O$ is generally less than about 3 mol. % based on the molecular weight of the glass composition.

The alkaline earth oxides present in the composition improve the meltability of the glass batch materials and increase the chemical durability of the glass composition. In the glass compositions described herein, the total mol. % of alkaline earth oxides present in the glass compositions is generally less than the total mol. % of alkali oxides present in the glass compositions in order to improve the ion exchangeability of the glass composition. In the embodiments described herein, the glass compositions generally include from about 3 mol. % to about 13 mol. % of alkaline earth oxide. In some of these embodiments, the amount of alkaline earth oxide in the glass composition may be from about 4 mol. % to about 8 mol. % or even from about 4 mol. % to about 7 mol. %.

The alkaline earth oxide in the glass composition may include MgO, CaO, SrO, BaO or combinations thereof. In some embodiments, the alkaline earth oxide includes MgO, CaO or combinations thereof. For example, in the embodiments described herein the alkaline earth oxide includes MgO. MgO is present in the glass composition in an amount which is greater than or equal to about 3 mol. % and less than or equal to about 8 mol. % MgO. In some embodiments, MgO may be present in the glass composition in an amount which is greater than or equal to about 3 mol. % and less than or equal to about 7 mol. % or even greater than or equal to 4 mol. % and less than or equal to about 7 mol. % by molecular weight of the glass composition.

In some embodiments, the alkaline earth oxide may further include CaO. In these embodiments CaO is present in the glass composition in an amount from about 0 mol. % to less than or equal to 6 mol. % by molecular weight of the glass composition. For example, the amount of CaO present in the glass composition may be less than or equal to 5 mol. %, less than or equal to 4 mol. %, less than or equal to 3 mol. %, or even less than or equal to 2 mol. %. In some of these embodiments, CaO may be present in the glass composition in an amount greater than or equal to 0.1 mol. % and less than or equal to about 1.0 mol. %. For example, CaO may be present in the glass composition in an amount greater than or equal to about 0.2 mol. % and less than or equal to about 0.7 mol. % or even in an amount greater than or equal to about 0.3 mol. % and less than or equal to about 0.6 mol. %.

In the embodiments described herein, the glass compositions are generally rich in MgO, (i.e., the concentration of MgO in the glass composition is greater than the concentration of the other alkaline earth oxides in the glass composition including, without limitation, CaO). Forming the glass composition such that the glass composition is MgO-rich improves the hydrolytic resistance of the resultant glass, particularly following ion exchange strengthening. Moreover, glass compositions which are MgO-rich generally exhibit improved ion exchange performance relative to glass compositions which are rich in other alkaline earth oxides. Specifically, glasses formed from MgO-rich glass compositions generally have a greater diffusivity than glass compositions which are rich in other alkaline earth oxides, such as CaO. The greater diffusivity enables the formation of a deeper depth of layer in the glass. MgO-rich glass compositions also enable a higher compressive stress to be achieved in the surface of the glass compared to glass compositions which are rich in other alkaline earth oxides such as CaO. In addition, it is generally understood that as the ion exchange process proceeds and alkali ions penetrate more deeply into the glass, the maximum compressive stress achieved at the surface of the glass may decrease with time. However, glasses formed from glass compositions which are MgO-rich exhibit a lower reduction in compressive stress than glasses formed from glass compositions that are CaO-rich or rich in other alkaline earth oxides (i.e., glasses which are MgO-poor). Thus, MgO-rich glass compositions enable glasses which have higher compressive stress at the surface and greater depths of layer than glasses which are rich in other alkaline earth oxides.

In order to fully realize the benefits of MgO in the glass compositions described herein, it has been determined that the ratio of the concentration of CaO to the sum of the concentration of CaO and the concentration of MgO in mol. % (i.e., (CaO/(CaO+MgO)) should be minimized. Specifically, it has been determined that (CaO/(CaO+MgO)) should be less than or equal to 0.5. In some embodiments (CaO/(CaO+MgO)) is less than or equal to 0.3 or even less than or equal to 0.2. In some other embodiments (CaO/(CaO+MgO)) may even be less than or equal to 0.1.

Boron oxide ($B_2O_3$) is a flux which may be added to glass compositions to reduce the viscosity at a given temperature (e.g., the strain, anneal and softening temperatures) thereby improving the formability of the glass. However, it has been found that additions of boron significantly decrease the diffusivity of sodium and potassium ions in the glass composition which, in turn, adversely impacts the ion exchange performance of the resultant glass. In particular, it has been found that additions of boron significantly increase the time required to achieve a given depth of layer relative to glass compositions which are boron free. Accordingly, in some embodiments described herein, the amount of boron added to the glass composition is minimized in order to improve the ion exchange performance of the glass composition.

For example, it has been determined that the impact of boron on the ion exchange performance of a glass composition can be mitigated by controlling the ratio of the concentration of $B_2O_3$ to the difference between the total concentration of the alkali oxides (i.e., $R_2O$, where R is the alkali metals) and alumina (i.e., $B_2O_3$ (mol. %)/($R_2O$ (mol. %)-$Al_2O_3$ (mol. %)). In particular, it has been determined that when the ratio of $B_2O_3/(R_2O—Al_2O_3)$ is greater than or equal to about 0 and less than about 0.3 or even less than about 0.2, the diffusivities of alkali oxides in the glass compositions are not diminished and, as such, the ion exchange performance of the glass composition is maintained. Accordingly, in some embodiments, the ratio of $B_2O_3/(R_2O—Al_2O_3)$ is greater than 0 and less than or equal to 0.3. In some of these embodiments, the ratio of $B_2O_3/(R_2O—Al_2O_3)$ is greater than 0 and less than or equal to 0.2. In some embodiments, the ratio of $B_2O_3/(R_2O—Al_2O_3)$ is greater than 0 and less than or equal to 0.15 or even less than or equal to 0.1. In some other embodiments, the ratio of $B_2O_3/(R_2O—Al_2O_3)$ may be greater than 0 and less than or equal to 0.05. Maintaining the ratio $B_2O_3/(R_2O—Al_2O_3)$ to be less than or equal to 0.3 or even less than or equal to 0.2 permits the inclusion of $B_2O_3$ to lower the strain point, anneal point and softening point of the glass composition without the $B_2O_3$ adversely impacting the ion exchange performance of the glass.

In the embodiments described herein, the concentration of $B_2O_3$ in the glass composition is generally less than or equal to about 4 mol. %, less than or equal to about 3 mol. %, less than or equal to about 2 mol. %, or even less than or equal to 1 mol. %. For example, in embodiments where $B_2O_3$ is present in the glass composition, the concentration of $B_2O_3$ may be greater than about 0.01 mol. % and less than or equal to 4 mol. %. In some of these embodiments, the concentration of $B_2O_3$ may be greater than about 0.01 mol. % and less than or equal to 3 mol. % In some embodiments, the $B_2O_3$ may be present in an amount greater than or equal to about 0.01 mol. % and less than or equal to 2 mol. %, or even less than or equal to 1.5 mol. %. Alternatively, the $B_2O_3$ may be present in an amount greater than or equal to about 1 mol. % and less than or equal to 4 mol. %, greater than or equal to about 1 mol. % and less than or equal to 3 mol. % or even greater than or equal to about 1 mol. % and less than or equal to 2 mol. %. In some of these embodiments, the concentration of $B_2O_3$ may be greater than or equal to about 0.1 mol. % and less than or equal to 1.0 mol. %.

While in some embodiments the concentration of $B_2O_3$ in the glass composition is minimized to improve the forming properties of the glass without detracting from the ion exchange performance of the glass, in some other embodiments the glass compositions are free from boron and compounds of boron such as $B_2O_3$. Specifically, it has been determined that forming the glass composition without boron or compounds of boron improves the ion exchangeability of the glass compositions by reducing the process time and/or temperature required to achieve a specific value of compressive stress and/or depth of layer.

In some embodiments of the glass compositions described herein, the glass compositions are free from phosphorous and compounds containing phosphorous including, without limitation, $P_2O_5$. Specifically, it has been determined that formulating the glass composition without phosphorous or compounds of phosphorous increases the chemical durability of the glass composition.

In addition to the $SiO_2$, $Al_2O_3$, alkali oxides and alkaline earth oxides, the glass compositions described herein may optionally further comprise one or more fining agents such as, for example, $SnO_2$, $As_2O_3$, and/or $Cl^-$ (from NaCl or the like). When a fining agent is present in the glass composition, the fining agent may be present in an amount less than or equal to about 1 mol. % or even less than or equal to about 0.4 mol. %. For example, in some embodiments the glass composition may include $SnO_2$ as a fining agent. In these embodiments $SnO_2$ may be present in the glass composition in an amount greater than about 0 mol. % and less than or equal to about 1 mol. % or even an amount greater than or equal to about 0.01 mol. % and less than or equal to about 0.30 mol. %.

Moreover, the glass compositions described herein may comprise one or more additional metal oxides to further improve the chemical durability of the glass composition. For example, the glass composition may further include $ZnO$, $TiO_2$, or $ZrO_2$, each of which further improves the resistance of the glass composition to chemical attack. In these embodiments, the additional metal oxide may be present in an amount which is greater than or equal to about 0 mol. % and less than or equal to about 2 mol. %. For example, when the additional metal oxide is $ZnO$, the $ZnO$ may be present in an amount greater than or equal to 1 mol. % and less than or equal to about 2 mol. %. When the additional metal oxide is $ZrO_2$ or $TiO_2$, the $ZrO_2$ or $TiO_2$ may be present in an amount less than or equal to about 1 mol. %.

Based on the foregoing, it should be understood that, in a first exemplary embodiment, a glass composition may include: $SiO_2$ in a concentration greater than about 70 mol. % and Y mol. % alkali oxide. The alkali oxide may include $Na_2O$ in an amount greater than about 8 mol. %. The glass composition may be free of boron and compounds of boron. The concentration of $SiO_2$ in this glass composition may be greater than or equal to about 72 mol. %, greater than 73 mol. % or even greater than 74 mol. %. The glass composition of this first exemplary embodiment may be free from phosphorous and compounds of phosphorous. The glass composition may also include X mol. % $Al_2O_3$. When $Al_2O_3$ is included, the ratio of Y:X may be greater than 1. The concentration of $Al_2O_3$ may be greater than or equal to about 2 mol. % and less than or equal to about 10 mol. %.

The glass composition of this first exemplary embodiment may also include alkaline earth oxide in an amount from about 3 mol. % to about 13 mol. %. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

In a second exemplary embodiment, a glass composition may include: greater than about 68 mol. % $SiO_2$; X mol. % $Al_2O_3$; Y mol. % alkali oxide; and $B_2O_3$. The alkali oxide may include $Na_2O$ in an amount greater than about 8 mol %. A ratio ($B_2O_3$ (mol. %)/(Y mol. %–X mol. %) may be greater than 0 and less than 0.3. The concentration of $SiO_2$ in this glass composition may be greater than or equal to about 72 mol. %, greater than 73 mol. % or even greater than 74 mol. %. The concentration of $Al_2O_3$ may be greater than or equal to about 2 mol. % and less than or equal to about 10 mol. %. In this second exemplary embodiment, the ratio of Y:X may be greater than 1. When the ratio of Y:X is greater than 1, an upper bound of the ratio of Y:X may be less than or equal to 2. The glass composition of this first exemplary embodiment may be free from phosphorous and compounds of phosphorous.

The glass composition of this second exemplary embodiment may also include alkaline earth oxide. The alkaline earth oxide may include MgO and CaO. The CaO may be present in an amount greater than or equal to about 0.1 mol. % and less than or equal to about 1.0 mol. %. A ratio (CaO (mol. %)/(CaO (mol. %)+MgO (mol. %))) may be less than or equal to 0.5.

The concentration of $B_2O_3$ in this second exemplary embodiment may be greater than or equal to about 0.01 mol. % and less than or equal to about 4 mol. %.

In a third exemplary embodiment, a glass article may have a type HgB1 hydrolytic resistance according to ISO 719. The glass article may include greater than about 8 mol. % $Na_2O$ and less than about 4 mol. % $B_2O_3$. The glass article may further comprise X mol. % $Al_2O_3$ and Y mol. % alkali oxide. The ratio ($B_2O_3$ (mol. %)/(Y mol. %–X mol. %) may be greater than 0 and less than 0.3. The glass article of this third exemplary embodiment may further include a compressive stress layer having a surface compressive stress greater than or equal to about 250 MPa. The glass article may also have at least a class S3 acid resistance according to DIN 12116; at least a class A2 base resistance according to ISO 695; and a type HgA1 hydrolytic resistance according to ISO 720.

In a fourth exemplary embodiment, a glass pharmaceutical package may include $SiO_2$ in an amount greater than about 70 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. The glass pharmaceutical package may also have a type HGB1 hydrolytic resistance according to ISO 719. The concentration of $SiO_2$ in the glass pharmaceutical package of this fourth exemplary embodiment may be greater than or equal to 72 mol. % and less than or equal to about 78 mol. % or even greater than 74 mol. % and less than or equal to about 78 mol. %. The concentration of $Al_2O_3$ in the glass pharmaceutical may be greater than or equal to about 4 mol. % and less than or equal to about 8 mol. %. A ratio of Y:X may be greater than 1 and less than 2.

The glass pharmaceutical package of this fourth exemplary embodiment may also include alkaline earth oxide in an amount from about 4 mol. % to about 8 mol. %. The alkaline earth oxide may include MgO and CaO. The CaO may be present in an amount greater than or equal to about 0.2 mol. % and less than or equal to about 0.7 mol. %. A ratio (CaO (mol. %)/(CaO (mol. %)+MgO (mol. %))) may be less than or equal to 0.5. The glass pharmaceutical package of this fourth exemplary embodiment may have a type HGA1 hydrolytic resistance according to ISO 720.

In a fifth exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. A ratio of Y:X may be greater than 1. The glass composition may be free of boron and compounds of boron.

In a sixth exemplary embodiment, a glass composition may include from about 68 mol. % to about 80 mol. % $SiO_2$; from about 3 mol. % to about 13 mol. % alkaline earth oxide; X mol. % $Al_2O_3$; and Y mol. % alkali oxide. The alkali oxide may include $Na_2O$ in an amount greater than about 8 mol. %. The glass composition of this sixth exemplary embodiment may also include $B_2O_3$. A ratio ($B_2O_3$ (mol. %)/(Y mol. %–X mol. %) may be greater than 0 and less than 0.3. A ratio of Y:X may be greater than 1.

In a seventh exemplary embodiment, a glass composition may include from about 70 mol. % to about 80 mol. % $SiO_2$; from about 3 mol. % to about 13 mol. % alkaline earth oxide; X mol. % $Al_2O_3$; and Y mol. % alkali oxide. The amount of $Al_2O_3$ in the glass composition may be greater than or equal to about 2 mol. % and less than or equal to about 10 mol. %. The alkaline earth oxide may include CaO in an amount greater than or equal to about 0.1 mol. % and less than or equal to about 1.0 mol. %. The alkali oxide may include from about 0.01 mol. % to about 1.0 mol. % $K_2O$. A ratio of Y:X may be greater than 1. The glass composition may be free of boron and compounds of boron. The glass composition may be amenable to strengthening by ion exchange.

In a seventh exemplary embodiment, a glass composition may include $SiO_2$ in an amount greater than about 70 mol. % and less than or equal to about 80 mol. %; X mol. % $Al_2O_3$; and Y mol. % alkali oxide. The alkali oxide may include $Na_2O$ in an amount greater than about 8 mol. %. A ratio of a concentration of $B_2O_3$ (mol. %) in the glass pharmaceutical package to (Y mol. %–X mol. %) may be less than 0.3. A ratio of Y:X may be greater than 1.

In an eighth exemplary embodiment, a glass composition may include from about 72 mol. % to about 78 mol. % $SiO_2$; from about 4 mol. % to about 8 mol. % alkaline earth oxide; X mol. % $Al_2O_3$, wherein X is greater than or equal to about 4 mol. % and less than or equal to about 8 mol. %.; and Y mol. % alkali oxide, wherein the alkali oxide comprises $Na_2O$ in an amount greater than or equal to about 9 mol. % and less than or equal to about 15 mol. %. A ratio of a concentration of $B_2O_3$ (mol. %) in the glass pharmaceutical package to (Y mol. %–X mol. %) is less than 0.3. A ratio of Y:X may be greater than 1.

In a ninth exemplary embodiment, a pharmaceutical package for containing a pharmaceutical composition may include from about 70 mol. % to about 78 mol. % $SiO_2$; from about 3 mol. % to about 13 mol. % alkaline earth oxide; X mol. % $Al_2O_3$, wherein X is greater than or equal to 2 mol. % and less than or equal to about 10 mol. %; and Y mol. % alkali oxide, wherein the alkali oxide comprises $Na_2O$ in an amount greater than about 8 mol. %. The alkaline earth oxide may include CaO in an amount less than or equal to about 6.0 mol. %. A ratio of Y:X may be greater than about 1. The package may be free of boron and compounds of boron and may include a compressive stress layer with a compressive stress greater than or equal to about 250 MPa and a depth of layer greater than or equal to about 10 μm.

In a tenth exemplary embodiment, a glass article may be formed from a glass composition comprising from about 70 mol. % to about 78 mol. % $SiO_2$; alkaline earth oxide, wherein the alkaline earth oxide comprises MgO and CaO and a ratio (CaO (mol. %)/(CaO (mol. %)+MgO (mol. %))) is less than or equal to 0.5; X mol. % $Al_2O_3$, wherein X is from about 2 mol. % to about 10 mol. %; and Y mol. % alkali oxide, wherein the alkali oxide comprises $Na_2O$ in an amount greater than about 8 mol. % and a ratio of Y:X is greater than 1. The glass article may be ion exchange strengthened with a compressive stress greater than or equal to 250 MPa and a depth of layer greater than or equal to 10 μm. The glass article may have a type HgA1 hydrolytic resistance according to ISO 720.

As noted above, the presence of alkali oxides in the glass composition facilitates chemically strengthening the glass by ion exchange. Specifically, alkali ions, such as potassium ions, sodium ions and the like, are sufficiently mobile in the glass to facilitate ion exchange. In some embodiments, the glass composition is ion exchangeable to form a compressive stress layer having a depth of layer greater than or equal to 10 μm. In some embodiments, the depth of layer may be greater than or equal to about 25 μm or even greater than or equal to about 50 μm. In some other embodiments, the depth of the layer may be greater than or equal to 75 μm or even greater than or equal to 100 μm. In still other embodiments, the depth of layer may be greater than or equal to 10 μm and less than or equal to about 100 μm. The associated surface compressive stress may be greater than or equal to about 250 MPa, greater than or equal to 300 MPa or even greater than or equal to about 350 MPa after the glass composition is treated in a salt bath of 100% molten $KNO_3$ at a temperature of 350° C. to 500° C. for a time period of less than about 30 hours or even about less than 20 hours.

The glass articles formed from the glass compositions described herein may have a hydrolytic resistance of HGB2 or even HGB1 under ISO 719 and/or a hydrolytic resistance of HGA2 or even HGA1 under ISO 720 (as described further herein) in addition to having improved mechanical characteristics due to ion exchange strengthening. In some embodiments described herein the glass articles may have compressive stresses which extend from the surface into the glass article to a depth of layer greater than or equal to 10 μm, greater than or equal to 15 μm, greater than or equal to 20 μm, greater than or equal to 25 μm, greater than or equal to 30 μm or even greater than or equal to 35 μm. In some embodiments, the depth of layer may be greater than or equal to 40 μm or even greater than or equal to 50 μm. The surface compressive stress of the glass article may be greater than or equal to 150 MPa, greater than or equal to 200 MPa, greater than or equal to 250 MPa, greater than or equal to 350 MPa, or even greater than or equal to 400 MPa.

In one embodiment, the glass pharmaceutical container has a compressive stress greater than or equal to 150 MPa and a depth of layer greater than or equal to 10 μm, 15 μm, 20 μm, 25 μm, 30 μm, 35 μm, 40 μm, 45 μm or 50 μm. In a particular embodiment, the glass pharmaceutical container has a compressive stress greater than or equal to 150 MPa and a depth of layer greater than or equal to 10 μm. In a particular embodiment, the glass pharmaceutical container has a compressive stress greater than or equal to 150 MPa and a depth of layer greater than or equal to 25 μm. In a particular embodiment, the glass pharmaceutical container has a compressive stress greater than or equal to 150 MPa and a depth of layer greater than or equal to 30 μm.

In one embodiment, the glass pharmaceutical container has a compressive stress greater than or equal to 300 MPa and a depth of layer greater than or equal to 10 μm, 15 μm, 20 μm, 25 μm, 30 μm, 35 μm, 40 μm, 45 μm or 50 μm. In a particular embodiment, the glass pharmaceutical container has a compressive stress greater than or equal to 300 MPa and a depth of layer greater than or equal to 25 μm. In yet another embodiment, the glass pharmaceutical container has a compressive stress greater than or equal to 300 MPa and a depth of layer greater than or equal to 30 μm. In yet another embodiment, the glass pharmaceutical container has a compressive stress greater than or equal to 300 MPa and a depth of layer greater than or equal to 35 μm.

The glass compositions described herein facilitate achieving the aforementioned depths of layer and surface compressive stresses more rapidly and/or at lower temperatures than conventional glass compositions due to the enhanced alkali ion diffusivity of the glass compositions as described hereinabove. For example, the depths of layer (i.e., greater than or equal to 25 μm) and the compressive stresses (i.e., greater than or equal to 250 MPa) may be achieved by ion exchanging the glass article in a molten salt bath of 100% $KNO_3$ (or a mixed salt bath of $KNO_3$ and $NaNO_3$) for a time period of less than or equal to 5 hours or even less than or equal to 4.5 hours. In some embodiments, these depths of layer and compressive stresses may be achieved by ion exchanging the glass article in a molten salt bath of 100% $KNO_3$ (or a mixed salt bath of $KNO_3$ and $NaNO_3$) for a time period of less than or equal to 4 hours or even less than or equal to 3.5 hours. Moreover, these depths of layers and compressive stresses may be achieved by ion exchanging the glass articles in a molten salt bath of 100% KNO3 (or a mixed salt bath of $KNO_3$ and $NaNO_3$) at a temperature less than or equal to 500° C. or even less than or equal to 450° C. In some embodiments, these depths of layers and compressive stresses may be achieved by ion exchanging the glass articles in a molten salt bath of 100% KNO3 (or a mixed salt bath of $KNO_3$ and $NaNO_3$) at a temperature less than or equal to 400° C. or even less than or equal to 350° C.

These improved ion exchange characteristics can be achieved when the glass composition has a threshold diffusivity of greater than about 16 $\mu m^2$/hr or even greater than or equal to 20 $\mu m^2$/hr at 450° C. In some embodiments, the threshold diffusivity may be greater than or equal to about 25 $\mu m^2$/hr or even 30 $\mu m^2$/hr at 450° C. In some other embodiments, the threshold diffusivity may be greater than or equal to about 35 $\mu m^2$/hr or even 40 $\mu m^2$/hr at 450° C. In still other embodiments, the threshold diffusivity may be greater than or equal to about 45 $\mu m^2$/hr or even 50 $\mu m^2$/hr at 450° C.

The glass compositions described herein may generally have a strain point greater than or equal to about 525° C. and less than or equal to about 650° C. The glasses may also have an anneal point greater than or equal to about 560° C. and less than or equal to about 725° C. and a softening point greater than or equal to about 750° C. and less than or equal to about 960° C.

In the embodiments described herein the glass compositions have a CTE of less than about $70 \times 10^{-7} K^{-1}$ or even less than about $60 \times 10^{-7} K^{-1}$. These lower CTE values improve the survivability of the glass to thermal cycling or thermal stress conditions relative to glass compositions with higher CTEs.

Further, as noted hereinabove, the glass compositions are chemically durable and resistant to degradation as determined by the DIN 12116 standard, the ISO 695 standard, and the ISO 720 standard.

Specifically, the DIN 12116 standard is a measure of the resistance of the glass to decomposition when placed in an acidic solution. In brief, the DIN 12116 standard utilizes a polished glass sample of a known surface area which is weighed and then positioned in contact with a proportional amount of boiling 6M hydrochloric acid for 6 hours. The sample is then removed from the solution, dried and weighed again. The glass mass lost during exposure to the acidic solution is a measure of the acid durability of the sample with smaller numbers indicative of greater durability. The results of the test are reported in units of half-mass per surface area, specifically $mg/dm^2$. The DIN 12116 standard is broken into individual classes. Class S1 indicates weight losses of up to 0.7 $mg/dm^2$; Class S2 indicates weight losses from 0.7 $mg/dm^2$ up to 1.5 $mg/dm^2$; Class S3 indicates weight losses from 1.5 $mg/dm^2$ up to 15 $mg/dm^2$; and Class S4 indicates weight losses of more than 15 $mg/dm^2$.

The ISO 695 standard is a measure of the resistance of the glass to decomposition when placed in a basic solution. In brief, the ISO 695 standard utilizes a polished glass sample which is weighed and then placed in a solution of boiling 1M NaOH+0.5M $Na_2CO_3$ for 3 hours. The sample is then removed from the solution, dried and weighed again. The glass mass lost during exposure to the basic solution is a measure of the base durability of the sample with smaller numbers indicative of greater durability. As with the DIN 12116 standard, the results of the ISO 695 standard are reported in units of mass per surface area, specifically $mg/dm^2$. The ISO 695 standard is broken into individual classes. Class A1 indicates weight losses of up to 75 $mg/dm^2$; Class A2 indicates weight losses from 75 $mg/dm^2$ up to 175 $mg/dm^2$; and Class A3 indicates weight losses of more than 175 $mg/dm^2$.

The ISO 720 standard is a measure of the resistance of the glass to degradation in purified, $CO_2$-free water. In brief, the ISO 720 standard protocol utilizes crushed glass grains which are placed in contact with the purified, $CO_2$-free water under autoclave conditions (121° C., 2 atm) for 30 minutes. The solution is then titrated colorimetrically with dilute HCl to neutral pH. The amount of HCl required to titrate to a neutral solution is then converted to an equivalent of $Na_2O$ extracted from the glass and reported in μg $Na_2O$ per weight of glass with smaller values indicative of greater durability. The ISO 720 standard is broken into individual types. Type HGA1 is indicative of up to 62 μg extracted equivalent of $Na_2O$ per gram of glass tested; Type HGA2 is indicative of more than 62 μg and up to 527 μg extracted equivalent of $Na_2O$ per gram of glass tested; and Type HGA3 is indicative of more than 527 μg and up to 930 μg extracted equivalent of $Na_2O$ per gram of glass tested.

The ISO 719 standard is a measure of the resistance of the glass to degradation in purified, $CO_2$-free water. In brief, the ISO 719 standard protocol utilizes crushed glass grains which are placed in contact with the purified, $CO_2$-free water at a temperature of 98° C. at 1 atmosphere for 30 minutes. The solution is then titrated colorimetrically with dilute HCl to neutral pH. The amount of HCl required to titrate to a neutral solution is then converted to an equivalent of $Na_2O$ extracted from the glass and reported in μg $Na_2O$ per weight of glass with smaller values indicative of greater durability. The ISO 719 standard is broken into individual types. The ISO 719 standard is broken into individual types. Type HGB1 is indicative of up to 31 μg extracted equivalent of $Na_2O$; Type HGB2 is indicative of more than 31 μg and up to 62 μg extracted equivalent of $Na_2O$; Type HGB3 is indicative of more than 62 μg and up to 264 μg extracted equivalent of $Na_2O$; Type HGB4 is indicative of more than 264 μg and up to 620 μg extracted equivalent of $Na_2O$; and Type HGB5 is indicative of more than 620 μg and up to 1085 μg extracted equivalent of $Na_2O$. The glass compositions described herein have an ISO 719 hydrolytic resistance of type HGB2 or better with some embodiments having a type HGB1 hydrolytic resistance.

The glass compositions described herein have an acid resistance of at least class S3 according to DIN 12116 both before and after ion exchange strengthening with some embodiments having an acid resistance of at least class S2 or even class S1 following ion exchange strengthening. In some other embodiments, the glass compositions may have an acid resistance of at least class S2 both before and after ion exchange strengthening with some embodiments having an acid resistance of class S1 following ion exchange strengthening. Further, the glass compositions described herein have a base resistance according to ISO 695 of at least class A2 before and after ion exchange strengthening with some embodiments having a class A1 base resistance at least after ion exchange strengthening. The glass compositions described herein also have an ISO 720 type HGA2 hydrolytic resistance both before and after ion exchange strengthening with some embodiments having a type HGA1 hydrolytic resistance after ion exchange strengthening and some other embodiments having a type HGA1 hydrolytic resistance both before and after ion exchange strengthening. The glass compositions described herein have an ISO 719 hydrolytic resistance of type HGB2 or better with some embodiments having a type HGB1 hydrolytic resistance. It should be understood that, when referring to the above referenced classifications according to DIN 12116, ISO 695, ISO 720 and ISO 719, a glass composition or glass article which has "at least" a specified classification means that the performance of the glass composition is as good as or better than the specified classification. For example, a glass article which has a DIN 12116 acid resistance of "at least class S2" may have a DIN 12116 classification of either S1 or S2.

The glass compositions described herein are formed by mixing a batch of glass raw materials (e.g., powders of $SiO_2$, $Al_2O_3$, alkali oxides, alkaline earth oxides and the like) such that the batch of glass raw materials has the desired composition. Thereafter, the batch of glass raw materials is heated to form a molten glass composition which is subsequently cooled and solidified to form the glass composition. During solidification (i.e., when the glass composition is plastically deformable) the glass composition may be shaped using standard forming techniques to shape the glass composition into a desired final form. Alternatively, the glass article may be shaped into a stock form, such as a sheet, tube or the like, and subsequently reheated and formed into the desired final form.

In order to assess the long-term resistance of the glass container to delamination, an accelerated delamination test was utilized. The test is performed on glass containers after the containers have been ion-exchange strengthened. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers.

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles due based on the aspect ratio of the particle (i.e., the ratio of the width of the particle to the thickness of the particle). Delamination produces particulate flakes or lamellae which are irregularly shaped and are typically >50 µm in diameter but often >200 µm. The thickness of the flakes is usually greater than about 100 nm and may be as large as about 1 µm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

In the embodiments described herein, glass containers which average less than 3 glass particles with a minimum width of 50 µm and an aspect ratio of greater than 50 per trial following accelerated delamination testing are considered to have a delamination factor of 3. In the embodiments described herein, glass containers which average less than 2 glass particles with a minimum width of 50 µm and an aspect ratio of greater than 50 per trial following accelerated delamination testing are considered to have a delamination factor of 2. In the embodiments described herein, glass containers which average less than 1 glass particle with a minimum width of 50 µm and an aspect ratio of greater than 50 per trial following accelerated delamination testing are considered to have a delamination factor of 1. In the embodiments described herein, glass containers which have 0 glass particles with a minimum width of 50 µm and an aspect ratio of greater than 50 per trial following accelerated delamination testing are considered to have a delamination factor of 0. Accordingly, it should be understood that the lower the delamination factor, the better the resistance of the glass container to delamination. In the embodiments described herein, the glass containers have a delamination factor of 3 or lower (i.e., a delamination factor of 3, 2, 1 or 0).

Pharmaceutical Containers

In view of the chemical durability of the glass composition of the present invention, the glass compositions described herein are particularly well suited for use in designing pharmaceutical containers for storing, maintaining and/or delivering pharmaceutical compositions, such as liquids, solutions, powders, e.g., lyophilized powders, solids and the like. As used herein, the term "pharmaceutical container" refers to a composition designed to store, maintain and/or deliver a pharmaceutical composition. The pharmaceutical containers, as described herein, are formed, at least in part, of the delamination resistant glass compositions described above. Pharmaceutical containers of the present invention include, but are not limited to, Vacutainers™ cartridges, syringes, ampoules, bottles, flasks, phials, tubes, beakers, vials, injection pens or the like. In a particular embodiment, the pharmaceutical container is a vial. In a particular embodiment, the pharmaceutical container is an ampoule. In a particular embodiment, the pharmaceutical container is an injection pen. In a particular embodiment, the pharmaceutical container is a tube. In a particular embodiment, the pharmaceutical container is a bottle. In a particular embodiment, the pharmaceutical container is a syringe.

Moreover, the ability to chemically strengthen the glass compositions through ion exchange can be utilized to improve the mechanical durability of pharmaceutical containers formed from the glass composition. Accordingly, it should be understood that, in at least one embodiment, the glass compositions are incorporated in a pharmaceutical container in order to improve the chemical durability and/or the mechanical durability of the pharmaceutical container.

Pharmaceutical Compositions

In various embodiments, the pharmaceutical container further includes a pharmaceutical composition comprising an active pharmaceutical ingredient (API). As used herein, the term "pharmaceutical composition" refers to a composition comprising an active pharmaceutical ingredient to be delivered to a subject, for example, for therapeutic, prophylactic, diagnostic, preventative or prognostic effect. In certain embodiments, the pharmaceutical composition comprises the active pharmaceutical ingredient and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it may be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the active pharmaceutical agent.

As used herein, the term "active pharmaceutical ingredient" or "API" refers to a substance in a pharmaceutical composition that provides a desired effect, for example, a therapeutic, prophylactic, diagnostic, preventative or prognostic effect. In various embodiments, the active pharmaceutical ingredient can be any of a variety of substances known in the art, for example, a small molecule, a polypeptide mimetic, a biologic, an antisense RNA, a small interfering RNA (siRNA), etc.

For example, in a particular embodiment, the active pharmaceutical ingredient may be a small molecule. As used herein, the term "small molecule" includes any chemical or other moiety, other than polypeptides and nucleic acids, that can act to affect biological processes. Small molecules can include any number of therapeutic agents presently known and used, or that can be synthesized from a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include, without limitation, organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

In another embodiment, the active pharmaceutical ingredient may be a polypeptide mimetic ("peptidomimetic"). As used herein, the term "polypeptide mimetic" is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

In other embodiments, the active pharmaceutical ingredient may be a biologic. As used herein, the term "biologic" includes products created by biologic processes instead of by chemical synthesis. Non-limiting examples of a "biologic" include proteins, antibodies, antibody like molecules, vaccines, blood, blood components, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, and targeted proteases. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64 (8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253 (5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307 (1):198-205. Additional discussion of related principles, methods, etc., that may be applicable in the context of this invention are provided in, e.g., Fassina, Immunomethods. October 1994; 5 (2):121-9.

In various embodiments, the active pharmaceutical ingredient may have any of a variety of activities selected from the group consisting of anti-rheumatics, anti-neoplastic, vaccines, anti-diabetics, haematologicals, muscle relaxant, immunostimulants, anti-coagulants, bone calcium regulators, sera and gammaglobulins, anti-fibrinolytics, MS therapies, anti-anaemics, cytostatics, interferons, anti-metabolites, radiopharmaceuticals, anti-psychotics, anti-bacterials, immunosuppressants, cytotoxic antibiotics, cerebral & peripheral vasotherapeutics, nootropics, CNS drugs, dermatologicals, angiotensin antagonists, anti-spasmodics, anti-cholinergics, interferons, anti-psoriasis agents, anti-hyperlipidaemics, cardiac therapies, alkylating agents, bronchodilators, anti-coagulants, anti-inflammatories, growth hormones, and diagnostic imaging agents.

In various embodiments, the pharmaceutical composition may be selected from the group consisting of FORTEO® (recombinant human teriparatide), DULAGLUTIDE® (LY2189265), recombinant insulin glargine, RAMUCIRUMAB® (IMC-1121B), SOLANEZUMAB® (LY2062430), IXEKIZUMAB® (LY2439821), TABALUMAB® (LY2127399), NECITUMUMAB® (IMC-11F8), or CIXUTUMUMAB® (IMC-A12).

In a particular embodiment, the pharmaceutical composition comprises FORTEO® (recombinant human teriparatide). In a particular embodiment, the active pharmaceutical ingredient comprises recombinant human parathyroid hormone analog (1-34) [rhPTH(1-34)], or an analog thereof (e.g. for the treatment of osteoporosis in men and women).

Teriparatide [rDNA origin] injection (FORTEO®) contains recombinant human parathyroid hormone (1-34) and is also called rhPTH (1-34). It has an identical sequence to the 34 N-terminal amino acids (the biologically active region) of the 84-amino acid human parathyroid hormone. Teriparatide (FORTEO®) has a molecular weight of 4117.8 daltons and its amino acid sequence is shown below (SEQ ID NO: 1):

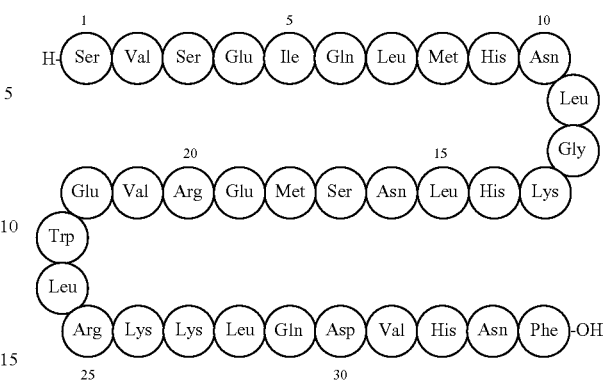

Teriparatide (rDNA origin) is manufactured using a strain of *Escherichia coli* modified by recombinant DNA technology. FORTEO® is supplied as a sterile, colorless, clear, isotonic solution in a glass cartridge which is pre-assembled into a disposable delivery device (pen) for subcutaneous injection. Each prefilled delivery device is filled with 2.7 mL to deliver 2.4 mL. Each mL contains 250 mcg teriparatide (corrected for acetate, chloride, and water content), 0.41 mg glacial acetic acid, 0.1 mg sodium acetate (anhydrous), 45.4 mg mannitol, 3 mg metacresol, and water for injection. In addition, hydrochloric acid solution 10% and/or sodium hydroxide solution 10% may be added to adjust the product to pH 4. Each cartridge, pre-assembled into a delivery device, delivers 20 mcg of teriparatide per dose each day for up to 28 days.

Teriparatide (rDNA origin) samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The activity of Teriparatide (rDNA origin) is determined using methods and controls appropriate to the agent, e.g. using the methods provided in U.S. Pat. Nos. 6,770,623; 6,977,077; 7,144,861; 7,163,684; 7,351,414; and 7,550,434, each of which is incorporated herein by reference.

In a particular embodiment, the pharmaceutical composition comprises DULAGLUTIDE®. In a particular embodiment, the active pharmaceutical ingredient comprises LY21892645.

LY2189265 (DULAGLUTIDE®) is a glucagon-like peptide-1 (GLP-1) immunoglobulin G (IgG4) Fc fusion protein. GLP-1 receptor agonists are novel agents for the treatment of type-2 diabetes, offering glucose-dependent insulinotropic effects, reduced glucagonemia and a neutral body-weight or weight-reducing profile. LY2189265 is a 275-amino acid protein and has a molecular formula of $C_{2646}H_{4044}N_{704}O_{836}S_{18}$ and molecular weight of 59.67 kDa.

In a particular embodiment, the pharmaceutical composition comprises a new recombinant insulin glargine product.

Insulin glargine [rDNA origin] injection is a sterile solution of insulin glargine for use as a subcutaneous injection. Insulin glargine is a recombinant human insulin analog that is a long-acting (up to 24-hour duration of action), parenteral blood-glucose-lowering agent. Insulin glargine recombinant is produced by recombinant DNA technology. Insulin glargine recombinant differs from human insulin in that the amino acid asparagine at position A21 is replaced by glycine and two arginines are added to the C-terminus of the B-chain. Chemically, insulin glargine is $21^{A}$-Gly-$30^{B}$a-L-Arg-$30^{B}$-L-Arg human insulin and has the empirical formula $C_{267}H_{404}N_{72}O_{78}S_{6}$ and a molecular weight of 6063. Insulin glargine recombinant has the following structural formula (SEQ ID NOS 2 and 3, respectively, in order of appearance):

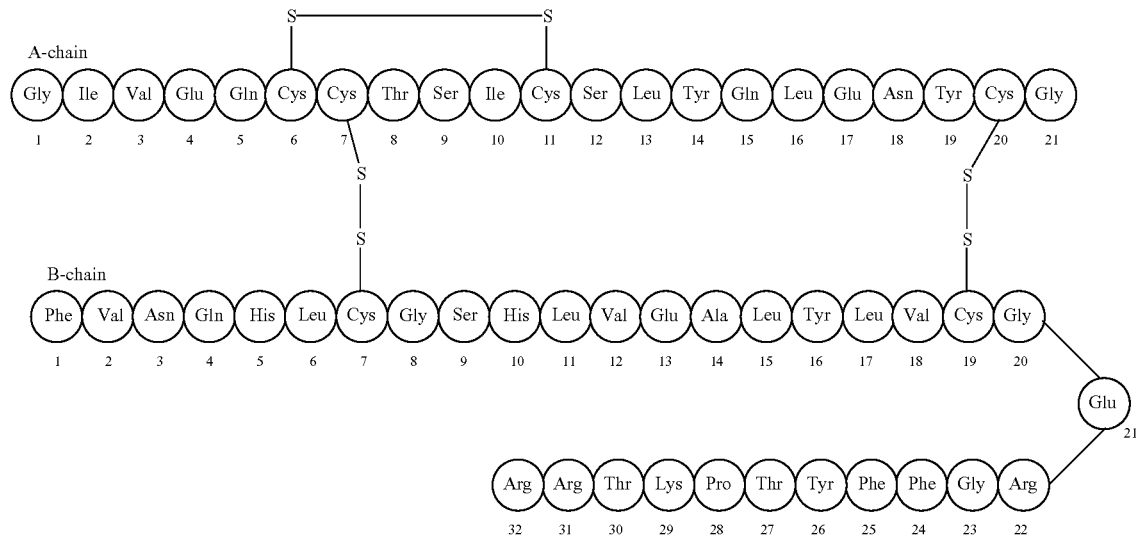

Insulin glargine recombinant consists of recombinant insulin glargine dissolved in a clear aqueous fluid. Each milliliter of Insulin glargine recombinant (insulin glargine injection) contains 100 Units (3.6378 mg) insulin glargine. The 10 mL vial presentation contains the following inactive ingredients per mL: 30 mcg zinc, 2.7 mg m-cresol, 20 mg glycerol 85%, 20 mcg polysorbate 20, and water for injection. The 3 mL cartridge presentation contains the following inactive ingredients per mL: 30 mcg zinc, 2.7 mg m-cresol, 20 mg glycerol 85%, and water for injection. The pH is adjusted by addition of aqueous solutions of hydrochloric acid and sodium hydroxide. Insulin glargine recombinant has a pH of approximately 4.

In a particular embodiment, the pharmaceutical composition comprises RAMUMCIRUMAB®. In a particular embodiment, the active pharmaceutical ingredient comprises IMC-1121B. IMC-1121B (RAMUMCIRUMAB®) is a fully human monoclonal (IgG1) anti-VEGFR-2 (flk-1) antibody. It has been hypothesized that treatment with IMC-1121B (RAMUMCIRUMAB®) can help prevent angiogenesis associated with tumor growth.

In a particular embodiment, the pharmaceutical composition comprises SOLANEZUMAB®. In a particular embodiment, the active pharmaceutical ingredient comprises LY2062430. LY2062430 (SOLANEZUMAB®) is a humanized, monoclonal, anti-β-amyloid antibody. It binds to the central region of β-amyloid, and it has been hypothesized that treatment with LY2062430 may help reduce the symptoms associated with diseases such as Alzheimer's and dementia. SOLANEZUMAB has a molecular formula of $C_{6396}H_{9922}N_{1712}O_{1996}S_{42}$ and a molecular weight of 144.08 kDa.

In a particular embodiment, the pharmaceutical composition comprises IXEKIZUMAB®. In a particular embodiment, the active pharmaceutical ingredient comprises LY2439821. LY2439821 (IXEKIZUMAB®) is a humanized anti-IL-17 (IL-17A) monoclonal antibody characterized as having a high affinity and slow off rate for human IL-17.

LY2439821 (IXEKIZUMAB®) is characterized by a strong binding affinity ($K_D$) for human IL-17, i.e., less than about 7 pM, 6.5 pM, 6.0 pM, 5.5 pM, 5.0 pM, 4.5 pM or 4.0 pM. Alternatively, LY2439821 is characterized by a $K_D$ for human IL-17 of no greater than about 7 pM, 6.5 pM, 6.0 pM, 5.5 pM, 5.0 pM, 4.5 pM or preferably no greater than about 4.0 pM. Preferably LY2439821 is further characterized with a $k_{off}$ rate from human IL-17 of less than $2 \times 10^{-5}$ s$^{-1}$. LY2439821 (IXEKIZUMAB®) has a molecular formula of $C_{6492}H_{10012}N_{1728}O_{2028}S_{46}$ and a molecular weight of 146.2 kDa.

In a particular embodiment, the pharmaceutical composition comprises TABALUMAB®. In a particular embodiment, the active pharmaceutical ingredient comprises LY2127399, or an anlog thereof. LY2127399 (TABALUMAB®) is a human monoclonal antibody that specifically binds to TNFSF13b polypeptides. TNFSF13b has high affinity for hTNFSF13b (e.g., $K_D=10^{-8}$ M or less), a slow off rate for TNFSF13b dissociation (e.g., $K_{off}=10^{-3}$ sec$^{-1}$ or less) and neutralizes TNFSF13b activity in vitro and in vivo. LY2127399 is useful in one embodiment for inhibiting TNFSF13b activity in a human subject suffering from a disorder in which hTNFSF13b activity is detrimental. LY2127399 has a molecular weight of 146.25 kDa and a molecular formula of $C_{6518}H_{10008}N_{1724}O_{2032}S_{38}$.

Pharmaceutical compositions of LY2127399 (TABALUMAB®) may be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration. Therapeutic agents of the invention can all be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 6 and 8 is tolerated.

In a particular embodiment, the pharmaceutical composition comprises NECITUMUMAB®. In a particular embodiment, the active pharmaceutical ingredient comprises IMC-11F8, or an analog thereof. IMC-11F8 (NECITUMUMAB®) is a fully human monoclonal antibody (IgG1) that binds to human epidermal growth factor receptor (EGFR) with high affinity and that neutralizes activation of EGFR. IMC-11F8 may potentially induce cell-mediated cytotoxicity in cancer cells due to the fact that it contains an IgG1 moiety, and can therefore be useful in treating mammals with neoplastic growth and non-cancerous hyperproliferative disease.

In a particular embodiment, the pharmaceutical composition comprises CIXUTUMUMAB®. In a particular embodiment, the active pharmaceutical ingredient comprises IMC-A12, or an anlog thereof. IMC-A12 (CIXUTUMUMAB®) is a fully human monoclonal antibody (IgG1) that specifically binds to insulin-like growth factor-I (IGF-I). IMC-A12 has been shown in vivo and in vitro to inhibit the growth of tumors.

CIXUTUMUMAB® can be packaged as a stable solution comprising IMC-A12 and a buffer. The antibody concentration can be from about 5 mg/mL to about 30 mg/mL. In one embodiment, the stable antibody solution formulation contains a citrate buffer. In a further embodiment, the citrate buffer is at a concentration between about 5 and about 50 mM. In a further embodiment, the citrate buffer is at a concentration of about 10 mM. In one embodiment, the stable antibody solution formulation contains glycine. In a further embodiment, the glycine concentration is about 75 mM to about 150 mM. In a further embodiment, the glycine concentration is about 100 mM. In one embodiment, the stable antibody solution formulation contains NaCl. In a further embodiment, the NaCl is at a concentration of about 75 to about 150 mM. In a further embodiment, the NaCl is at a concentration of about 100 mM. In one embodiment, the stable antibody solution formulation contains a surfactant. In a further embodiment, the surfactant is a polysorbate (TWEEN, a/k/a polyethylene-polypropylene glycol), such as polysorbate 20 or polysorbate 80. In a further embodiment, the surfactant is polysorbate 80 (TWEEN 80) at a concentration of about 0.001% to about 1.0% (weight per volume). In a further embodiment, the TWEEN 80 is at a concentration of about 0.01% (weight per volume). In one embodiment, the stable antibody solution formulation has a pH of about 6.0 to about 7.0. In a further embodiment, the pH is about 6.0 to about 6.5. In a further embodiment, the pH is about 6.5. In one embodiment, the stable antibody solution formulation comprises about 5 mg/ml IMC-A12; about 10 mM sodium citrate, about 100 mM glycine, about 100 mM NaCl, and about 0.01% TWEEN 80, wherein said formulation is at a pH of about 6.5.

Degradation and Stability of Pharmaceutical Compositions

According to the present invention, delamination resistant pharmaceutical containers comprising a glass composition provide for improved resistance to degradation of, improved stability of, improved resistance to inactivation of, and improved maintenance of levels of a pharmaceutical composition having at least one active pharmaceutical ingredient, for example, FORTEO® (recombinant human teriparatide), DULAGLUTIDE® (LY2189265), recombinant insulin glargine, RAMUCIRUMAB® (IMC-1121B), SOLANEZUMAB® (LY2062430) IXEKIZUMAB® (LY2439821), TABALUMAB® (LY2127399), NECITUMUMAB® (IMC-11F8), or CIXUTUMUMAB® (IMC-A12).

In one embodiment of the present invention, the delamination resistant pharmaceutical containers provide improved stability to pharmaceutical compositions contained therein, for example, FORTEO® (recombinant human teriparatide), DULAGLUTIDE® (LY2189265), recombinant insulin glargine, RAMUCIRUMAB® (IMC-1121B), SOLANEZUMAB® (LY2062430) IXEKIZUMAB® (LY2439821), TABALUMAB® (LY2127399), NECITUMUMAB® (IMC-11F8), or CIXUTUMUMAB® (IMC-A12). As used herein, the term "stability" refers to the ability of an active pharmaceutical ingredient to essentially retain its physical, chemical and conformational identity and integrity upon storage in the pharmaceutical containers of the invention. Stability is associated with the ability of an active pharmaceutical ingredient to retain its potency and efficacy over a period of time. Instability of an active pharmaceutical ingredient may be associated with, for example, chemical or physical degradation, fragmentation, conformational change, increased toxicity, aggregation (e.g., to form higher order polymers), deglycosylation, modification of glycosylation, oxidation, hydrolysis, or any other structural, chemical or physical modification. Such physical, chemical and/or conformational changes often result in reduced activity or inactivation of the active pharmaceutical ingredient, for example, such that at least one biological activity of the active pharmaceutical ingredient is reduced or eliminated. Alternatively or in addition, such physical, chemical and/or conformational changes often result in the formation of structures toxic to the subject to whom the pharmaceutical composition is administered.

The pharmaceutical containers of the present invention maintain stability of the pharmaceutical compositions, in part, by minimizing or eliminating delamination of the glass composition which forms, at least in part, the pharmaceutical container. In addition, the pharmaceutical containers of the present invention maintain stability of the pharmaceutical compositions, in part, by reducing or preventing the interaction of the active pharmaceutical ingredient with the pharmaceutical container and/or delaminated particles resulting therefrom. By minimizing or eliminating delamination and, further, by reducing or preventing interaction, the pharmaceutical containers thereby reduce or prevent the destabilization of the active pharmaceutical ingredient as found in, for example, FORTEO®, DULAGLUTIDE®, recombinant insulin glargine, RAMUCIRUMAB®, SOLANEZUMAB®, IXEKIZUMAB®, TABALUMAB®, NECITUMUMAB®, or CIXUTUMUMAB®.

The pharmaceutical containers of the present invention provide the additional advantage of preventing loss of active pharmaceutical ingredients. For example, by reducing or preventing the interaction of and, thus, the adherence of, the active pharmaceutical ingredient with the pharmaceutical container and/or delaminated particles resulting therefrom, the level of active pharmaceutical ingredient available for administration to a subject is maintained, as found in, for example, FORTEO® (recombinant human teriparatide), DULAGLUTIDE® (LY2189265), recombinant insulin glargine, RAMUCIRUMAB® (IMC-1121B), SOLANEZUMAB® (LY2062430), IXEKIZUMAB® (LY2439821), TABALUMAB® (LY2127399), NECITUMUMAB® (IMC-11F8), or CIXUTUMUMAB® (IMC-A12).

In one embodiment of the present invention, the pharmaceutical composition has a high pH. According to the present invention, it has been discovered that high pHs serve to increase delamination of glass compositions. Accordingly, the pharmaceutical containers of the present invention are particularly suitable for storing and maintaining pharmaceutical compositions having a high pH, for example, pharmaceutical compositions having a pH between about 7 and about 11, between about 7 and about 10, between about 7 and about 9, or between about 7 and about 8.

In additional embodiments, the pharmaceutical containers of the present invention are particularly suitable for storing and maintaining pharmaceutical compositions having phosphate or citrate based buffers. According to the present invention, it has been discovered that phosphate or citrate based buffers serve to increase delamination of glass compositions. According in particular embodiments, the pharmaceutical composition includes a buffer comprising a salt of citrate, e.g., sodium citrate, or SSC. In other embodiments, the pharmaceutical composition includes a buffer comprising a salt of phosphate, e.g., mono or disodium phosphate.

In additional embodiments, the pharmaceutical containers of the present invention are particularly suitable for storing and maintaining active pharmaceutical ingredient that needs to be subsequently formulated. In other embodiments, the pharmaceutical containers of the present invention are particularly suitable for storing and maintaining a lyophilized pharmaceutical composition or active pharmaceutical ingredient that requires reconstitution, for example, by addition of saline.

Assaying for Delamination of Pharmaceutical Containers

As noted above, delamination may result in the release of silica-rich glass flakes into a solution contained within the glass container after extended exposure to the solution. Accordingly, the resistance to delamination may be characterized by the number of glass particulates present in a solution contained within the glass container after exposure to the solution under specific conditions. In order to assess the long-term resistance of the glass container to delamination, an accelerated delamination test was utilized. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers. Table 7 summarizes some non-limiting examples of sample volumes and numbers of containers for testing is shown below:

TABLE 7

Table of Exemplary Test Specimens

| Nominal Vial Capacity (mL) | Vial Max Volume (mL) | Minimum Solution per Vial (mL) | Number of Vials in a Trial | Number of Trials | Total solution Tested (mL) |
|---|---|---|---|---|---|
| 2 | 4 | 3.2 | 4 | 10 | 128 |
| 3.5 | 7 | 5.6 | 2 | 10 | 112 |
| 4 | 6 | 4.8 | 3 | 10 | 144 |
| 5 | 10 | 8 | 2 | 10 | 160 |
| 6 | 10 | 8 | 2 | 10 | 160 |
| 8 | 11.5 | 9.2 | 2 | 10 | 184 |
| 10 | 13.5 | 10.8 | 1 | 10 | 108 |
| 20 | 26 | 20.8 | 1 | 10 | 208 |
| 30 | 37.5 | 30 | 1 | 10 | 300 |
| 50 | 63 | 50.4 | 1 | 10 | 504 |

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles based on the aspect ratio of the particle (i.e., the ratio of the width of the particle to the thickness of the particle). Delamination produces particulate flakes or lamellae which are irregularly shaped and are typically >50 μm in diameter but often >200 μm. The thickness of the flakes is usually greater than about 100 nm and may be as large as about 1 μm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

In the embodiments described herein, glass containers which average less than 3 glass particles with a minimum width of 50 µm and an aspect ratio of greater than 50 per trial following accelerated delamination testing are considered "delamination resistant." In the embodiments described herein, glass containers which average less than 2 glass particles with a minimum width of 50 µm and an aspect ratio of greater than 50 per trial following accelerated delamination testing are considered "delamination-stable." In the embodiments described herein, glass containers which average less than 1 glass particle with a minimum width of 50 µm and an aspect ratio of greater than 50 per trial following accelerated delamination testing are considered "delamination-proof." In the embodiments described herein, glass containers which have 0 glass particles with a minimum width of 50 µm and an aspect ratio of greater than 50 per trial following accelerated delamination testing are considered "delamination-free".

Assessing Stability of Pharmaceutical Compositions

As set forth above, any of a variety of active pharmaceutical ingredients can be incorporated within the claimed pharmaceutical container including, for example, a small molecule, a polypeptide mimetic, a biologic, an antisense RNA, a small interfering RNA (siRNA), etc. These active ingredients degrade in varying manners and, thus, assessing the stability thereof in the pharmaceutical containers of the present invention requires different techniques.

Depending on the nature of the active pharmaceutical ingredient, the stability, maintenance and/or continued efficacy of the pharmaceutical compositions contained within the delamination resistant pharmaceutical containers of the present invention can be evaluated as follows.

Biologics API are often susceptible to degradation and/or inactivation arising from various factors, including pH, temperature, temperature cycling, light, humidity, etc. Biologics API are further susceptible to degradation, inactivation or loss, arising from interaction of the pharmaceutical composition with the pharmaceutical container, or delaminants leeching therefrom. For example, biologics may undergo physical degradation which may render the resulting pharmaceutical composition inactive, toxic or insufficient to achieve the desired effect. Alternatively, or in addition, biologics may undergo structural or conformational changes that can alter the activity of the API, with or without degradation. For example, proteins may undergo unfolding which can result in effective loss and inactivity of the API. Alternatively, or in addition, biologics may adhere to the surface of the container, thereby rendering the API administered to the subject insufficient to achieve the desired effect, e.g., therapeutic effect.

(i) General Methods for Investigation of Biologic Compound Degradation

Depending on the size and complexity of the biologic, methods for analysis of degradation of non-biologic, small molecule API may be applied to biologics. For example, peptides and nucleic acids can be analyzed using any of a number of chromatography and spectrometry techniques applicable to small molecules to determine the size of the molecules, either with or without protease or nuclease digestion. However, as proper secondary and tertiary structures are required for the activity of biologics, particularly protein biologics, confirmation of molecular weight is insufficient to confirm activity of biologics. Protein biologics containing complex post-translational modifications, e.g., glycosylation, are less amenable to analysis using chromatography and spectrometry. Moreover, complex biologics, e.g., vaccines which can include complex peptide mixtures, attenuated or killed viruses, or killed cells, are not amenable to analysis by most chromatography or spectrometry methods.

(ii) In Vitro Functional Assays for Investigation of Compound Stability

One or more in vitro assays, optionally in combination with one or more in vivo assays, can be used to assess the stability and activity of the API. Functional assays to determine API stability can be selected based on the structural class of the API and the function of the API. Exemplary assays are provided below to confirm the activity of the API after stability and/or stress testing. It is understood that assays should be performed with the appropriate controls (e.g., vehicle controls, control API not subject to stress or stability testing) with a sufficient number of dilutions and replicate samples to provide data with sufficient statistical significance to detect changes in activity of 10% or less, preferably 5% or less, 4% or less, more preferably 3% or less, 2% or less, or 1% or less, as desired. Such considerations are well understood.

For example, antibody based therapeutics, regardless of the disease or condition to be treated, can be assayed for stability and activity using assays that require specific binding of the antibody to its cognate antigen, e.g., ELISA. The antigen used in the ELISA should have the appropriate conformational structure as would be found in vivo. Antibody based API are used, for example, for the treatment of cancer and inflammatory diseases including autoimmune diseases.

ELISA assays to assay the concentration of a protein biologic API are commercially available from a number of sources, e.g., R&D Systems, BD Biosciences, AbCam, Pierce, Invitrogen.

API are frequently targeted to receptors, particularly cell surface receptors. Receptor binding assays can be used to assess the activity of such agents. API that bind cell surface receptors can be agonists, antagonists or allosteric modulators. API that bind cell surface receptors need not bind the same location as the native ligand to modulate, for example, inhibit or enhance, signaling through the receptor. Depending on the activity of the API, an appropriate assay can be selected, e.g., assay for stimulation of receptor signaling when the API is a receptor agonist; and inhibition assay in which binding of an agonist, e.g., inhibition of activation by a receptor agonist by the API. Such assays can be used regardless of the disease(s) or condition(s) to be treated with the API. Modulation of cellular activity, e.g., cell proliferation, apoptosis, cell migration, modulation of expression of genes or proteins, differentiation, tube formation, etc. is assayed using routine methods. In other assay methods, a reporter construct is used to indicate activation of the receptor. Such methods are routine in the art. APIs that bind to cell surface receptors are used, for example, as anti-cancer agents, anti-diabetic agents, anti-inflammatory agents for the treatment of inflammatory mediated diseases including autoimmune disorders, anti-angiogenic agents, anti-cholinergic agents, bone calcium regulators, muscle and vascular tension regulators, and psychoactive agents.

Modulators of cell proliferation can be assayed for activity using a cell proliferation assays. For example, cell proliferation is induced using anti-anemic agents or stimulators of hematopoietic cell growth. Anti-proliferative agents, e.g., cytotoxic agents, anti-neoplastic agents, chemotherapeutic agents, cytostatic agents, antibiotic agents, are used to inhibit growth of various cell types. Some anti-inflammatory agents also act by inhibiting proliferation of immune cells, e.g., blast cells. In proliferation assays, replicate wells containing the same number of cells are cultured in the presence of the API. The effect of the API is assessed using, for example, microscopy or fluorescence activated cell sorting (FACS) to determine if the number of cells in the sample increased or decreased in response to the presence of the API. It is understood that the cell type selected for the proliferation assay is dependent on the specific API to be tested.

Modulators of angiogenesis can be assayed using cell migration and/or tube formation assays. For cell migration assays, human vascular endothelial cells (HUVECs) are cultured in the presence of the API in transwell devices. Migration of cells through the device at the desired time intervals is assessed. Alternatively, 3-dimensional HUVECs cultures in MATRIGEL can be assessed for tube formation. Anti-angiogenic agents are used, for example, for the treatment of cancer, macular degeneration, and diabetic retinopathy.

Anti-inflammatory API can be assayed for their effects on immune cell stimulation as determined, for example, by modulation of one or more of cytokine expression and secretion, antigen presentation, migration in response to cytokine or chemokine stimulation, and immune cell proliferation. In such assays, immune cells are cultured in the presence of the API and changes in immune cell activity are determined using routine methods in the art, e.g., ELISA and cell imaging and counting.

Anti-diabetic API can be assayed for their effects on insulin signaling, including insulin signaling in response to modulated glucose levels, and insulin secretion. Insulin signaling can be assessed by assessing kinase activation in response to exposure to insulin and/or modulation of glucose levels. Insulin secretion can be assessed by ELISA assay.

Modulators of blood clotting, i.e., fibrinolytics, anti-fibrinolytics, and anti-coagulants, can be assayed for their effects using an INR assay on serum by measuring prothrombin time to determine a prothrombin ratio. Time to formation of a clot is assayed in the presence or absence of the API.

Modulators of muscle or vascular tone can be assayed for their effects using vascular or muscle explants. The tissue can be placed in a caliper for detection of changes in length and/or tension. Whole coronary explants can be used to assess the activity of API on heart. The tissue is contacted with the API, and optionally agents to alter vascular tone (e.g., $K^+$, $Ca^{++}$). The effects of the API on length and/or tension of the vasculature or muscle is assessed.

Psychoactive agents can act by modulation of neurotransmitter release and/or recycling. Neuronal cells can be incubated in the presence of an API and stimulated to release neurotransmitters. Neurotransmitter levels can be assessed in the culture medium collected at defined time points to detect alterations in the level of neurotransmitter present in the media. Neurotransmitters can be detected, for example, using ELISA, LC/MS/MS, or by preloading the vesicles with radioactive neurotransmitters to facilitate detection.

(iii) In Vivo Assays for Investigation of Compound Stability

In addition to in vitro testing for compound stability, API can also be tested in vivo to confirm the stability of the API after storage and/or stress testing. For example, some API are not amenable to testing using in vitro assays due to the complexity of the disease state or the complexity of the response required. For example, psychoactive agents, e.g., antipsychotic agents, anti-depressant agents, nootropic agents, immunosuppressant agents, vasotherapeutic agents, muscular dystrophy agents, central nervous system modulating agents, antispasmodic agents, bone calcium regenerating agents, anti-rheumatic agents, anti-hyperlipidemic agents, hematopoietic proliferation agents, growth factors, vaccine agents, and imaging agents, may not be amenable to full functional characterization using in vitro models. Moreover, for some agents, factors that may not alter in vitro activity may alter activity in vivo, e.g., antibody variable domains may be sufficient to block signaling through a receptor, but the Fc domains may be required for efficacy in the treatment of disease. Further, changes in stability may result in changes in pharmacokinetic properties of an API (e.g., half-life, serum protein binding, tissue distribution, CNS permeability). Finally, changes in stability may result in the generation of toxic degradation or reaction products that would not be detected in vivo. Therefore, confirmation of pharmacokinetic and pharmacodynamic properties and toxicity in vivo is useful in conjunction with stability and stress testing.

(iv) Pharmacokinetic Assays

Pharmacokinetics includes the study of the mechanisms of absorption and distribution of an administered drug, the rate at which a drug action begins and the duration of the effect, the chemical changes of the substance in the body (e.g. by metabolic enzymes such as CYP or UGT enzymes) and the effects and routes of excretion of the metabolites of the drug. Pharmacokinetics is divided into several areas including the extent and rate of absorption, distribution, metabolism and excretion. This is commonly referred to as the ADME scheme:

Absorption—the process of a substance entering the blood circulation.

Distribution—the dispersion or dissemination of substances throughout the fluids and tissues of the body.

Metabolism (or Biotransformation)—the irreversible transformation of parent compounds into daughter metabolites.

Excretion—the removal of the substances from the body. In rare cases, some drugs irreversibly accumulate in body tissue.

Elimination is the result of metabolism and excretion.

Pharmacokinetics describes how the body affects a specific drug after administration. Pharmacokinetic properties of drugs may be affected by elements such as the site of administration and the dose of administered drug, which may affect the absorption rate. Such factors cannot be fully assessed using in vitro models.

The specific pharmacokinetic properties to be assessed for a specific API in stability testing will depend, for example, on the specific API to be tested. In vitro pharmacokinetic assays can include assays of drug metabolism by isolated enzymes or by cells in culture. However, pharmacokinetic analysis typically requires analysis in vivo.

As pharmacokinetics are not concerned with the activity of the drug, but instead with the absorption, distribution, metabolism, and excretion of the drug, assays can be performed in normal subjects, rather than subjects suffering from a disease or condition for which the API is typically administered, by administration of a single dose of the API to the subject. However, if the subject to be treated with the API has a condition that would alter the metabolism or excretion of the API, e.g., liver disease, kidney disease, testing of the API in an appropriate disease model may be useful. Depending on the half life of the compound, samples (e.g., serum, urine, stool) are collected at predetermined time points for at least two, preferably three half-lives of the API, and analyzed for the presence of the API and metabolic products of the API. At the end of the study, organs are harvested and analyzed for the presence of the API and metabolic products of the API. The pharmacokinetic properties of the API subjected to stability and/or stress testing are compared to API not subjected to stability or stress testing and other appropriate controls (e.g., vehicle control). Changes in pharmacokinetic properties as a result of stability and/or stress testing are determined.

(v) Pharmacodynamic Assays

Pharmacodynamics includes the study of the biochemical and physiological effects of drugs on the body or on microorganisms or parasites within or on the body and the mechanisms of drug action and the relationship between drug concentration and effect. Due to the complex nature of many disease states and the actions of many API, the API should be tested in vivo to confirm the desired activity of the agent. Mouse models for a large variety of disease states are known and commercially available (see, e.g., jaxmice.jax.org/query/f?p=205:1:989373419139701::::P1_ADV:1). A number of induced models of disease are also known. Agents can be tested on the appropriate animal model to demonstrate stability and efficacy of the API on modulating the disease state.

(vi) Specific Immune Response Assay

Vaccines produce complex immune responses that are best assessed in vivo. The specific potency assay for a vaccine depends, at least in part, on the specific vaccine type. The most accurate predictions are based on mathematical modeling of biologically relevant stability-indicating parameters. For complex vaccines, e.g., whole cell vaccines, whole virus vaccines, complex mixtures of antigens, characterization of each component biochemically may be difficult, if not impossible. For example, when using a live, attenuated virus vaccine, the number of plaque forming units (e.g., mumps, measles, rubella, smallpox) or colony forming units (e.g., S. typhi, TY21a) are determined to confirm potency after storage. Chemical and physical characterization (e.g., polysaccharide and polysaccharide-protein conjugate vaccines) is performed to confirm the stability and activity of the vaccine. Serological response in animals to inactivated toxins and/or animal protection against challenge (e.g., rabies, anthrax, diphtheria, tetanus) is performed to confirm activity of vaccines of any type, particularly when the activity of the antigen has been inactivated. In vivo testing of vaccines subjected to stability and/or stress testing is performed by administering the vaccine to a subject using the appropriate immunization protocol for the vaccine, and determining the immune response by detection of specific immune cells that respond to stimulation with the antigen or pathogen, detection of antibodies against the antigen or pathogen, or protection in an immune challenge. Such methods are well known in the art. Vaccines include, but are not limited to, meningococcal B vaccine, hepatitis A and B vaccines, human papillomavirus vaccine, influenza vaccine, herpes zoster vaccine, and pneumococcal vaccine.

(vii) Toxicity Assays

Degradation of API can result in in the formation of toxic agents. Toxicity assays include the administration of doses, typically far higher than would be used for therapeutic applications, to detect the presence of toxic products in the API. Toxicity assays can be performed in vitro and in vivo and are frequently single, high dose experiments. After administration of the compound, in addition to viability, organs are harvested and analyzed for any indication of toxicity, especially organs involved with clearance of API, e.g., liver, kidneys, and those for which damage could be catastrophic, e.g., heart, brain. The toxicologic properties of the API subjected to stability and/or stress testing are compared to API not subjected to stability or stress testing and other appropriate controls (e.g., vehicle control). Changes in toxicologic properties as a result of stability and/or stress testing are determined In accordance with present invention, the degradation, alteration or depletion of API contained within a delamination resistant pharmaceutical container of the present invention can be assessed by a variety of physical techniques. Indeed, in various aspects of the invention, the stability and degradation caused by the interaction of API with the container or delaminants thereof, or changes in concentration or amount of the API in a container can be assessed using techniques as follows. Such methods include, e.g., X-Ray Diffraction (XRPD), Thermal Analysis (such as Differential Scanning calorimetry (DSC), Thermogravimetry (TG) and Hot-Stage Microscopy (HSM), chromatography methods (such as High-Performance Liquid Chromatography (HPLC), Column Chromatography (CC), Gas Chromatography (GC), Thin-Layer Chromatography (TLC), and Super Critical Phase Chromatograph (SFC)), Mass Spectroscopy (MS), Capillary Electrophoresis (CE), Atomic Spectroscopy (AS), vibrational spectroscopy (such as Infrared Spectroscopy (IR)), Luminescence Spectroscopy (LS), and Nuclear Magnetic Resonance Spectroscopy (NMR).

In the case of pharmaceutical formulations where the API is not in solution or needs to be reconstituted into a different medium, XRPD may be a method for analyzing degradation. In ideal cases, every possible crystalline orientation is represented equally in a non-liquid sample.

Powder diffraction data is usually presented as a diffractogram in which the diffracted intensity I is shown as function either of the scattering angle $2\theta$ or as a function of the scattering vector q. The latter variable has the advantage that the diffractogram no longer depends on the value of the wavelength $\lambda$. Relative to other methods of analysis, powder diffraction allows for rapid, non-destructive analysis of multi-component mixtures without the need for extensive sample preparation. Deteriorations of an API may be analyzed using this method, e.g., by comparing the diffraction pattern of the API to a known standard of the API prior to packaging.

Thermal methods of analysis may include, e.g., differential scanning calorimetry (DSC), thermogravimetry (TG), and hot-stage microscopy (HSM). All three methods provide information upon heating the sample. Depending on the information required, heating can be static or dynamic in nature.

Differential scanning calorimetry monitors the energy required to maintain the sample and a reference at the same temperature as they are heated. A plot of heat flow (W/g or J/g) versus temperature is obtained. The area under a DSC peak is directly proportional to the heat absorbed or released and integration of the peak results in the heat of transition.

Thermogravimetry (TG) measures the weight change of a sample as a function of temperature. A total volatile content of the sample is obtained, but no information on the identity of the evolved gas is provided. The evolved gas must be identified by other methods, such as gas chromatography, Karl Fisher titration (specifically to measure water), TG-mass spectroscopy, or TG-infrared spectroscopy. The temperature of the volatilization and the presence of steps in the TG curve can provide information on how tightly water or solvent is held in the lattice. If the temperature of the TG volatilization is similar to an endothermic peak in the DSC, the DSC peak is likely due or partially due to volatilization. It may be necessary to utilize multiple techniques to determine if more than one thermal event is responsible for a given DSC peak.

Hot-Stage Microscopy (HSM) is a technique that supplements DSC and TG. Events observed by DSC and/or TG can be readily characterized by HSM. Melting, gas evolution, and solid-solid transformations can be visualized, providing the most straightforward means of identifying thermal events. Thermal analysis can be used to determine the melting points, recrystallizations, solid-state transformations, decompositions, and volatile contents of pharmaceutical materials.

Other methods to analyze degradation or alteration of API and excipients are infrared (IR) and Raman spectroscopy. These techniques are sensitive to the structure, conformation, and environment of organic compounds. Infrared spectroscopy is based on the conversion of IR radiation into molecular vibrations. For a vibration to be IR-active, it must involve a changing molecular dipole (asymmetric mode). For example, vibration of a dipolar carbonyl group is detectable by IR spectroscopy. Whereas IR has been traditionally used as an aid in structure elucidation, vibrational changes also serve as probes of intermolecular interactions in solid materials.

Raman spectroscopy is based on the inelastic scattering of laser radiation with loss of vibrational energy by a sample. A vibrational mode is Raman active when there is a change in the polarizability during the vibration. Symmetric modes tend to be Raman-active. For example, vibrations about bonds between the same atom, such as in alkynes, can be observed by Raman spectroscopy.

NMR spectroscopy probes atomic environments based on the different resonance frequencies exhibited by nuclei in a strong magnetic field. Many different nuclei are observable by the NMR technique, but those of hydrogen and carbon atoms are most frequently studied. Solid-state NMR measurements are extremely useful for characterizing the crystal forms of pharmaceutical solids. Nuclei that are typically analyzed with this technique include those of 13C, 31P, 15N, 25Mg, and 23Na.

Chromatography is a general term applied to a wide variety of separation techniques based on the sample partitioning between a moving phase, which can be a gas, liquid, or supercritical fluid, and a stationary phase, which may be either a liquid or a solid. Generally, the crux of chromatography lies in the highly selective chemical interactions that occur in both the mobile and stationary phases. For example, depending on the API and the separation required, one or more of absorption, ion-exchange, size-exclusion, bonded phase, reverse, or normal phase stationary phases may be employed.

Mass spectrometry (MS) is an analytical technique that works by ionizing chemical compounds to generate charged molecules or molecule fragments and measuring their mass-to-charge ratios. Based on this analysis method, one can determine, e.g., the isotopic composition of elements in an API and determine the structure of the API by observing its fragmentation pattern.

It would be understood that the foregoing methods do not represent a comprehensive list of means by which one can analyze possible deteriorations, alterations, or concentrations of certain APIs. Therefore, it would be understood that other methods for determining the physical amounts and/or characteristics of an API may be employed. Additional methods may include, but are not limited to, e.g., Capillary Electrophoresis (CE), Atomic Spectroscopy (AS), and Luminescence Spectroscopy (LS).

EXAMPLES

The embodiments of the delamination resistant pharmaceutical containers described herein will be further clarified by the following examples.

Example 1

Six exemplary inventive glass compositions (compositions A-F) were prepared. The specific compositions of each exemplary glass composition are reported below in Table 8. Multiple samples of each exemplary glass composition were produced. One set of samples of each composition was ion exchanged in a molten salt bath of 100% $KNO_3$ at a temperature of 450° C. for at least 5 hours to induce a compressive layer in the surface of the sample. The compressive layer had a surface compressive stress of at least 500 MPa and a depth of layer of at least 45 μm.

The chemical durability of each exemplary glass composition was then determined utilizing the DIN 12116 standard, the ISO 695 standard, and the ISO 720 standard described above. Specifically, non-ion exchanged test samples of each exemplary glass composition were subjected to testing according to one of the DIN 12116 standard, the ISO 695 standard, or the ISO 720 standard to determine the acid resistance, the base resistance or the hydrolytic resistance of the test sample, respectively. The hydrolytic resistance of the ion exchanged samples of each exemplary composition was determined according to the ISO 720 standard. The average results of all samples tested are reported below in Table 8.

As shown in Table 8, exemplary glass compositions A-F all demonstrated a glass mass loss of less than 5 $mg/dm^2$ and greater than 1 $mg/dm^2$ following testing according to the DIN 12116 standard with exemplary glass composition E having the lowest glass mass loss at 1.2 $mg/dm^2$. Accordingly, each of the exemplary glass compositions were classified in at least class S3 of the DIN 12116 standard, with exemplary glass composition E classified in class S2. Based on these test results, it is believed that the acid resistance of the glass samples improves with increased $SiO_2$ content.

Further, exemplary glass compositions A-F all demonstrated a glass mass loss of less than 80 $mg/dm^2$ following testing according to the ISO 695 standard with exemplary glass composition A having the lowest glass mass loss at 60 $mg/dm^2$. Accordingly, each of the exemplary glass compositions were classified in at least class A2 of the ISO 695 standard, with exemplary glass compositions A, B, D and F classified in class A1. In general, compositions with higher silica content exhibited lower base resistance and compositions with higher alkali/alkaline earth content exhibited greater base resistance.

Table 8 also shows that the non-ion exchanged test samples of exemplary glass compositions A-F all demonstrated a hydrolytic resistance of at least Type HGA2 following testing according to the ISO 720 standard with exemplary glass compositions C-F having a hydrolytic resistance of Type HGA1. The hydrolytic resistance of exemplary glass compositions C-F is believed to be due to higher amounts of $SiO_2$ and the lower amounts of $Na_2O$ in the glass compositions relative to exemplary glass compositions A and B.

Moreover, the ion exchanged test samples of exemplary glass compositions B-F demonstrated lower amounts of extracted $Na_2O$ per gram of glass than the non-ion exchanged test samples of the same exemplary glass compositions following testing according to the ISO 720 standard.

TABLE 8

Composition and Properties of Exemplary Glass Compositions

| | \multicolumn{6}{c|}{Composition in mole %} |
|---|---|---|---|---|---|---|
| | A | B | C | D | E | F |
| $SiO_2$ | 70.8 | 72.8 | 74.8 | 76.8 | 76.8 | 77.4 |
| $Al_2O_3$ | 7.5 | 7 | 6.5 | 6 | 6 | 7 |
| $Na_2O$ | 13.7 | 12.7 | 11.7 | 10.7 | 11.6 | 10 |
| $K_2O$ | 1 | 1 | 1 | 1 | 0.1 | 0.1 |
| MgO | 6.3 | 5.8 | 5.3 | 4.8 | 4.8 | 4.8 |
| CaO | 0.5 | 0.5 | 0.5 | 0.5 | 0.5 | 0.5 |
| $SnO_2$ | 0.2 | 0.2 | 0.2 | 0.2 | 0.2 | 0.2 |
| DIN 12116 ($mg/dm^2$) | 3.2 | 2.0 | 1.7 | 1.6 | 1.2 | 1.7 |
| classification | S3 | S3 | S3 | S3 | S2 | S3 |
| ISO 695 ($mg/dm^2$) | 60.7 | 65.4 | 77.9 | 71.5 | 76.5 | 62.4 |
| classification | A1 | A1 | A2 | A1 | A2 | A1 |
| ISO 720 (ug $Na_2O$/g glass) | 100.7 | 87.0 | 54.8 | 57.5 | 50.7 | 37.7 |
| classification | HGA2 | HGA2 | HGA1 | HGA1 | HGA1 | HGA1 |
| ISO 720 (with IX) (ug $Na_2O$/g glass) | 60.3 | 51.9 | 39.0 | 30.1 | 32.9 | 23.3 |
| classification | HGA1 | HGA1 | HGA1 | HGA1 | HGA1 | HGA1 |

Example 2

Three exemplary inventive glass compositions (compositions G-I) and three comparative glass compositions (compositions 1-3) were prepared. The ratio of alkali oxides to alumina (i.e., Y:X) was varied in each of the compositions in order to assess the effect of this ratio on various properties of the resultant glass melt and glass. The specific compositions of each of the exemplary inventive glass compositions and the comparative glass compositions are reported in Table 9. The strain point, anneal point, and softening point of melts formed from each of the glass compositions were determined and are reported in Table 2. In addition, the coefficient of thermal expansion (CTE), density, and stress optic coefficient (SOC) of the resultant glasses were also determined and are reported in Table 9. The hydrolytic resistance of glass samples formed from each exemplary inventive glass composition and each comparative glass composition was determined according to the ISO 720 Standard both before ion exchange and after ion exchange in a molten salt bath of 100% $KNO_3$ at 450° C. for 5 hours. For those samples that were ion exchanged, the compressive stress was determined with a fundamental stress meter (FSM) instrument, with the compressive stress value based on the measured stress optical coefficient (SOC). The FSM instrument couples light into and out of the birefringent glass surface. The measured birefringence is then related to stress through a material constant, the stress-optic or photoelastic coefficient (SOC or PEC) and two parameters are obtained: the maximum surface compressive stress (CS) and the exchanged depth of layer (DOL). The diffusivity of the alkali ions in the glass and the change in stress per square root of time were also determined

TABLE 9

Glass properties as a function of alkali to alumina ratio

| | \multicolumn{6}{c|}{Composition Mole %} |
|---|---|---|---|---|---|---|
| | G | H | I | 1 | 2 | 3 |
| $SiO_2$ | 76.965 | 76.852 | 76.962 | 76.919 | 76.960 | 77.156 |
| $Al_2O_3$ | 5.943 | 6.974 | 7.958 | 8.950 | 4.977 | 3.997 |
| $Na_2O$ | 11.427 | 10.473 | 9.451 | 8.468 | 12.393 | 13.277 |
| $K_2O$ | 0.101 | 0.100 | 0.102 | 0.105 | 0.100 | 0.100 |
| MgO | 4.842 | 4.878 | 4.802 | 4.836 | 4.852 | 4.757 |
| CaO | 0.474 | 0.478 | 0.481 | 0.480 | 0.468 | 0.462 |
| $SnO_2$ | 0.198 | 0.195 | 0.197 | 0.197 | 0.196 | 0.196 |
| Strain (° C.) | 578 | 616 | 654 | 683 | 548 | 518 |
| Anneal (° C.) | 633 | 674 | 716 | 745 | 600 | 567 |
| Softening (° C.) | 892 | 946 | 1003 | 1042 | 846 | 798 |
| Expansion ($10^{-7} K^{-1}$) | 67.3 | 64.3 | 59.3 | 55.1 | 71.8 | 74.6 |
| Density ($g/cm^3$) | 2.388 | 2.384 | 2.381 | 2.382 | 2.392 | 2.396 |
| SOC (nm/mm/Mpa) | 3.127 | 3.181 | 3.195 | 3.232 | 3.066 | 3.038 |
| ISO720 (non-IX) | 88.4 | 60.9 | 47.3 | 38.4 | 117.1 | 208.1 |
| ISO720 (IX450° C.-5hr) | 25.3 | 26 | 20.5 | 17.8 | 57.5 | 102.5 |
| $R_2O/Al_2O_3$ | 1.940 | 1.516 | 1.200 | 0.958 | 2.510 | 3.347 |
| CS@t = 0 (MPa) | 708 | 743 | 738 | 655 | 623 | 502 |
| CS/√t ($MPa/hr^{1/2}$) | −35 | −24 | −14 | −7 | −44 | −37 |
| D ($\mu m^2/hr$) | 52.0 | 53.2 | 50.3 | 45.1 | 51.1 | 52.4 |

The data in Table 9 indicates that the alkali to alumina ratio Y:X influences the melting behavior, hydrolytic resistance, and the compressive stress obtainable through ion exchange strengthening. In particular, FIG. 1 graphically depicts the strain point, anneal point, and softening point as a function of Y:X ratio for the glass compositions of Table 9. FIG. 1 demonstrates that, as the ratio of Y:X decreases below 0.9, the strain point, anneal point, and softening point of the glass rapidly increase. Accordingly, to obtain a glass which is readily meltable and formable, the ratio Y:X should be greater than or equal to 0.9 or even greater than or equal to 1.

Further, the data in Table 2 indicates that the diffusivity of the glass compositions generally decreases with the ratio of Y:X. Accordingly, to achieve glasses can be rapidly ion exchanged in order to reduce process times (and costs) the ratio of Y:X should be greater than or equal to 0.9 or even greater than or equal to 1.

Figure 2:
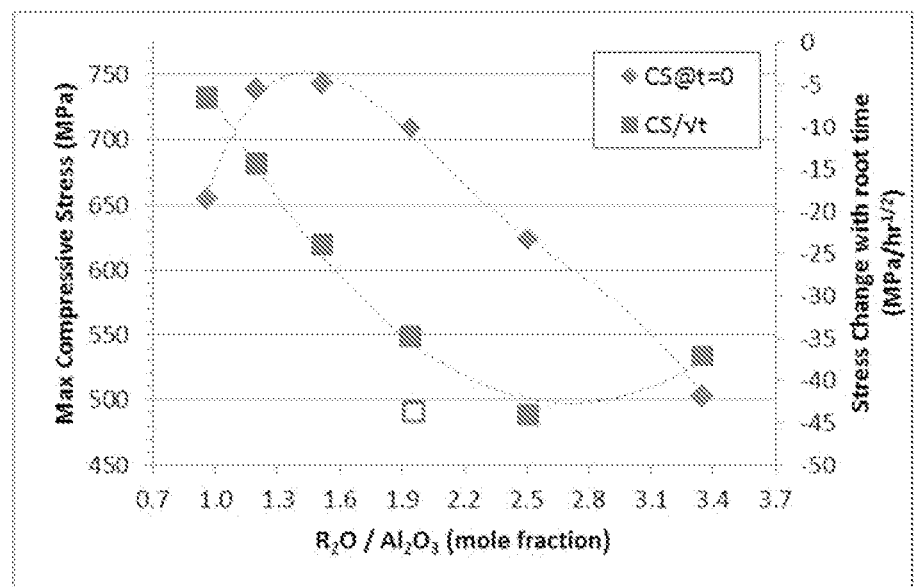
FIG. 2 graphically depicts the relationship between the ratio of alkali oxides to alumina (x-axis) and the maximum compressive stress and stress change (y-axes) of inventive and comparative glass compositions.

Moreover, FIG. 2 indicates that for a given ion exchange time and ion exchange temperature, the maximum compressive stresses are obtained when the ratio of Y:X is greater than or equal to about 0.9, or even greater than or equal to about 1, and less than or equal to about 2, specifically greater than or equal to about 1.3 and less than or equal to about 2.0. Accordingly, the maximum improvement in the load bearing strength of the glass can be obtained when the ratio of Y:X is greater than about 1 and less than or equal to about 2. It is generally understood that the maximum stress achievable by ion exchange will decay with increasing ion-exchange duration as indicated by the stress change rate (i.e., the measured compressive stress divided by the square root of the ion exchange time). FIG. 2 generally shows that the stress change rate decreases as the ratio Y:X decreases.

Figure 3:
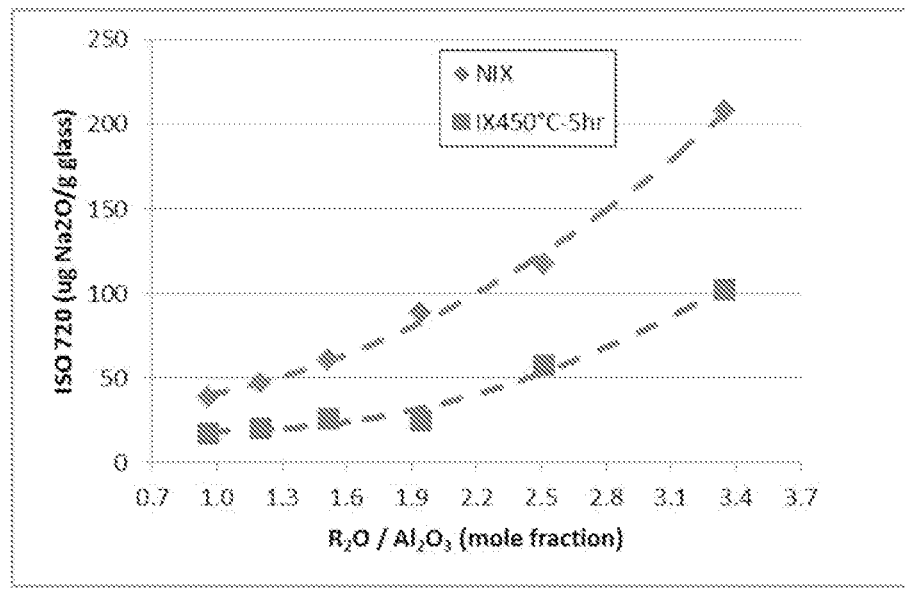
FIG. 3 graphically depicts the relationship between the ratio of alkali oxides to alumina (x-axis) and hydrolytic resistance as determined from the ISO 720 standard (y-axis) of inventive and comparative glass compositions.

FIG. 3 graphically depicts the hydrolytic resistance (y-axis) as a function of the ratio Y:X (x-axis). As shown in FIG. 3, the hydrolytic resistance of the glasses generally improves as the ratio Y:X decreases.

Based on the foregoing it should be understood that glasses with good melt behavior, superior ion exchange performance, and superior hydrolytic resistance can be achieved by maintaining the ratio Y:X in the glass from greater than or equal to about 0.9, or even greater than or equal to about 1, and less than or equal to about 2.

Example 3

Three exemplary inventive glass compositions (compositions J-L) and three comparative glass compositions (compositions 4-6) were prepared. The concentration of MgO and CaO in the glass compositions was varied to produce both MgO-rich compositions (i.e., compositions J-L and 4) and CaO-rich compositions (i.e., compositions 5-6). The relative amounts of MgO and CaO were also varied such that the glass compositions had different values for the ratio (CaO/(CaO+MgO)). The specific compositions of each of the exemplary inventive glass compositions and the comparative glass compositions are reported below in Table 10. The properties of each composition were determined as described above with respect to Example 2.

TABLE 10

Glass properties as function of CaO content

| | Composition Mole % | | | | | |
|---|---|---|---|---|---|---|
| | J | K | L | 4 | 5 | 6 |
| $SiO_2$ | 76.99 | 77.10 | 77.10 | 77.01 | 76.97 | 77.12 |
| $Al_2O_3$ | 5.98 | 5.97 | 5.96 | 5.96 | 5.97 | 5.98 |
| $Na_2O$ | 11.38 | 11.33 | 11.37 | 11.38 | 11.40 | 11.34 |
| $K_2O$ | 0.10 | 0.10 | 0.10 | 0.10 | 0.10 | 0.10 |
| MgO | 5.23 | 4.79 | 3.78 | 2.83 | 1.84 | 0.09 |
| CaO | 0.07 | 0.45 | 1.45 | 2.46 | 3.47 | 5.12 |
| $SnO_2$ | 0.20 | 0.19 | 0.19 | 0.19 | 0.19 | 0.19 |
| Strain (° C.) | 585 | 579 | 568 | 562 | 566 | 561 |
| Anneal (° C.) | 641 | 634 | 620 | 612 | 611 | 610 |
| Softening (° C.) | 902 | 895 | 872 | 859 | 847 | 834 |
| Expansion ($10^{-7} K^{-1}$) | 67.9 | 67.1 | 68.1 | 68.8 | 69.4 | 70.1 |
| Density (g/cm³) | 2.384 | 2.387 | 2.394 | 2.402 | 2.41 | 2.42 |
| SOC nm/mm/Mpa | 3.12 | 3.08 | 3.04 | 3.06 | 3.04 | 3.01 |
| ISO720 (non-IX) | 83.2 | 83.9 | 86 | 86 | 88.7 | 96.9 |
| ISO720 (IX450° C.-5hr) | 29.1 | | 28.4 | 33.2 | 37.3 | 40.1 |
| Fraction of RO as CaO | 0.014 | 0.086 | 0.277 | 0.465 | 0.654 | 0.982 |
| CS@t = 0 (MPa) | 707 | 717 | 713 | 689 | 693 | 676 |
| CS/√t (MPa/hr$^{1/2}$) | −36 | −37 | −39 | −38 | −43 | −44 |
| D (μm²/hr) | 57.2 | 50.8 | 40.2 | 31.4 | 26.4 | 20.7 |

Figure 4:
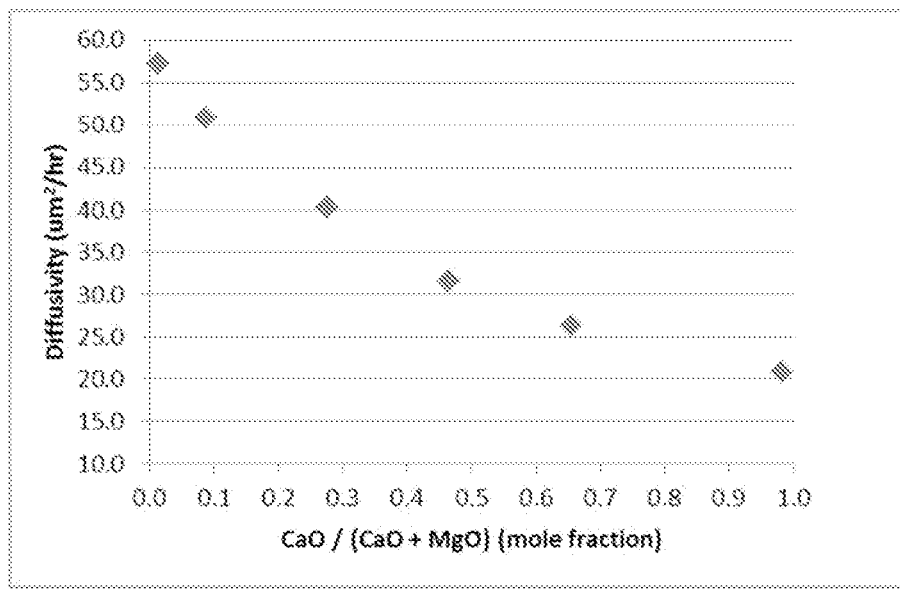
FIG. 4 graphically depicts diffusivity D (y-axis) as a function of the ratio ($CaO/(CaO+MgO)$) (x-axis) for inventive and comparative glass compositions.
Figure 5:
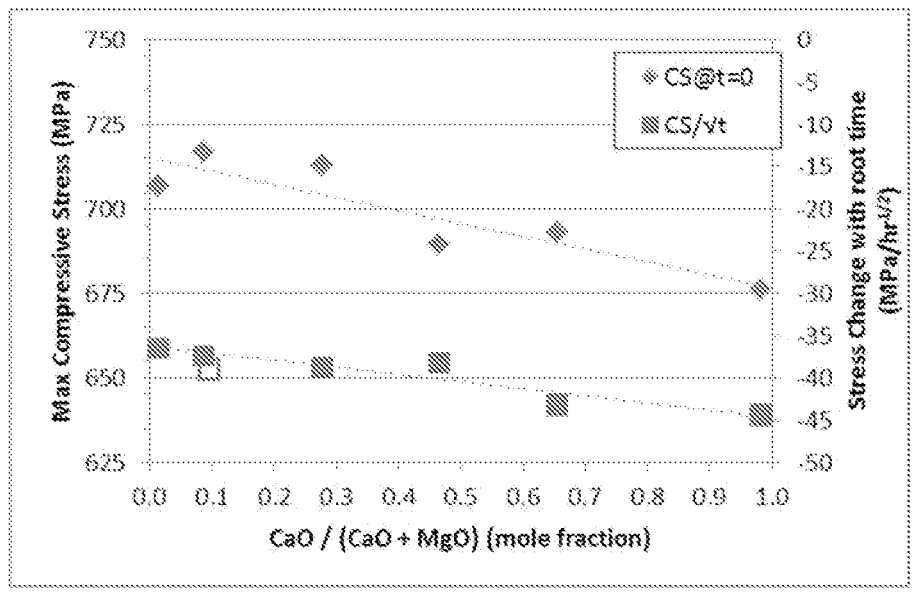
FIG. 5 graphically depicts the maximum compressive stress (y-axis) as a function of the ratio ($CaO/(CaO+MgO)$) (x-axis) for inventive and comparative glass compositions.

FIG. 4 graphically depicts the diffusivity D of the compositions listed in Table 10 as a function of the ratio (CaO/(CaO+MgO)). Specifically, FIG. 4 indicates that as the ratio (CaO/(CaO+MgO)) increases, the diffusivity of alkali ions in the resultant glass decreases thereby diminishing the ion exchange performance of the glass. This trend is supported by the data in Table 10 and FIG. 5. FIG. 5 graphically depicts the maximum compressive stress and stress change rate (y-axes) as a function of the ratio (CaO/(CaO+MgO)). FIG. 5 indicates that as the ratio (CaO/(CaO+MgO)) increases, the maximum obtainable compressive stress decreases for a given ion exchange temperature and ion exchange time. FIG. 5 also indicates that as the ratio (CaO/(CaO+MgO)) increases, the stress change rate increases (i.e., becomes more negative and less desirable).

Accordingly, based on the data in Table 10 and FIGS. 4 and 5, it should be understood that glasses with higher diffusivities can be produced by minimizing the ratio (CaO/(CaO+MgO)). It has been determined that glasses with suitable diffusivities can be produced when the (CaO/(CaO+MgO)) ratio is less than about 0.5. The diffusivity values of the glass when the (CaO/(CaO+MgO)) ratio is less than about 0.5 decreases the ion exchange process times needed to achieve a given compressive stress and depth of layer. Alternatively, glasses with higher diffusivities due to the ratio (CaO/(CaO+MgO)) may be used to achieve a higher compressive stress and depth of layer for a given ion exchange temperature and ion exchange time.

Moreover, the data in Table 10 also indicates that decreasing the ratio (CaO/(CaO+MgO)) by increasing the MgO concentration generally improves the resistance of the glass to hydrolytic degradation as measured by the ISO 720 standard.

Example 4

Three exemplary inventive glass compositions (compositions M-O) and three comparative glass compositions (compositions 7-9) were prepared. The concentration of $B_2O_3$ in the glass compositions was varied from 0 mol. % to about 4.6 mol. % such that the resultant glasses had different values for the ratio $B_2O_3/(R_2O—Al_2O_3)$. The specific compositions of each of the exemplary inventive glass compositions and the comparative glass compositions are reported below in Table 11. The properties of each glass composition were determined as described above with respect to Examples 2 and 3.

TABLE 11

Glass properties as a function of $B_2O_3$ content

| | Composition Mole % | | | | | |
|---|---|---|---|---|---|---|
| | M | N | O | 7 | 8 | 9 |
| $SiO_2$ | 76.860 | 76.778 | 76.396 | 74.780 | 73.843 | 72.782 |
| $Al_2O_3$ | 5.964 | 5.948 | 5.919 | 5.793 | 5.720 | 5.867 |
| $B_2O_3$ | 0.000 | 0.214 | 0.777 | 2.840 | 4.443 | 4.636 |
| $Na_2O$ | 11.486 | 11.408 | 11.294 | 11.036 | 10.580 | 11.099 |
| $K_2O$ | 0.101 | 0.100 | 0.100 | 0.098 | 0.088 | 0.098 |
| MgO | 4.849 | 4.827 | 4.801 | 4.754 | 4.645 | 4.817 |
| CaO | 0.492 | 0.480 | 0.475 | 0.463 | 0.453 | 0.465 |
| $SnO_2$ | 0.197 | 0.192 | 0.192 | 0.188 | 0.183 | 0.189 |
| Strain (° C.) | 579 | 575 | 572 | 560 | 552 | 548 |
| Anneal (° C.) | 632 | 626 | 622 | 606 | 597 | 590 |
| Softening (° C.) | 889 | 880 | 873 | 836 | 816 | 801 |
| Expansion ($10^{-7} K^{-1}$) | 68.3 | 67.4 | 67.4 | 65.8 | 64.1 | 67.3 |
| Density (g/cm³) | 2.388 | 2.389 | 2.390 | 2.394 | 2.392 | 2.403 |
| SOC (nm/mm/MPa) | 3.13 | 3.12 | 3.13 | 3.17 | 3.21 | 3.18 |
| ISO720 (non-IX) | 86.3 | 78.8 | 68.5 | 64.4 | 52.7 | 54.1 |
| ISO720 (IX450° C.-5hr) | 32.2 | 30.1 | 26 | 24.7 | 22.6 | 26.7 |
| $B_2O_3/(R_2O-Al_2O_3)$ | 0.000 | 0.038 | 0.142 | 0.532 | 0.898 | 0.870 |
| CS@t = 0 (MPa) | 703 | 714 | 722 | 701 | 686 | 734 |
| CS/√t (MPa/hr$^{1/2}$) | −38 | −38 | −38 | −33 | −32 | −39 |
| D (μm²/hr) | 51.7 | 43.8 | 38.6 | 22.9 | 16.6 | 15.6 |

Figure 6:
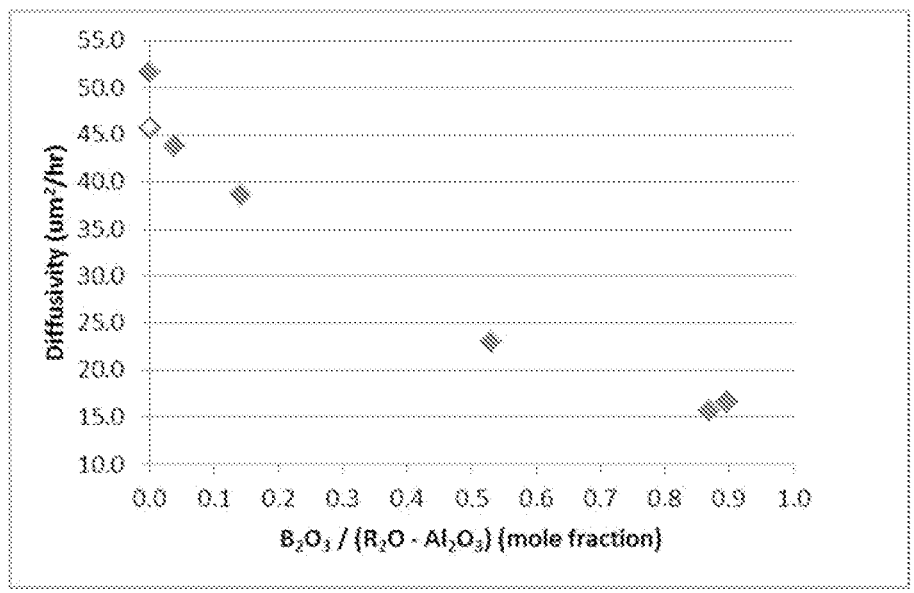
FIG. 6 graphically depicts diffusivity D (y-axis) as a function of the ratio ($B_2O_3/(R_2O-Al_2O_3)$) (x-axis) for inventive and comparative glass compositions.

FIG. 6 graphically depicts the diffusivity D (y-axis) of the glass compositions in Table 11 as a function of the ratio $B_2O_3/(R_2O—Al_2O_3)$ (x-axis) for the glass compositions of Table 11. As shown in FIG. 6, the diffusivity of alkali ions in the glass generally decreases as the ratio $B_2O_3/(R_2O—Al_2O_3)$ increases.

Figure 7:
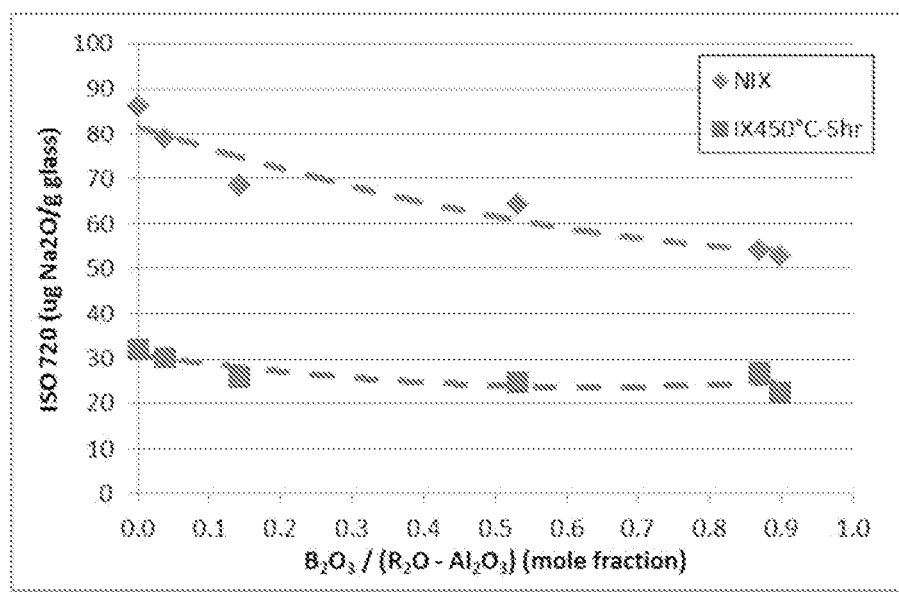
FIG. 7 graphically depicts the hydrolytic resistance as determined from the ISO 720 standard (y-axis) as a function of the ratio ($B_2O_3/(R_2O-Al_2O_3)$) (x-axis) for inventive and comparative glass compositions.

FIG. 7 graphically depicts the hydrolytic resistance according to the ISO 720 standard (y-axis) as a function of the ratio $B_2O_3/(R_2O—Al_2O_3)$ (x-axis) for the glass compositions of Table 11. As shown in FIG. 6, the hydrolytic resistance of the glass compositions generally improves as the ratio $B_2O_3/(R_2O—Al_2O_3)$ increases.

Based on FIGS. 6 and 7, it should be understood that minimizing the ratio $B_2O_3/(R_2O—Al_2O_3)$ improves the diffusivity of alkali ions in the glass thereby improving the ion exchange characteristics of the glass. Further, increasing the ratio $B_2O_3/(R_2O—Al_2O_3)$ also generally improves the resistance of the glass to hydrolytic degradation. In addition, it has been found that the resistance of the glass to degradation in acidic solutions (as measured by the DIN 12116 standard) generally improves with decreasing concentrations of $B_2O_3$. Accordingly, it has been determined that maintaining the ratio $B_2O_3/(R_2O—Al_2O_3)$ to less than or equal to about 0.3 provides the glass with improved hydrolytic and acid resistances as well as providing for improved ion exchange characteristics.

It should now be understood that the glass compositions described herein exhibit chemical durability as well as mechanical durability following ion exchange. These properties make the glass compositions well suited for use in various applications including, without limitation, pharmaceutical packaging materials.

Example 5

Determining the Presence and Amount of Glass Flakes in Pharmaceutical Solutions

The resistance to delamination may be characterized by the number of glass particulates present in a pharmaceutical solution contained within a glass container described herein after. In order to assess the long-term resistance of the glass container to delamination, an accelerated delamination test is utilized. The test consists of washing the glass container at room temperature for 1 minute and depyrogenating the container at about 320° C. for 1 hour. Thereafter a pharmaceutical solution is placed in the glass container to 80-90% full, the glass container is closed, and rapidly heated to, for example, 100° C. and then heated from 100° C. to 121° C. at a ramp rate of 1 deg/min at a pressure of 2 atmospheres. The glass container and solution are held at this temperature for 60 minutes, cooled to room temperature at a rate of 0.5 deg./min and the heating cycle and hold are repeated. The glass container is then heated to 50° C. and held for two days for elevated temperature conditioning. After heating, the glass container is dropped from a distance of at least 18" onto a firm surface, such as a laminated tile floor, to dislodge any flakes or particles that are weakly adhered to the inner surface of the glass container.

Thereafter, the pharmaceutical solution contained in the glass container is analyzed to determine the number of glass particles present per liter of solution. Specifically, the solution from the glass container is directly poured onto the center of a Millipore Isopore Membrane filter (Millipore #ATTP02500 held in an assembly with parts #AP1002500 and #M000025A0) attached to vacuum suction to draw the solution through the filter within 10-15 seconds. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 microns are counted manually. There are 9 such measurements made in the center of each filter membrane in a 3×3 pattern with no overlap between images. A minimum of 100 mL of solution is tested. As such, the solution from a plurality of small containers may be pooled to bring the total amount of solution to 100 mL. If the containers contain more than 10 mL of solution, the entire amount of solution from the container is examined for the presence of particles. For containers having a volume greater than 10 mL containers, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 sets of 10 mL of solution, each of which is analyzed and the particle count averaged over the 10 sets to determine an average particle count. Averaging the particle count over multiple containers accounts for potential variations in the delamination behavior of individual containers.

It should be understood that the aforementioned test is used to identify particles which are shed from the interior wall(s) of the glass container due to delamination and not tramp particles present in the container from forming processes. Specifically, delamination particles will be differentiated from tramp glass particles based on the aspect ratio of the particle (i.e., the ratio of the width of the particle to the thickness of the particle). Delamination produces particulate flakes or lamellae which are irregularly shaped and are typically >50 µm in diameter but often >200 µm. The thickness of the flakes is usually greater than about 100 nm and may be as large as about 1 µm. Thus, the minimum aspect ratio of the flakes is typically >50. The aspect ratio may be greater than 100 and sometimes greater than 1000. Particles resulting from delamination processes generally have an aspect ratio which is generally greater than about 50. In contrast, tramp glass particles will generally have a low aspect ratio which is less than about 3. Accordingly, particles resulting from delamination may be differentiated from tramp particles based on aspect ratio during observation with the microscope. Validation results can be accomplished by evaluating the heel region of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101(4), 2012, pages 1378-1384, is noted.

Using this method, pharmaceutical compositions can be tested for the presence of glass flakes and various compositions can be compared to each other to assess the safety of various pharmaceutical compositions.

Example 6

Stability Testing of Pharmaceutical Compositions

Stability studies are part of the testing required by the FDA and other regulatory agencies. Stability studies should include testing of those attributes of the API that are susceptible to change during storage and are likely to influence quality, safety, and/or efficacy. The testing should cover, as appropriate, the physical, chemical, biological, and microbiological attributes of the API (e.g., small molecule or biologic therapeutic agent) in the container with the closure to be used for storage of the agent. If the API is formulated as a liquid by the manufacturer, the final formulation should be assayed for stability. If the API is formulated as an agent for reconstitution by the end user using a solution provided by the manufacturer, both the API and the solution for reconstitution are preferably tested for stability as the separate packaged components (e.g., the API subjected to storage reconstituted with solution for reconstitution not subject to storage, API not subject to storage reconstituted with a solution subject to storage, and both API and solution subject to storage). This is particularly the case when the solution for reconstitution includes an active agent (e.g., an adjuvant for reconstitution of a vaccine).

In general, a substance API should be evaluated under storage conditions (with appropriate tolerances) that test its thermal stability and, if applicable, its sensitivity to moisture. The storage conditions and the lengths of studies chosen should be sufficient to cover storage, shipment, and subsequent use.

API should be stored in the container(s) in which the API will be provided to the end user (e.g., vials, ampules, syringes, injectable devices). Stability testing methods provided herein refer to samples being removed from the storage or stress conditions indicated. Removal of a sample preferably refers to removing an entire container from the storage or stress conditions. Removal of a sample should not be understood as withdrawing a portion of the API from the container as removal of a portion of the API from the container would result in changes of fill volume, gas environment, etc. At the time of testing the API subject to stability and/or stress testing, portions of the samples subject to stability and/or stress testing can be used for individual assays.

The long-term testing should cover a minimum of 12 months' duration on at least three primary batches at the time of submission and should be continued for a period of time sufficient to cover the proposed retest period. Additional data accumulated during the assessment period of the registration application should be submitted to the authorities if requested. Data from the accelerated storage condition and, if appropriate, from the intermediate storage condition can be used to evaluate the effect of short-term excursions outside the label storage conditions (such as might occur during shipping).

Long-term, accelerated, and, where appropriate, intermediate storage conditions for API are detailed in the sections below. The general case should apply if the API is not specifically covered by a subsequent section. It is understood that the time points for analysis indicated in the table are suggested end points for analysis. Interim analysis can be preformed at shorter time points (e.g., 1, 2, 3, 4, 5, 6, 7, 8, 9, 10, or 11 months). For API to be labeled as stable for storage for more than 12 months, time points beyond 12 months can be assessed (e.g., 15, 18, 21, 24 months). Alternative storage conditions can be used if justified.

TABLE 12

General Conditions for Stability Analysis

| Study | Storage condition | Time points for analysis |
| --- | --- | --- |
| Long-term | Long-term* 25° C. ± 2° C./60% RH ± 5% RH or 30° C. ± 2° C./65% RH ± 5% RH | 12 months |
| Intermediate | 30° C. ± 2° C./65% RH ± 5% RH | 6 months |
| Accelerated | 40° C. ± 2° C./75% RH ± 5% RH | 6 months |

TABLE 13

Conditions for Stability Analysis for Storage in a Refrigerator

| Study | Storage condition | Minimum time period covered by data at submission |
| --- | --- | --- |
| Long-term | 5° C. ± 3° C. | 12 months |
| Accelerated | 25° C. ± 2° C./60% RH ± 5% RH | 6 months |

TABLE 14

Conditions for Stability Analysis for Storage in a Freezer

| Study | Storage condition | Minimum time period covered by data at submission |
| --- | --- | --- |
| Long-term | −20° C. ± 5° C. | 12 months |

Storage condition for API intended to be stored in a freezer, testing on a single batch at an elevated temperature (e.g., 5° C.±3° C. or 25° C.±2° C.) for an appropriate time period should be conducted to address the effect of short-term excursions outside the proposed label storage condition (e.g., stress during shipping or handling, e.g., increased temperature, multiple freeze-thaw cycles, storage in a non-upright orientation, shaking, etc.).

The assays performed to assess stability of an API include assays to that are used across most APIs to assess the physical properties of the API, e.g., degradation, pH, color, particulate formation, concentration, toxicity, etc. Assays to detect the general properties of the API are also selected based on the chemical class of the agent, e.g., denaturation and aggregation of protein based API. Assays to detect the potency of the API, i.e., the ability of the API to achieve its intended effect as demonstrated by the quantitative measurement of an attribute indicative of the clinical effect as compared to an appropriate control, are selected based on the activity of the particular agent. For example, the biological activity of the API, e.g., enzyme inhibitor activity, cell killing activity, anti-inflammatory activity, coagulation modulating activity, etc., is measured using in vitro and/or in vivo assays such as those provided herein. Pharmacokinetic and toxicological properties of the API are also assessed using methods known in the art, such as those provided herein.

Example 7

Analysis of Adherence to Glass Vials

Changes in the surface of glass can result in changes in the adherence of API to glass. The amount of agent in samples withdrawn from glass vials are tested at intervals to determine if the concentration of the API in solution changes over time. API are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the concentration of the API in solution. The concentration of the API is determined using methods and controls appropriate to the API. The concentration of the API is preferably determined in conjunction with at least one assay to confirm that the API, rather than degradation products of the API, is detected. In the case of biologics in which the conformational structure of the biologic agent is essential to its function of the API, the assays for concentration of the biologic are preferably preformed in conjunction with an assay to confirm the structure of the biologic (e.g., activity assay).

For example, in the cases of small molecule APIs, the amount of agent present is determined, for example, by mass spectrometry, optionally in combination with liquid chromatography, as appropriate, to separate the agent from any degradation products that may be present in the sample.

For protein based biologic APIs, the concentration of the API is determined, for example, using ELISA assay. Chromatography methods are used in conjunction with methods to determine protein concentration to confirm that protein fragments or aggregates are not being detected by the ELISA assay.

For nucleic acid biologic APIs, the concentration of the API is determined, for example, using quantitative PCR when the nucleic acids are of sufficient length to permit detection by such methods. Chromatography methods are used to determine both the concentration and size of nucleic acid based API.

For viral vaccine APIs, the concentration of the virus is determined, for example, using colony formation assays.

Example 8

Analysis of Pharmacokinetic Properties

Pharmacokinetics is concerned with the analysis of absorption, distribution, metabolism, and excretion of API. Storage and stress can potentially affect the pharmacokinetic properties of various API. To assess pharmacokinetics of API subject to stability and/or stress testing, agents are incubated in containers as described in Example 6. Preferably, the API are incubated both in standard glass vials with appropriate closures and glass vials such as those provided herein. At the desired intervals, samples are removed and assayed.

The API is delivered to subjects by the typical route of delivery for the API (e.g., injection, oral, topical). As pharmacokinetics are concerned with the absorption and elimination of the API, normal subjects are typically used to assess pharmacokinetic properties of the API. However, if the API is to be used in subjects with compromised ability to absorb or eliminate the API (e.g., subjects with liver or kidney disease), testing in an appropriate disease model may be advantageous. Depending on the half life of the compound, samples (e.g., blood, urine, stool) are collected at predetermined time points (e.g., 0 min, 30 min, 60 min, 90 min, 120 min, 4 hours, 6 hours, 12 hours, 24 hours, 36 hours, 48 hours, etc.) for at least two, preferably three half-lives of the API, and analyzed for the presence of the API and metabolic products of the API. At the end of the study, organs are harvested and analyzed for the presence of the API and metabolic products of the API.

The results are analyzed using an appropriate model selected based on, at least, the route of administration of the API. The pharmacokinetic properties of the API subjected to stability and/or stress testing are compared to API not subjected to stability or stress testing and other appropriate controls (e.g., vehicle control). Changes, if any, in pharmacokinetic properties as a result of storage of the API under each condition are determined.

Example 9

Analysis of Toxicity Profiles

Storage of API can result in alterations of toxicity of API as a result of reactivity of the API with the container, leeching of agents from the container, delamination resulting in particulates in the agent, reaction of the API molecules with each other or components of the storage buffer, or other causes.

Agents are incubated in containers as described in the stability testing and/or stress testing methods provided in Example 6. Preferably, the API is incubated both in standard glass vials with appropriate closures and glass vials such as those provided herein. At the desired intervals, samples are removed and assayed to determine the toxicity the API. The toxicity of the API is determined using methods and controls appropriate to the API. In vitro and in vivo testing can be used alone or in combination to assess changes in toxicity of agents as a result of storage or stress.

In in vitro assays, cell lines are grown in culture and contacted with increasing concentrations of API subjected to stability and/or stress testing for predetermined amounts of time (e.g., 12, 24, 36, 48, and 72 hours). Cell viability is assessed using any of a number of routine or commercially available assays. Cells are observed, for example, by microscopy or using fluorescence activated cell sorting (FACS) analysis using commercially available reagents and kits. For example, membrane-permeant calcein AM is cleaved by esterases in live cells to yield cytoplasmic green fluorescence, and membrane-impermeant ethidium homodimer-1 labels nucleic acids of membrane-compromised cells with red fluorescence. Membrane-permeant SYTO 10 dye labels the nucleic acids of live cells with green fluorescence, and membrane-impermeant DEAD Red dye labels nucleic acids of membrane-compromised cells with red fluorescence. A change in the level of cell viability is detected between the cells contacted with API subjected to stress and/or stability testing in standard glass vials as compared to the glass vials provided herein and appropriate controls (e.g., API not subject to stability testing, vehicle control).

In vivo toxicity assays are performed in animals. Typically preliminary assays are performed on normal subjects. However, if the disease or condition to be treated could alter the susceptibility of the subject to toxic agents (e.g., decreased liver function, decreased kidney function), toxicity testing in an appropriate model of the disease or condition can be advantageous. One or more doses of agents subjected to stability and/or stress testing are administered to animals. Typically, doses are far higher (e.g., 5 times, 10 times) the dose that would be used therapeutically and are selected, at least in part, on the toxicity of the API not subject to stability and/or stress testing. However, for the purpose of assaying stability of API, the agent can be administered at a single dose that is close to (e.g., 70%-90%), but not at, a dose that would be toxic for the API not subject to stability or stress testing. In single dose studies, after administration of the API subject to stress and/or stability testing (e.g., 12 hours, 24 hours, 48 hours, 72 hours), during which time blood, urine, and stool samples may be collected. In long term studies, animals are administered a lower dose, closer to the dose used for therapeutic treatment, and are observed for changes indicating toxicity, e.g., weight loss, loss of appetite, physical changes, or death. In both short and long term studies, organs are harvested and analyzed to determine if the API is toxic. Organs of most interest are those involved in clearance of the API, e.g., liver and kidneys, and those for which toxicity would be most catastrophic, e.g., heart, brain. An analysis is performed to detect a change in toxicity between the API subjected to stress and/or stability testing in standard glass vials as compared to the glass vials provided herein, as compared to API not subject to stability and/or stress testing and vehicle control. Changes, if any, in toxicity properties as a result of storage of the API under each condition are determined Example 10

Analysis of Pharmacodynamic Profiles

Pharmacodynamics includes the study of the biochemical and physiological effects of drugs on the body or on microorganisms or parasites within or on the body and the mechanisms of drug action and the relationship between drug concentration and effect. Mouse models for a large variety of disease states are known and commercially available (see, e.g., jaxmice.jax.org/query/f?p=205:1:989373419139701::::P1_ADV:1). A number of induced models of disease are also known.

Agents are incubated in containers as described in the stability testing and/or stress testing methods provided in Example 6. Preferably, the samples are incubated both in standard glass vials with appropriate closures and glass vials such as those provided herein. At the desired intervals, samples are removed and assayed for pharmacodynamic activity using known animal models. Exemplary mouse models for testing the various classes of agents indicated are known in the art.

The mouse is treated with the API subject to stability and/or stress testing. The efficacy of the API subject to stability and/or stress testing to treat the appropriate disease or condition is assayed as compared to API not subject to stability and/or stress testing and vehicle control. Changes, if any, in pharmacodynamic properties as a result of storage of the API under each condition are determined.

Example 11

Confirmation of Stability and Activity of FORTEO®

Teriparatide [rDNA origin] injection (FORTEO®) contains recombinant human parathyroid hormone (1-34) and is also called rhPTH (1-34) (SEQ ID NO: 1). It has an identical sequence to the 34 N-terminal amino acids (the biologically active region) of the 84-amino acid human parathyroid hormone. Teriparatide has a molecular weight of 4117.8 daltons and its amino acid sequence is shown below (SEQ ID NO: 1):

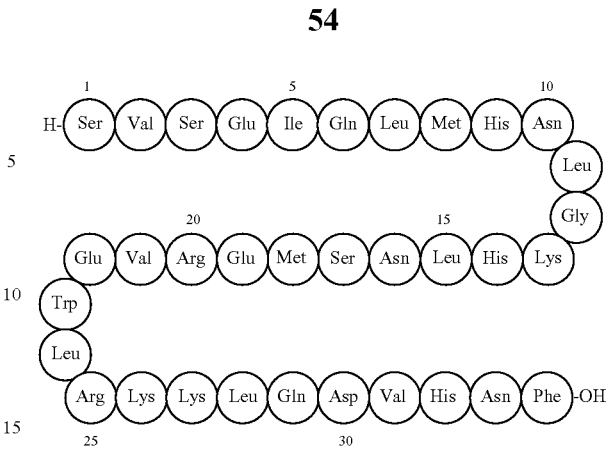

Teriparatide (rDNA origin) is manufactured using a strain of *Escherichia coli* modified by recombinant DNA technology. FORTEO® is supplied as a sterile, colorless, clear, isotonic solution in a glass cartridge which is pre-assembled into a disposable delivery device (pen) for subcutaneous injection. Each prefilled delivery device is filled with 2.7 mL to deliver 2.4 mL. Each mL contains 250 mcg teriparatide (corrected for acetate, chloride, and water content), 0.41 mg glacial acetic acid, 0.1 mg sodium acetate (anhydrous), 45.4 mg mannitol, 3 mg metacresol, and water for injection. In addition, hydrochloric acid solution 10% and/or sodium hydroxide solution 10% may be added to adjust the product to pH 4. Each cartridge, pre-assembled into a delivery device, delivers 20 mcg of teriparatide per dose each day for up to 28 days.

Teriparatide (rDNA origin) (FORTEO®) samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The activity of Teriparatide (rDNA origin) is determined using methods and controls appropriate to the agent, e.g. using the methods provided in U.S. Pat. Nos. 6,770,623; 6,977,077; 7,144,861; 7,163,684; 7,351,414; and 7,550,434, each of which is incorporated herein by reference, and from which the below examples are adapted.

Preparation of Solution 0.1 mg rhPTH (1-34), 50 mg mannitol, 2.5 mg m-cresol, 0.52 mg acetic acid and 0.12 mg sodium acetate were mixed into a solution with 1 mL distilled water (solution (i)).

Determination of Stability 0.25 mg rhPTH (1-34), 45.4 mg mannitol, 3 mg m-cresol, 0.41 mg acetic acid and 0.1 mg sodium acetate were mixed into a solution with 1 mL of distilled water (solution (ii)).

The formulations of the present invention were compared to solutions containing no stabilizer, 0.9% NaCl, 20 mM acetate and 10 mM acetate as primary stabilizer. The stability was measured by determining the amount in percent of rhPTH (1-34) remaining after a certain time. The measurement was made by HPLC. The results are shown in Tables 15 and 16.

TABLE 15

Effect of Primary Stabilizer on Chemical Stability of rhPTH
(1-34) at 50° C.
% Remaining

| Time, days | Water | 0.9% NaCl | 20 mM acetate | 10 mM acetate |
|---|---|---|---|---|
| Initial | 100 | 100 | 100 | 100 |
| 7 | 74 | 81 | 84 | 80 |
| 14 | 55 | 58 | 67 | 71 |

TABLE 16

Comparison of rhPTH (1-34) at 30° C.
% Remaining

| Time, days | 20 mM acetate | 10 mM acetate | Solution (i) | Solution (ii) |
|---|---|---|---|---|
| Initial | 100 | 100 | 100 | 100 |
| 7 | 96 | 94 | 100 | — |
| 14 | 94 | 92 | 96 | 100 |
| 21 | 90 | 93 | 97 | — |
| 30 | — | 81 | 96 | 96 |

Lyophilized Powder Formulations

The following experiment was carried out to show that lyophilized powder formulations prepared from stabilized solutions of the present invention are more stable than a control which was prepared from PTH (1-34) and mannitol alone.

A control solution and solutions for samples A through O are were prepared as previously described with the ingredients and concentrations shown in Table 17. The solutions are then freeze-dried and the resulting lyophilized power formulations are stored at 40° C. for a one-month period. The amount of PTH(1-34) remaining in each sample is then measured by HPLC. The results are shown in Table 17.

TABLE 17

Stability of PTH (1-34) Lyophilized
Formulations at 40° C. for One Month

| Sample | PTH (1-34) m/mL | Bulking Agent | Bulking Agent Conc. (mg/mL) | Buffer | Buffer Conc. (mg/mL) | % PTH Remaining |
|---|---|---|---|---|---|---|
| Control | 0.2 | mannitol | 40 | — | — | 78 |
| A | 0.5 | mannitol | 30 | acetate | 5 | 90 |
| B | 0.5 | Glycine | 30 | acetate | 5 | 98 |
| C | 0.5 | Sucrose | 30 | acetate | 5 | 98 |
| D | 0.5 | Trehalose | 30 | acetate | 5 | 97 |
| E | 0.5 | Raffinose | 30 | acetate | 5 | 99 |
| F | 0.75 | Mannitol | 30 | tartrate | 15 | 95 |
| G | 1.5 | Sucrose & mannitol | 5/25 | tartrate | 5 | 99 |
| H | 0.75 | Sucrose & mannitol | 5/25 | tartrate | 15 | ≥99 |
| I | 1.5 | Mannitol | 30 | tartrate | 5 | ≥96 |
| J | 1.5 | Sucrose | 30 | tartrate | 15 | ≥100 |
| K | 1.5 | Mannitol | 30 | tartrate | 15 | ≥99 |
| L | 0.75 | Sucrose | 30 | tartrate | 15 | ≥100 |
| M | 0.75 | Sucrose | 30 | tartrate | 5 | ≥100 |
| N | 1.5 | Sucrose & mannitol | 5/25 | tartrate | 15 | ≥99 |
| O | 1.5 | Sucrose & mannitol | 5/25 | acetate | 5 | ≥91 |

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient.

Example 12

Confirmation of Stability and Activity of
DULAGLUTIDE® (LY-2189265)

LY-2189265 (DULAGLUTIDE®) is a glucagon-like peptide-1 (GLP-1) immunoglobulin G (IgG4) Fc fusion protein. GLP-1 receptor agonists are novel agents for the treatment of type-2 diabetes, offering glucose-dependent insulinotropic effects, reduced glucagonemia and a neutral body-weight or weight-reducing profile. LY-2189265 is a 275-amino acid protein and has a molecular formula of $C_{2646}H_{4044}N_{704}O_{836}S_{18}$ and molecular weight of 59.67 kDa.

Samples of Dulaglutide® (LY-2189265) are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the activity of the agent in, at least, one in vitro or in vivo assay to assess the biological activity of Dulaglutide® (LY-2189265). The activity of Dulaglutide® (LY-2189265) is determined using methods and controls appropriate to the agent, for example using methods provided in *Diabetes/Metabolism Research and Reviews*, 2010; 26: 287-296; *Diabetes, Obesity and Metabolism*, 2011, 13: 418-425; *Diabetes, Obesity and Metabolism*, 2011, 13: 434-438 and/or US Patent publication US 2012/0294855, from which the below examples are adapted.

Expression and Purification of LY-2189265

Human embryonic kidney (HEK) 293-EBNA cells were maintained in Dulbecco modified Eagle medium (DMEM)/Ham F-12 medium (Invitrogen, Carlsbad, Calif., USA) supplemented with 20 mM HEPES (Invitrogen), 5 μg/mL nucellin (Eli Lilly and Company), 0.4 μg/mL tropolone (Sigma-Aldrich, St. Louis, Mo., USA), 0.075% (w/v) F68 (Invitrogen) and 50 μg/mL geneticin (Sigma-Aldrich) (37° C.; 5-8% $CO_2$). DNA was added to FuGene6 transfection reagent (Roche Molecular Biochemicals, Indianapolis, Ind., USA) in OptiMEM (Gibco/BRL, Gaithersburg, Md., USA) and incubated (15 min, 37° C.). Concentrated expression media was loaded directly onto a Hi-Trap Protein A column (GE Healthcare, Piscataway, N.J., USA), equilibrated in phosphate-buffered saline (PBS; 3 mL/min flow rate) and washed. Pooled fractions of bound GLP-1-Fc (pH 7.4), eluted with a step gradient of 100% 50 mM Na-citrate (pH 2.2), were concentrated and loaded onto a Superdex 200 (26/60, GE Healthcare) column (PBS-equilibrated; 3 mL/min flow rate). The GLP-1-Fc fractions were characterized by SDS-PAGE and mass spectrometry, sterile-filtered (0.22 μm), assessed for concentration (absorption at 280 nm) and stored at −20° C.

Blood Glucose and Insulin Level Measurement

Blood glucose levels were determined by Precision-G Blood Glucose Testing System (Abbott Diagnostics, Abbott Park, Ill., USA), and insulin levels were determined by radioimmunoassay (Linco Diagnostics, St Charles, Mo., USA).

Pharmakokinetics in Sprague-Dawley Rats and Cynomolgus Monkeys

Adult male rats (n=3/group) received a single subcutaneous (SC) dose of 0.1 mg/kg LY-2189265, and blood was collected 1, 2, 4, and 6 days later. Monkeys (N=3/group) received a single SC dose of 0.1 mg/kg LY-2189265, and blood (2 mL) was collected at 0, (pre-administration), 2, 4, 8, 12, 48, 72, 96, 192, 240, 288, and 336 h after administration. Plasma samples were stabilized with 10 μL DPP-IV inhibitor/mL (Millipore, St Charles, Mo., USA), and immunoreactive GLP-1-Fc concentration was determined by enzyme-linked immunosorbent assay (ELISA) using antibodies recognizing the N-terminus of GLP-1-Fc (Eli Lilly and Company) and the Fc domain (mouse anti-human IgG4; Southern Biotech, Birmingham, Ala., USA). Plasma samples were diluted with equal amounts of casein/PBS and incubated for 1.5 h. Secondary antibody (1:2000 in blocking buffer) was added for 1 h. Optical density (450-630 nm) of 3,3',5,5'-tetramethylbenzidine development was determined, concentrations of GLP-1-Fc were calculated using a four-parameter algorithm, and standard curves were prepared for GLP-1-Fc in rat plasma. The ELISA assay range was approximately 0.9-80 ng/mL.

Graded Glucose Infusion in Rats

Adult male Sprague-Dawley rats (420-460 g) with femoral artery and vein cannulation were acclimated to study boxes and subsequently treated with SC vehicle (saline; n=18) or LY-2189265 (0.3 nm/kg [n=4], 1 nmol/kg [n=3], 3 nmol/kg [n=7], or 30 nmol/kg [n=4]). After 24 h, fasted rats (16 h) were infused with saline (20 min), followed by low-dose glucose (50 mg/kg/min, 30 min) and finally high-dose glucose (150 mg/kg/min, 30 min). Blood samples (250 μL) were collected at −20, −10, 0, 20, 30, 40, 50, and 60 min Statistical significance was evaluated using the paired Student's t-test (JMP 4.04 statistical software)

Graded Glucose Infusion in Cynomolgus Monkeys

Sedated and fasted (16-18 h) cynomolgus monkeys (n=6) were infused with glucose immediately after SC administration of vehicle control (PBS) or LY2189265 (1.7 nmol/kg) and 1, 5, and 7 days later. Glucose solution (20% dextrose solution, 200 mg/mL, intravenous) was infused at 10 mg/kg/min (3.0 mL/kg/h) for 20 min and then at 25 mg/kg/min (7.5 mL/kg/h) for 20 min Blood was collected at −10, 0, 10, 20, 30, and 40 min. In a separate experiment, monkeys (n=6) receiving SC vehicle or LY 2189265 (1.7 nmol/kg) once weekly for 4 weeks were evaluated using graded glucose infusion paradigm 4 days after the last LY2189265 dose.

Subchronic Dosing of Diabetic Db/Db Mice for 4 Weeks

Five-week-old female diabetic db/db mice (C57BL/KsO-laHsd-Leprdb, Harlan Laboratories) were randomly grouped (n=10/group) according to body weight, and LY2189265 (10 nmol/kg) was administered subcutaneously once weekly for 4 weeks. Blood glucose was measured in conscious mice just before dosing by tail clip at each weekly injection, except for the first week, when glucose was measured at 1 h after administration. Fasted insulin levels were measured on day 0 and day 26 after an overnight fast.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient Example 13

Confirmation of Stability and Activity of Insulin Glargine Recombinant

Insulin glargine [rDNA origin] (SEQ ID NOS 2 and 3, respectively in order of appearance) injection is a sterile solution of insulin glargine for use as a subcutaneous injection. Insulin glargine is a recombinant human insulin analog that is a long-acting (up to 24-hour duration of action), parenteral blood-glucose-lowering agent. Insulin glargine recombinant is produced by recombinant DNA technology. Insulin glargine recombinant differs from human insulin in that the amino acid asparagine at position A21 is replaced by glycine and two arginines are added to the C-terminus of the B-chain. Chemically, insulin glargine is $21^{A}$-Gly-$30^{B}$a-L-Arg-$30^{B}$-L-Arg human insulin and has the empirical formula $C_{267}H_{404}N_{72}O_{78}S_6$ and a molecular weight of 6063. Insulin glargine recombinant has the following structural formula (SEQ ID NOS 2 and 3, respectively, in order of appearance):

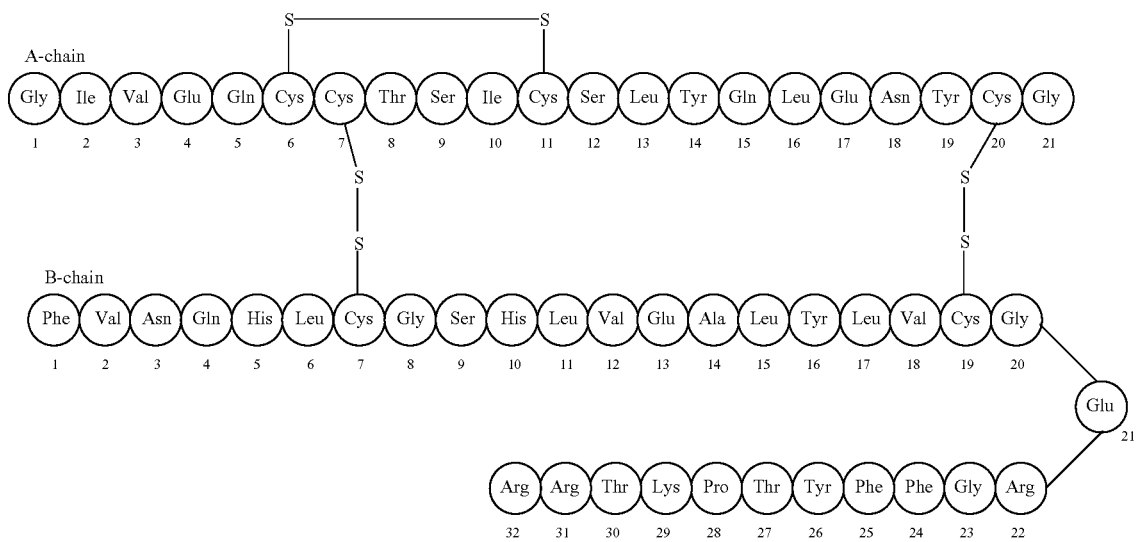

Insulin glargine recombinant consists of recombinant insulin glargine dissolved in a clear aqueous fluid. Each milliliter of Insulin glargine recombinant (insulin glargine injection) contains 100 Units (3.6378 mg) insulin glargine. The 10 mL vial presentation contains the following inactive ingredients per mL: 30 mcg zinc, 2.7 mg m-cresol, 20 mg glycerol 85%, 20 mcg polysorbate 20, and water for injection. The 3 mL cartridge presentation contains the following inactive ingredients per mL: 30 mcg zinc, 2.7 mg m-cresol, 20 mg glycerol 85%, and water for injection. The pH is adjusted by addition of aqueous solutions of hydrochloric acid and sodium hydroxide. Insulin glargine recombinant has a pH of approximately 4.

To determine the stability of Insulin glargine recombinant, Insulin glargine recombinant samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of insulin glargine recombinant is determined using methods and controls appropriate to the agent, for example, using methods provided in U.S. Pat. Nos. 5,656,722; 7,476,652; 7,713,930; and 7,918,833, the entire contents of which are incorporated by reference herein and from which the below examples are adapted.

Comparison Investigations

Different preparations containing the insulin analog insulin glargine (Gly(A21),Arg(B31),Arg(B32)-human insulin) are prepared. To this end, insulin glargine is suspended in one part of water for injection, dissolved at pH 3-4, the other constituents are added, the pH is adjusted to 4.0+/−0.2 using hydrochloric acid/NaOH and the mixture is made up to the final volume. The concentration of insulin glargine in each of the experiments described below is 3.6378 mg/ml (corresponds to 100 units/ml). A second preparation is produced identically, but a specific amount of a surfactant is additionally added. The solutions are filled into 10 ml glass vessels (vials) and fitted with crimp caps. These vessels are now exposed to simulated in use or physicomechanical stress conditions:

1. In use test: The vessels are sorted into boxes with turned-up lids and stored during the investigation period of 28 days at +25° C. and controlled room humidity with exclusion of light. To simulate taking by the patient, once daily about 5 IU of the solutions are withdrawn using a customary insulin syringe and discarded. At the beginning and end of the working week this procedure is carried out twice in order to simulate taking at the weekend. Before each withdrawal, visual assessment of the solution in the vessels for turbidity and/or particle formation is carried out.

2. Shaking test: The vessels are placed in a box with a turned-up lid lying on a laboratory shaker having an incubator and thermostat and shaken at 25° C. with 90 movements/min parallel to the horizontal movement for a period of time of 10 days. After defined times, the turbidity value of the samples is determined by means of a laboratory turbidity photometer (nephelometer) in formaldazine nephelometric units (formaldazine nephelometric unit=FNU). The turbidity value corresponds to the intensity of the scattered radiation of the light incident on suspended particles in the sample.

Stabilization of the in Use Period of Insulin Glargine Recombinant Using Polysorbate 80 (Tween® 80)

a) The solution is sterile-filtered through a combination of 0.2 μm and 0.1 μm filters. It is then poured into 10 ml injection vials and sealed using crimp caps having an inserted sealing disk.

b) A comparison solution is prepared identically, but first a suitable amount of surfactant (10-30 ppm of polysorbate 20) is suspended in water for injection. The samples are stored at +5° C., 25° C. and 37° C. for a fixed period of time. 10 samples in each case are then subjected to an in use test. The results are shown in Tables 18-24 below.

TABLE 18

Storage for 3 Months at 5° C.

| Test Sample | Number of vials with particle formation after | | | |
|---|---|---|---|---|
| | 7 days | 14 days | 21 days | 28 days |
| Insulin glargine | 7 | 10 | 10 | 10 |

| Test Sample | Number of vials with particle formation after | | | |
|---|---|---|---|---|
| | 7 days | 14 days | 21 days | 28 days |
| Insulin glargine + 0.010 mg/mL polysorbate 20 | 0 | 0 | 0 | 0 |
| Insulin glargine + 0.015 mg/mL polysorbate 20 | 0 | 0 | 0 | 0 |
| Insulin glargine + 0.020 mg/mL polysorbate 20 | 0 | 0 | 0 | 1 |
| Insulin glargine + 0.030 mg/mL polysorbate 20 | 0 | 0 | 0 | 0 |

TABLE 19

Storage for 6 months at 5° C.

| Test Sample | Number of vials with particle formation after | | | |
|---|---|---|---|---|
| | 7 days | 14 days | 21 days | 28 days |
| Insulin glargine | 7 | 10 | 10 | 10 |
| Insulin glargine + 0.010 mg/mL polysorbate 20 | 0 | 0 | 0 | 1 |
| Insulin glargine + 0.015 mg/mL polysorbate 20 | 0 | 0 | 0 | 0 |
| Insulin glargine+ 0.020 mg/mL polysorbate 20 | 0 | 0 | 0 | 1 |
| Insulin glargine + 0.030 mg/m L polysorbate 20 | 0 | 0 | 1 | 0 |

TABLE 20

Storage for 3 months at 25° C.

| Test Sample | Number of vials with particle formation after | | | |
|---|---|---|---|---|
| | 7 days | 14 days | 21 days | 28 days |
| Insulin glargine | 9 | 10 | 10 | 10 |
| Insulin glargine + 0.010 mg/mL polysorbate 20 | 2 | 2 | 2 | 2 |
| Insulin glargine + 0.015 mg/mL polysorbate 20 | 0 | 0 | 0 | 1 |
| Insulin glargine + 0.020 mg/mL polysorbate 20 | 0 | 0 | 0 | 0 |
| Insulin glargine + 0.030 mg/mL polysorbate 20 | 0 | 0 | 0 | 0 |

TABLE 21

Storage for 6 months at 25° C.

| Test Sample | Number of vials with particle formation after | | | |
|---|---|---|---|---|
| | 7 days | 14 days | 21 days | 28 days |
| Insulin glargine | 10 | 10 | 10 | 10 |
| Insulin glargine + 0.010 mg/mL polysorbate 20 | 0 | 0 | 0 | 1 |
| Insulin glargine 0.015 mg/mL | 0 | 0 | 1 | 0 |

| Test Sample | Number of vials with particle formation after | | | |
|---|---|---|---|---|
| | 7 days | 14 days | 21 days | 28 days |
| polysorbate 20 Insulin glargine + 0.030 mg/mL polysorbate 20 | 0 | 0 | 0 | 0 |
| Insulin glargine + 0.030 mg/mL polysorbate 20 | 0 | 0 | 0 | 0 |

TABLE 22

Storage for 1 month at 37° C.

| Test Sample | Number of vials with particle formation after | | | |
|---|---|---|---|---|
| | 7 days | 14 days | 21 days | 28 days |
| Insulin glargine | 0 | 10 | 10 | 10 |
| Insulin glargine + 0.010 mg/mL polysorbate 20 | 0 | 3 | 3 | 5 |
| Insulin glargine + 0.015 mg/mL polysorbate 20 | 0 | 0 | 0 | 0 |
| Insulin glargine + 0.030 mg/mL polysorbate 20 | 0 | 0 | 0 | 0 |
| Insulin glargine+ 0.030 mg/mL polysorbate 20 | 0 | 0 | 0 | 0 |

TABLE 23

Storage for 3 months at 37° C.

| Test Sample | Number of vials with particle formation after | | | |
|---|---|---|---|---|
| | 7 days | 14 days | 21 days | 28 days |
| Insulin glargine | 5 | 9 | 10 | 10 |
| Insulin glargine + 0.010 mg/mL polysorbate 20 | 1 | 1 | 1 | 1 |
| Insulin glargine 0.015 mg/mL polysorbate 20 | 0 | 0 | 0 | 0 |
| Insulin glargine + 0.030 mg/mL polysorbate 20 | 0 | 0 | 0 | 0 |
| Insulin glargine + 0.030 mg/mL polysorbate 20 | 0 | 0 | 0 | 0 |

TABLE 24

Storage for 6 months at 37° C.

| Test Sample | Number of vials with particle formation after | | | |
|---|---|---|---|---|
| | 7 days | 14 days | 21 days | 28 days |
| Insulin glargine | 10 | 10 | 10 | 10 |
| Insulin glargine + 0.010 mg/mL polysorbate 20 | 0 | 0 | 0 | 0 |
| Insulin glargine + 0.015 mg/mL polysorbate 20 | 0 | 0 | 1 | 0 |
| Insulin glargine + 0.030 mg/mL polysorbate 20 | 0 | 0 | 0 | 0 |
| Insulin glargine + 0.030 mg/mL polysorbate 20 | 1 | 1 | 1 | 1 |

Without addition of polysorbate 20, particle formation can occur in the solution even after 7 days in use. By addition of polysorbate 20, the particle formation can be markedly suppressed during the in use period. The stabilizing action of polysorbate 20 is retained even on storage at elevated temperatures for a period of 3 months. A decline in the stabilizing action due to possible hydrolysis of the polysorbate in the acidic medium of the solution cannot be determined in comparison with the data after storage for 1 month.

Stabilization of Insulin Glargine Using Polysorbate 20 Under Physico-Mechanical Stress Loading a) The solution is sterile-filtered through a combination of 0.2 μm and 0.1 μm filters. It is then poured into 10 ml injection vials and sealed using crimp caps having an inserted sealing disk.

b) A comparison solution is prepared identically, but first a suitable amount of surfactant (0.010-0.030 mg/ml of polysorbate 20) is suspended in water for injection.

The samples are stored at +5° C., 25° C. and 37° C. for a fixed period of time. 5 samples in each case are then subjected to a shaking test. The results are shown in Tables 25-27 below, the limit 15 FNU corresponds to turbidities which are discernible in daylight.

TABLE 25

Storage for 1 month at 5° C.

| Test Sample | Number of Vials >15 FNU | | | | | | | | |
|---|---|---|---|---|---|---|---|---|---|
| | 0 days | 0.5 days | 1 day | 2 days | 3 days | 4 days | 6 days | 8 days | 10 days |
| Insulin glargine | 0 | 0 | 0 | 2 | 3 | 3 | 4 | 4 | 4 |
| Insulin glargine + 0.010 mg/mL polysorbate 20 | 0 | 0 | 0 | 0 | 0 | 1 | 3 | 4 | 5 |
| Insulin glargine + 0.015 mg/mL polysorbate 20 | 0 | 0 | 0 | 0 | 0 | 0 | 0 | 0 | 0 |
| Insulin glargine + 0.020 mg/mL polysorbate 20 | 0 | 0 | 0 | 0 | 0 | 0 | 0 | 0 | 0 |

TABLE 25-continued

Storage for 1 month at 5° C.

Number of Vials >15 FNU

| Test Sample | 0 days | 0.5 days | 1 day | 2 days | 3 days | 4 days | 6 days | 8 days | 10 days |
|---|---|---|---|---|---|---|---|---|---|
| Insulin glargine + 0.030 mg/mL polysorbate 20 | 0 | 0 | 0 | 0 | 0 | 0 | 0 | 0 | 0 |

TABLE 26

Storage for 1 month at 25° C.

Number of Vials >15 FNU

| Test Sample | 0 days | 0.5 days | 1 day | 2 days | 3 days | 4 days | 6 days | 8 days | 10 days |
|---|---|---|---|---|---|---|---|---|---|
| Insulin glargine | 0 | 0 | 0 | 1 | 1 | 1 | 1 | 2 | 3 |
| Insulin glargine + 0.010 mg/mL polysorbate 20 | 0 | 0 | 0 | 0 | 0 | 0 | 1 | 2 | 3 |
| Insulin glargine + 0.015 mg/mL polysorbate 20 | 0 | 0 | 0 | 0 | 0 | 0 | 0 | 0 | 0 |
| Insulin glargine + 0.020 mg/mL polysorbate 20 | 0 | 0 | 0 | 0 | 0 | 0 | 0 | 0 | 0 |
| Insulin glargine + 0.030 mg/mL polysorbate 20 | 0 | 0 | 0 | 0 | 0 | 0 | 0 | 0 | 0 |

TABLE 27

Storage for 1 month at 37° C.

Number of Vials >15 FNU

| Test Sample | 0 days | 0.5 days | 1 day | 2 days | 3 days | 4 days | 6 days | 8 days | 10 days |
|---|---|---|---|---|---|---|---|---|---|
| Insulin glargine | 0 | 0 | 0 | 2 | 5 | 5 | 5 | 5 | 5 |
| Insulin glargine + 0.010 mg/mL polysorbate 20 | 0 | 0 | 0 | 0 | 0 | 0 | 0 | 0 | 0 |
| Insulin glargine + 0.015 mg/mL polysorbate 20 | 0 | 0 | 0 | 0 | 0 | 0 | 0 | 0 | 0 |
| Insulin glargine + 0.020 mg/mL polysorbate 20 | 0 | 0 | 0 | 0 | 0 | 0 | 0 | 0 | 0 |
| Insulin glargine + 0.030 mg/mL polysorbate 20 | 0 | 0 | 0 | 0 | 0 | 0 | 0 | 0 | 0 |

Without addition of polysorbate 20, even after 2 days of severe physicomechanical stress, a visible turbidity can occur in the solution. By addition of polysorbate 20, the formation of turbidity during physicomechanical stressing can be markedly delayed. The stabilizing action of polysorbate 20 is retained even on storage at elevated temperatures. A decline in the stabilizing action due to possible hydrolysis of the polysorbate in the acidic medium of the solution cannot be detected.

Comparison of the Stabilization of the in Use Period of Insulin Glargine Using Polysorbate 20 (Tween® 20) and Using Polysorbate 80 (Tween® 80)

Open 10 vials in each case to give 5 ml of insulin glargine injection solution and a) addition of 0.001 mg/ml of polysorbate 20 b) addition of 0.01 mg/ml of polysorbate 20 c) addition of 0.001 mg/ml of polysorbate 80 d) addition of 0.01 mg/ml of polysorbate 80 in the form of a concentrated stock solution. The samples are then subjected to an in use test. The results are shown in Table 28 below.

TABLE 28

Comparison of the Stabilization of the in Use Period of Insulin Glargine Using Polysorbate 20 (Tween ® 20) and Using Polysorbate 80 (Tween ® 80).

| Test Sample | Vials with Particle Formation After | | | |
|---|---|---|---|---|
| | 7 days | 14 days | 21 days | 28 days |
| Insulin glargine + 0.001 mg/mL polysorbate 20 | No | Yes | Yes, particles increasingly occur | Yes, particles increasingly occur |
| Insulin glargine + 0.010 mg/mL polysorbate 20 | No | No | No | no |
| Insulin glargine + 0.001 mg/mL polysorbate 80 | No | Yes | Yes, particles increasingly occur | Yes, particles increasingly occur |
| Insulin glargine + 0.010 mg/mL polysorbate 20 | No | No | No | No |

An addition of polysorbate 20 or of polysorbate 80 in a concentration of 0.001 mg/ml are equally able to stabilize the solution against particle formation during the in use period.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient Example 14

Confirmation of Stability and Activity of RAMUCIRUMAB

In a particular embodiment, the pharmaceutical composition comprises RAMUMCIRUMAB®. In a particular embodiment, the active pharmaceutical ingredient comprises IMC-1121B. IMC-1121B (RAMUMCIRUMAB®) is a fully human monoclonal (IgG1) anti-VEGFR-2 (flk-1) antibody. It has been hypothesized that treatment with IMC-1121B (RAMUMCIRUMAB®) can help prevent angiogenesis associated with tumor growth.

To determine the stability of ramucirumab (IMC-1121B), samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of IMC-1121B (RAMUMCIRUMAB®) is determined using methods and controls appropriate for the agent, for example, using methods provided in US Patent publication US 2009/0306348, the contents of which are incorporated by reference herein, and from which the below examples are adapted.

Detailed descriptions of conventional methods, such as those employed in the analysis of proteins can be obtained from numerous publications such as *Current Protocols in Immunology* (published by published by John Wiley & Sons). All references mentioned herein are incorporated in their entirety.

Fragmentation of Anti-VEGFR-2 Antibody, IMC-1121B

IMC-1211B at 5 mg/mL in phosphate-buffered saline (PBS) was incubated at 40° C. for 3 months. Following this incubation, SEC-HPLC and N-terminal sequencing were used to analyze the degradation products. The degraded product has two degradant peaks (fractions 2 and 3) in addition to aggregate (fraction 1) and monomer peaks. The fractions were collected using a fraction collector for N-terminal sequence analysis. Signal sequence, variable regions and constant regions are shown with underlined, double-underlined and plain text, respectively. N-terminal sequencing analysis of the degraded sample and fractions 2 and 3 has shown two sites of fragmentation in the heavy chain. The site at the $156^{th}$ residue from the N-terminus results in two heavy chain fragments detected on reduced SDS-PAGE as about 40 KD and about 15 KD bands. The other fragmentation site in the hinge region at the $220^{th}$ residue from the N-terminus results in about 33 KD and about 27 KD bands on reduced SDS-PAGE.

Optimization of Buffer Formulation

The freeze-dried formulation for IMC-1121B was developed in two stages. In the first stage, the solvent buffer was optimized using a design of experiment approach (DOE) with fractional factorial modeling as outlined in Table 29, below. The factors screened in this optimization process were buffer, pH, salt, amino acids, surfactants sugars, and sugar derivatives. Solvent optimization was performed at a 1121B concentration of 5 mg/mL. Controlled agitation at 300 rpm at room temperature was used to test mechanical stability. Thermal stability was tested using DSC and accelerated temperatures. The DOE predictions were confirmed using traditional one-factor-at-a-time methodology. Linear regression analysis was used to determine the significance of the results.

TABLE 29

Design of Experiment (DOE) Matrix

| Buffer Type | pH | NaCl (mM) | Aspartic Acid (%) | Lactobionic acid (%) | Tween 80 (%) | Glycine (%) | Arginine (%) | Mannitol (%) | Sucrose (%) | Trehalose (%) |
|---|---|---|---|---|---|---|---|---|---|---|
| Citrate | 6 | 150 | 0 | 0 | 0.5 | 2 | 2 | 2 | 0 | 0 |
| Citrate | 4 | 0 | 0.5 | 0 | 0 | 2 | 2 | 0 | 0 | 2 |
| Citrate | 4 | 0 | 0.5 | 0.5 | 0.5 | 0 | 0 | 2 | 2 | 0 |
| Citrate | 6 | 150 | 0 | 0.5 | 0 | 0 | 0 | 0 | 2 | 2 |
| Citrate | 5 | 75 | 0.25 | 0.25 | 0.25 | 1 | 1 | 1 | 1 | 1 |
| Acetate | 6 | 0 | 0 | 0.5 | 0.5 | 2 | 0 | 0 | 0 | 0 |
| Acetate | 5 | 75 | 0.25 | 0.25 | 0.25 | 1 | 1 | 1 | 1 | 1 |
| Acetate | 4 | 150 | 0.5 | 0.5 | 0 | 2 | 0 | 2 | 0 | 2 |
| Acetate | 6 | 0 | 0 | 0 | 0 | 0 | 2 | 2 | 2 | 2 |
| Acetate | 4 | 150 | 0.5 | 0 | 0.5 | 0 | 2 | 0 | 2 | 0 |
| Histidine | 7 | 75 | 0.25 | 0.25 | 0.25 | 1 | 1 | 1 | 1 | 1 |
| Histidine | 8 | 0 | 0.5 | 0 | 0.5 | 2 | 0 | 0 | 2 | 2 |
| Histidine | 5 | 150 | 0 | 0.5 | 0.5 | 0 | 2 | 0 | 0 | 2 |
| Histidine | 6 | 150 | 0 | 0 | 0 | 2 | 0 | 2 | 2 | 0 |
| Histidine | 8 | 0 | 0.5 | 0.5 | 0 | 0 | 2 | 2 | 0 | 0 |
| Phosphate | 7 | 75 | 0.25 | 0.25 | 0.25 | 1 | 1 | 1 | 1 | 1 |
| Phosphate | 8 | 150 | 0.5 | 0.5 | 0.5 | 2 | 2 | 2 | 2 | 2 |
| Phosphate | 6 | 0 | 0 | 0.5 | 0 | 2 | 2 | 0 | 2 | 0 |
| Phosphate | 6 | 0 | 0 | 0 | 0.5 | 0 | 0 | 2 | 0 | 2 |
| Phosphate | 8 | 150 | 0.5 | 0 | 0 | 0 | 0 | 0 | 0 | 0 |
| PBS | 7.2 | 145 | 0 | 0 | 0 | 0 | 0 | 0 | 0 | 0 |

Differential Scanning Calorimetry (DSC) Study:

The melting, or transition, temperature (Tm) was measured using a MicroCal VP-DSC. The protein concentration was set at 5 mg/mL and temperature ramping was from 5° C. to 95° C. at a scan rate of 1.5° C./min. The thermal melting curves of IMC-1121B in various formulations (Table 29) were collected. The melting temperatures corresponding to the main transition peak (50% of the molecules are denatured) were fitted to a linear regression model to estimate the effect of tested variables on Tm. The model was statistically significant with a p=0.0006. The significant factors (p<0.05) were pH and buffer type. The optimal pH was approximately 6.0 for the histidine, citrate and acetate buffers, which were superior to phosphate buffer at pH 6.0. Other variables did not have statistically significant effect on Tm.

Agitation Study:

Antibody solutions were agitated on a platform shaker at 300 rpm at room temperature. Five mL of IMC-1121B at 5 mg/mL in a 20 mL glass vial was agitated in various formulations (Table 29) for up to 84 hours. Solution turbidity, percent monomer, percent aggregate, and percent degradant were determined as follows. Solutions turbidity was measured by absorbance at 350 nm using Shimatzu 1601 biospec spectrophotometer. Percent monomer, percent aggregate, and percent degradant were measured using SEC-HPLC performed on an Agilent 1100 Series LC using Tosoph Biosep TSK 3000 column with 10 mM sodium phosphate, 0.5M CsCl, at pH 7.0 as the mobile phase. The effect of tested variables on turbidity, percent monomer, aggregate and degradant were estimated by fitting to a linear regression model using JMP software (SAS institute, NC). The p-value for the Actual by Predicted plot was <0.002.

Real-Time, Accelerated Temperature Stability at 40° C.:

The IMC-1121B at 5 mg/mL in various formulations (Table 29) were incubated at 40° C. for up to 14 days. The solution turbidity, percent monomer, aggregate and degradant were determined as described above. The effect of tested variables on turbidity, percent monomer, aggregate and degradant were estimated by fitting it to a linear regression model using JMP software. The p value for Actual by Predicted plots were <0.001. The optimal buffer is histidine at pH 6.0. Salt reduced monomer and increased aggregation. But did not affect degradation. Glycine has no effect on monomer, aggregate or degradant.

Real-Time Freezing Temperature Stability at −20° C.:

The IMC-1121B antibody at 5 mg/mL in various formulations (Table 29) were incubated at −20° C. for up to 16 days. The solution turbidity, percent monomer, aggregate and degradant was estimated as described above. The effect of tested variables on turbidity, percent monomer, aggregate and degradant were determined by fitting to a linear regression model using JMP software. The p-value for Actual by Predicted plot was <0.001. The optimal pH was 6.0. Aspartic acid increased monomer and decreased aggregation with a negligible effect on degradation. NaCl and glycine had negligible effect on turbidity, monomer, aggregate and degradant.

Comparison of IMC-1121B Stability in PBS and 10 mM Histidine Buffer (pH 6.0) Formulations DOE screening studies predicted that the IMC-1121B antibody has significantly better stability in a 101 mM histidine buffer (pH 6.0) formulation than in PBS. In this study, the stability of IMC-1121B at 5 mg/mL concentration in 10 mM histidine pH 6.0 and PBS was examined by various techniques to confirm the DOE prediction.

Differential Scanning Calorimetry (DSC) Study:

Thermal stability of IMC-1121B in PBS and 10 mM histidine buffer (pH 6.0) formulations were examined according to known methods. The melting temperatures for main transition were 70.0 and 76.6° C. for IMC-1121B in PBS and 10 mM histidine buffer (pH 6.0), respectively.

Real-Time Accelerated Temperature Stability at 40° C. and Room Temperature:

The IMC-1121B at 5 mg/mL was incubated at 40° C. and room temperature (RT) for up to 150 days in PBS and 10 mM histidine buffer (pH 6.0) formulations. Following incubation, the samples were analyzed by SEC-HPLC, IEC-HPLC, SDS-PAGE and IEF as described below.

SEC-HPLC Analysis:

The SEC-HPLC analysis of IMC-1121B in PBS or 10 mM histidine buffer (pH 6.0) following 150 days of incubation at 40° C. and room temperature was performed according to procedure described above. The total percent of aggregate in control, RT and 40° C. samples was 0.90, 1.49 and 3.90 for PBS and 0.80, 0.82 and 0.75 for 10 mM histidine buffer (pH 6.0), respectively. The total percent degradant in control, RT and 40° C. samples was 1.32, 2.56 and 12.54 respectively, for PBS and 1.23, 2.09 and 9.00 for 10 mM histidine buffer pH 6.0 formulations, respectively. Percent monomer decreased and percent aggregate and percent degradant increased at faster rate in PBS formulation than 10 mM histidine (pH 6.0). The 10 mM histidine buffer (pH 6.0) provides a superior environment for maintenance of the IMC-1121B antibody as IEC-HPLC Analysis:

Ion exchange chromatography of IMC-1121B following 30 and 150 days of incubation at 40° C. and room temperature was performed on an Agilent 1100 Series LC using a Dionex ProPac WCX-10 analytical column. The samples were eluted with a linear gradient from 10 mM phosphate (pH 7.0), 20 mM NaCl to 10 mM Phosphate (pH 7.0), 100 mM NaCl in 32 minutes. Incubation at room temperature and 40° C., caused the peaks to shift toward lower retention time (i.e. toward acidic pH) in both formulations. However, the shifts were considerably larger in the PBS formulation than in 10 mM histidine buffer (pH 6.0) formulation.

SDS-PAGE Analysis:

The IMC-1121B antibody (at 5 mg/mL) in PBS or 10 mM histidine buffer (pH 6.0) was incubated at room temperature or 40° C. for 150 days prior to analysis by reducing and non-reducing SDS-PAGE (4-20% tris-glycine gradient gel) according to standard protocols. The samples incubated in PBS had greater amounts of degradation products that the samples incubated in 10 mM histidine (pH 6.0) as measured by the intensity of the bands.

Isoelectric Focusing (IEF) Analysis:

IMC-1121B at 5 mg/mL in PBS and 10 mM histidine (pH 6.0) formulations after 150 days of incubation at RT and 40° C. was analyzed by IEF (pH range 6.0-10.5). Isoelectric focusing analysis was performed on IsoGel® Agarose IEF plates with a pH range from 6.0 to 10.5. The resulting bands migrated towards acidic pH both in PBS and histidine formulations. However, the shift was greater for the PBS formulation than for the 10 mM histidine (pH 6.0) formulation.

Freeze-Drying Formulation Screening

In the second stage of optimization, bulking agents and cryo- and lyo-protectants were optimized at a fixed antibody concentration of 20 mg/mL in 10 mM histidine buffer (pH 6.0). The additives tested were mannitol, glycine, sucrose and trehalose as shown in the design of experiment matrix (Table 30). As controls, IMC-1121B antibody at the concentration of 5 mg/mL in solution formulations (without freeze-drying) with PBS buffer (pH 6.0) or 10 mM histidine buffer (pH 6.0) was analyzed.

TABLE 30

DOE Matrix for Freeze-dried Formulation Screening

| IMC-1211B (mg/mL) | Sucrose (%) | Teahouse (%) | Glycine (%) | Mannitol (%) |
|---|---|---|---|---|
| 20 | 4 | 0 | 0 | 0 |
| 20 | 0 | 4 | 0 | 0 |
| 20 | 0 | 0 | 4 | 0 |
| 20 | 0 | 0 | 0 | 4 |
| 20 | 2 | 0 | 2 | 0 |
| 20 | 2 | 0 | 0 | 2 |
| 20 | 0 | 2 | 2 | 0 |
| 20 | 0 | 20 | 0 | 2 |

Freeze-Drying Process:

The products were lyophilized using a Lyostar II freeze-dryer. The lyophilzaion tray was loaded with sample at room temperature. Products were soaked at −50° C. for 2 hours. Primary drying was performed at −30° C. for 10 hours followed by secondary drying at 20° C. for another 10 hours. The cooling and heating rates were 0.5° C./min Chamber pressure during primary and secondary drying was 50 mT. Once lyophilization was completed, the sample chamber was backfilled with $N_2$ and capped. The lyophilization process was completed in about 24 hours. The lyophilization process was considered completed when product temperature reached (or crossed) the shelf set temperature.

Accelerated Temperature Stability:

The lyophilized antibody formulations were incubated for 100 days either at 40° C. or 50° C. After the incubation period, products were reconstituted to 5 mg/mL with 10 mM histidine buffer (pH 6.0). The reconstitution time was less than 1 min. The freeze-dried formulations with 4% sucrose or 4% trehalose retained the highest percentage of monomer after the 100 day incubations at 40° C. and 50° C.

Accelerated Temperature Stability Comparison Between Freeze-Dried and Solution Formulations:

The freeze-dried formulations: (1) 20 mg/mL IMC-1121B, 4% sucrose, 10 mM histidine buffer (pH 6.0), and (2) 20 mg/mL IMC-1121B, 4% trehalose, 10 mM histidine buffer (pH 6.0), was compared with solution formulations (1) 5 mg/mL IMC-1121B in PBS (pH 7.2) and (2) 5 mg/mL IMC-1121B in 10 mM histidine buffer (pH 6.0). The samples were incubated at 40° C. or 50° C. for up to 100 days. After incubation period, the lyophilized products were reconstituted to 5 mg/mL with 10 mM histidine buffer (pH 6.0). The reconstituted lyophilized samples and the solution samples were analyzed by SEC-HPLC. Percent degradation increased with time in both the solution formulations but it remained unchanged in lyophilized formulations.

Freeze-Drying Formulation for High Concentration Antibody

The previous results demonstrated that of the compounds tested, 4% sucrose or 4% trehalose provides the greatest stability for freeze-dried formulations of the IMC-1121B antibody at concentrations of 20 mg/mL. In this study we have raised IMC-1121B concentration from 20 mg/mL to 50 mg/mL and varied sucrose concentration from 4% to 8% with the goal of to formulating an IMC-1121B at a concentration of 50 mg/mL. As a control, IMC-1121B at 20 mg/mL in the presence of 4% sucrose was also lyophilized. The lyophilized products and control solution formulation were incubated at room temperature, 40° C. and 50° C. for up to 3 months. The control solution formulation consisted of the optimized, current recommended solution formulation for the IMC-1121B antibody (5 mg/mL in 10 mM histidine, 133 mM Glycine, 75 mM NaCl, 0.01% Tween 80). Following the incubation period, lyophilized products were reconstituted to 5 mg/mL with 10 mM histidine buffer (pH 6.0) and then analyzed by SEC-HPLC, IEC-HPLC, and reducing and non-reducing SDS-PAGE.

SEC-HPLC Analysis of Lyophilized and Solution Formulated IMC-1121B after 50° C. Incubation:

SEC-HPLC was performed on samples before and after lyophilization and following one month and 3 month incubations at 50° C. Following the incubation, the lyophilized products were reconstituted with 10 mM histidine (pH 6.0). The percent monomer was largest and aggregate was smallest for 8% sucrose sample. Lyophilized samples contained significantly less degradants than the solution formulated samples.

SEC-HPLC and IEC-HPLC Analysis of Lyophilized and Solution Formulated IMC-1121B after Incubation at Room Temperature and at 40° C.:

SEC-HPLC and IEC-HPLC were performed on samples before and after lyophilization and following one month and 3 month incubations at room temperature and 40° C. Following the incubation, the lyophilized products were reconstituted with 10 mM histidine buffer (pH 6.0). Lyophilized samples contained significantly less degradants than the solution formulated samples. A reference IMC-1121B sample was included for comparison. The chromatogram of the freeze-dried sample is similar to the reference IMC-1121B, but the chromatogram for solution formulated IMC-1121B was shifted toward acidic pH.

SDS-PAGE Analysis of Lyophilized and Solution Formulated IMC-1121B after a 3 Months Incubation:

The lyophilized products were reconstituted into 10 mM histidine buffer (pH 6.0). IMC-1121B maintained in solution, and IMC-1121B reconstituted freeze-dried samples in 10 mM histidine buffer (pH 6.0) were analyzed with a 4-20% reducing SDS-PAGE and a 4-20% non-reducing SDS-PAGE following a three month incubation. The lyophilized formulations, 20 mg/ml antibody with 4% sucrose and 50 mg/ml antibody with 8% sucrose, displayed significantly reduced heavy chain degradation in comparison with the non-lyophilized formulation.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient Example 15

Confirmation of Stability and Activity of SOLANEZUMAB

LY2062430 (SOLANEZUMAB®) is a humanized, monoclonal, anti-β-amyloid antibody. It binds to the central region of β-amyloid, and it has been hypothesized that treatment with LY2062430 may help reduce the symptoms associated with diseases such as Alzheimer's and dementia. SOLANEZUMAB has a molecular formula of $C_{6396}H_{9922}N_{1712}O_{1996}S_{42}$ and a molecular weight of 144.08 kDa.

To determine the stability of LY2062430 (SOLANEZUMAB®), samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of LY2062430 (SOLANEZUMAB®) is determined using methods and controls appropriate to the agent.

Affinity Determination

To assess the binding specificity and affinity of LY2062430, BIACORE® analysis is performed using amyloid beta 1-42 monomers and fibers as antigen immobilized on a CM5 chip. BIACORE® technology utilizes changes in the refractive index at the surface layer upon binding of the antibody to the antigen immobilized on the layer. Binding is detected by surface plasmon resonance (SPR) of laser light refracting from the surface. Analysis of the signal kinetics on rate and off rate allows the discrimination between non-specific and specific interaction. The concentration of antibody used is in the range of 0.05 µM to 1.0 µM.

Immunohistochemical Binding Assay 11.1 Human Brain Sections:

Brains from healthy, non-demented pre-AD and AD patients are obtained from the Universitatsklinik in Bonn after ethical approval. Brains are fixed in formaldehyde and the hippocampus region is dehydrated, embedded in paraffin and 5 µm sections are cut with a microtome. Paraffin sections are stored at RT until use. For fresh material, 5 µm cryosections are cut with a cryostat and sections stored at −80° C. until use.

11.2 Immunohistochemistry:

Paraffin sections are deparaffinized and rehydrated by bathing slides in xylene followed by 100% ethanol, 90% ethanol and 70% ethanol. Background is decreased by 30 minutes incubation in 110% $H_2O_2$, 10% methanol in water. Antigen retrieval is obtained by incubating the slides in 100% formic acid for 3 minutes. After 3 washes in Tris buffered saline (TBS, pH 7.5), non-specific labeling is blocked by a 2 hour incubation of the slides in 10% BSA, 0.25% Triton X-100 in TBS. After washing (3 washes in TBS) blocking of endogenous antibodies is performed by adding a non-labeled anti-human IgG (Biomeda) and incubating slides in humid chambers overnight at RT. After another 3 washes, the primary human anti amyloid antibody is added to the slides and incubated another 24 hours at RT. Following washing, an alkaline phosphatase labeled secondary anti human IgG (Sigma) is added to the slides and incubated for 2 hours at RT. After washing, slides are developed with Liquid permanent Red (Dakocytomation) washed with water and air-dried before mounting with permanent mounting media (corbitbalsam).

Cryosection are fixed in methanol for 30 minutes at −80° C. and background decreased by adding $H_2O_2$ to the cold methanol to a final concentration of 10% and incubating for 30 minutes at RT. After 3 washes in Tris buffered saline (TBS, pH7.5), non-specific labeling is blocked by a 2 hour incubation of the slides in 10% BSA, 0.25% Triton X 100 in TBS as above and the same staining procedure as above is carried out.

Sections are examined with a Leica DMLB microscope and photographed using a Leica DC500 camera and Leica FireCam1.2.0 software.

LY2062430 is expected to label plaques of brains from AD disease patients. It is also expected to label both diffuse and cored plaques. Moreover, diffuse plaques in non-demented pre-AS patients are also expected to be detected by LY2062430. Amyloid in cerebral amyloid angiopathy (CAA) is labeled with LY2062430 and some staining of neurons which may correspond to intracellular amyloid can also be detected. No labeling is expected on control brains from healthy patient. Plaques can be detected on paraffin sections pretreated with formic acid but no plaques are labeled on paraffin sections without formic acid pretreatment and on cryosections fixed in methanol. LY2062430 is not expected to detect plaques on paraffin sections.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient Example 16

Confirmation of Stability and Activity of IXEKIZUMAB

In a particular embodiment, the pharmaceutical composition comprises IXEKIZUMAB®. In a particular embodiment, the active pharmaceutical ingredient comprises LY2439821. LY2439821 is a humanized anti-IL-17 (IL-17A) monoclonal antibody characterized as having a high affinity and slow off rate for human IL-17.

LY2439821 (IXEKIZUMAB®) is characterized by a strong binding affinity ($K_D$) for human IL-17, i.e., less than about 7 pM, 6.5 pM, 6.0 pM, 5.5 pM, 5.0 pM, 4.5 pM or 4.0 pM. Alternatively, LY2439821 is characterized by a $K_D$ for human IL-17 of no greater than about 7 pM, 6.5 pM, 6.0 pM, 5.5 pM, 5.0 pM, 4.5 pM or preferably no greater than about 4.0 pM. Preferably LY2439821 (IXEKIZUMAB®) is further characterized with a $k_{off}$ rate from human IL-17 of less than $2 \times 10^{-5}$ $s^{-1}$. LY2439821 has a molecular formula of $C_{6492}H_{10012}N_{1728}O_{2028}S_{46}$ and a molecular weight of 146.2 kDa.

To determine the stability of LY2439821 (IXEKIZUMAB®), samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of LY2439821 (IXEKIZUMAB®) is determined using methods and controls appropriate to the agent, for example, using methods provided in U.S. Pat. No. 7,838,638; U.S. Pat. No. 8,110,191; and US Patent publications US 2008/0269467; and US 2011/0027290; the entire contents of which are incorporated by reference herein and from which the below examples are adapted.

ELISA I: Antibody Binding to IL-17 of Various Species (Adapted from U.S. Pat. No. 8,110,191)

An exemplary ELISA assay for measuring binding of antibodies to IL-17 uses sealed Costar 3366 microtiter plates that are coated overnight at 4° C. with 50 µl of 1.0 µg/ml human IL-17 per well (R&D Systems, #317-IL/CF) in carbonate coating buffer (50 mM sodium carbonate, pH 9.0). Alternatively, mouse, rat, rabbit or cynomolgus monkey IL-17 are used. Human IL-22 (R&D Systems) is used as a control antigen. Rabbit and cynomolgus monkey IL-17 are not commercially available and therefore require cloning and expression, or artificial synthesis, according to methods known in the art making use of the amino acid sequences for IL-17 of the various species.

The plate is subsequently blocked by adding 100 µl blocking buffer (Pierce #37515). The plate is incubated for 1 hour at 37° C. then washed three times in wash buffer (PBS pH 7.4 and 0.05% Tween). Then, 50 µl of either sample antibody or control antibody (diluted to various concentrations in PBS pH 7.4, e.g., 2, 0.4, 0.08, 0.016, 0.0032 and 0 µg/ml) is added to each well and the plate is further incubated for 1 hour at 37° C. The plate is then washed three times with wash buffer before adding 50 µl per well of anti-human kappa-alkaline phosphatase conjugated diluted to 1:1000 in PBS pH 7.4. The test samples are incubated for 1 hour at 37° C. Then p-nitrophenyl phosphate disodium salt (PNPP, Pierce #37620) is freshly made by dissolving in diethanolamine substrate buffer according to manufacturer's instruction and 50 µl is added to each well. Color development is allowed to proceed for about 10 minutes at room temperature then color signal is measured at an absorbance of 405 nm using any appropriate ELISA plate reader. The degree of binding is proportional to color signal production.

Antibodies of the invention bind human IL-17 in an ELISA assay as described herein, but do not bind rat or mouse IL-17. It is anticipated, given the Biacore data of the example "Measuring Binding Kinetic Constants" (see below) demonstrating that antibodies of the invention bind human and monkey IL-17, that the antibodies of the invention would also demonstrate binding to monkey IL-17 in an ELISA assay as described herein.

ELISA II: Antibody Binding to Proteins of IL-17 Family

An ELISA is used to measure whether antibodies of the invention selectively and/or preferentially bind particular human IL-17 members (e.g., IL-17A, IL-17B, IL-17C, IL-17D, IL-17E or IL-17F) or human IL-22 (negative control).

In an exemplary assay, ELISA plate wells (Nunc Immuno Maxisorp) are coated with 100 µl (0.5 ng/ml in 1× coating buffer (BioFx)) of IL-17 family member proteins (R&D Systems) sealed and incubated overnight at 4° C. The solution in the well is removed by flicking and blocking buffer (200 µl 1.5% BSA in PBS) is added. The plates are incubated on a rotating shaker for 30 minutes at room temperature. Then 100 µl of an antibody to be tested is added per well at varying concentrations (e.g., 2, 0.4, 0.08, 0.016, 0.0032 and 0 µg/ml). The plates are again incubated overnight (4° C.) followed by warming on a rotating shaker (60 min room temp). Each plate-well is then washed five times with buffer (1× Ish buffer, BioFX). After washing, an appropriate commercially available HRP-conjugated secondary antibody (1:2000 in PBS with 1.5% BSA) is added (100 µl/well). Plates are re-incubated on a rotating shaker (60 min. room temp.) followed by buffer washing (5×) as described above. The colorimetric signal is developed by adding TMB (100 µl/well) until saturation (approx 3-5 min.) then further development is ended by adding stop solution (100 µl/well, BioFX). The color signal is measured at 450 nm absorbance using any appropriate ELISA plate reader. The degree of binding is proportional to color signal production. Antibodies of the invention specifically bind human IL-17 (i.e., IL-17A), but, under similar conditions, do not bind at greater than background levels to human IL-17B, human IL-17C, human IL-17D, human IL-17E, human IL-17F, murine IL-17 or human IL-22.

Measuring Binding Kinetic Constants

A BIACORE® 2000 instrument is used to measure antigen-antibody binding kinetics and affinity. The instrument utilizes the optical properties of surface plasmon resonance to detect alteration in protein concentration of interacting molecules within a dextran biosensor matrix. Except as noted, all reagents and materials are purchased from BIACORE® AB. All measurements are performed at 25° C. Samples are resuspended in HBS-EP buffer to a final concentration of 2 µg/ml (150 mM sodium chloride, 3 mM EDTA, 0.005% (w/v) surfactant P-20, and 10 mM HEPES, pH 7.4). A protein is immobilized on flow cells 1 to 4 of a CM4 sensor chip at a level of 500 response units using an amine coupling kit.

Binding is evaluated using multiple analytical cycles. Each cycle is performed at a flow rate of 50 µl/minute and consists of the following steps: injection of about 20 µl of an antibody composition at 2 µg/ml aiming at a capture of 100-200 response units, injection of 250 µl of human IL-17, Cynomalgus monkey IL-17, New Zealand white rabbit IL-17, rat IL-17 or mouse IL-17 (starting at 10 nM and using two-fold serial dilutions for each cycle) followed by 20 minutes for dissociation, and regeneration using 30 µl of 10 mM glycine hydrochloride, pH 1.5. Association and dissociation rates for each cycle are evaluated using a "1:1 with mass transfer" binding model in the BIAevaluation software.

Full-length representative mAbs 103, 104, 118, 121, 126 and 131 having an IgG4 Fc region exhibit high affinity binding to human IL-17 and to monkey IL-17 with a $K_D$ less than 5 pM, a $K_{off}$ slower than $2 \times 10^{-5} s^{-1}$ and a $K_{on}$ of at least $5 \times 10^6 M^{-1} s^{-1}$. The $K_D$ and $k_{off}$ are improved (i.e., lower $K_D$, slower $k_{off}$) in these variant mAbs over Fab 2321 mAb (parent Fab of e.g., Fab 103 and 104) comprising a murine variable region [(VH of 2321), (VL of 2321) (see e.g. U.S. Pat. No. 8,110,191)], a human IgG4 heavy chain constant region and a kappa light chain constant regions. Antibodies of the invention exhibit binding no greater than background levels to mouse IL-17 or rat IL-17; no binding is detected up to 200 nM mouse IL-17 and no binding is detected up to 1 nM rat IL-17. When the full-length mAbs 103, 104, 121 and 126 are tested, under the same conditions described above, for binding to cynomolgus monkey IL-17 and rabbit IL-17; binding to rabbit IL-17 is weak and biphasic while binding to monkey IL-17 is similar to binding to human. Specific values for certain mabs (values are reported as mean±standard error of mean) of the invention when tested in this assay are listed in Table 31 below. It is contemplated that Fc regions other than that of IgG4 would not significantly affect $K_D$ and $k_{off}$.

TABLE 31

| | $K_{on}$ ($M^{-1} s^{-1}$) | $K_{off}$ ($s^{-1}$) | $K_D$ (pM) |
|---|---|---|---|
| Human IL-17 | | | |
| mAB 103 | 11(±2) × $10^6$ | 1.5 ± 0.7) × $10^{-5}$ | 1.4 (±0.7) |
| mAB 104 | 7.7 (±0.6) × $10^6$ | 1.1 (±0.5) × $10^{-5}$ | 1.7 (±0.9) |
| mAb 118 | 5 × $10^6$ | 2 × $10^{-5}$ | 3.9 |
| mAb 121 | 10 (±0.9) × $10^6$ | 1.5 (±0.3) × $10^{-5}$ | 1.6 (±0.4) |
| mAb 126 | 7.5 (±0.4) × $10^6$ | 1.3 (±0.25) × $10^{-5}$ | 1.8 (±0.3) |
| mAb 131 | 5.4 × $10^6$ | 1.6 × $10^{-5}$ | 2.9 |
| Parent 2321 mAb | 2.7 × $10^6$ | 6 × $10^{-5}$ | 7 |
| CYNO IL-17 | | | |
| mAB 103 | 8.8 × $10^6$ | 1.1 × $10^{-5}$ | 1.3 |
| mAB 104 | 9.4 × $10^6$ | 0.5 × $10^{-5}$ | 0.5 |
| mAb 121 | 7.8 (±0.3) × $10^6$ | 0.7 (±0.2) × $10^{-5}$ | 1.1 (±0.04) |
| mAb 126 | 7.9 (±0.3) × $10^6$ | 0.7 (±0.6) × $10^{-5}$ | 0.8 (±0.8) |

TABLE 31-continued

| | $K_{on}$ (M$^{-1}$ s$^{-1}$) | $K_{off}$ (s$^{-1}$) | $K_D$ (pM) |
|---|---|---|---|
| Rabbit IL-17 | | | |
| mAB 103 | $1.8 \times 10^5$ | $3.6 \times 10^{-4}$ | 2 |
| | $106 \times 10^6$ | $19.2 \times 10^{-2}$ | 18.1 |
| mAB 104 | $1.0 (\pm 0.1) \times 10^5$ | $1.8 (\pm 1.0) \times 10^{-4}$ | $1.9 (\pm 1.3)$ |
| | $4.0 (\pm) \times 10^6$ | $7.0 (\pm 2) \times 10^{-2}$ | $20 (\pm 6)$ |
| mAb 121 | $8 (\pm 6) \times 10^5$ | $4 (\pm 3) \times 10^{-4}$ | $0.51 (\pm 0.13)$ |
| | $17 (\pm 11) \times 10^6$ | $2.1 (\pm 0.2) \times 10^{-2}$ | $1.5 (\pm 1.0)$ |
| mAb 126 | $1.5 (\pm 0.6) \times 10^5$ | $1.7 (\pm 0.5) \times 10^{-4}$ | $1.3 \pm 0.6)$ |
| | $9 (\pm 3) \times 10^6$ | $11 (\pm 2) \times 10^{-2}$ | $14 (\pm 4.0)$ |

IL-17 Receptor/Anti-IL-17 Antibody Binding Competition Studies

This example demonstrates that the antibodies of the invention compete for binding to IL-17 with the IL-17 receptor.

BIACORE binding studies are performed using the IL-17 receptor Fc-fusion protein (R&D #177-IR). To demonstrate that it binds human IL-17, a BIACORE assay is performed in BIACORE binding buffer (HBS-EP)+1 mg/ml BSA at 25° C. on a BIACORE 2000 instrument. A CM4 chip is used with approximately 600 response units of Protein A immobilized on flow cells 1, 2 and 3 of the chip. Approximately 100 response units of IL-17 receptor Fc-fusion protein is captured on flow cell 2 of the chip. Human IL-17 is then exposed to flow cells 1 and 2 in concentrations ranging from 600 nM to 9.4 nM. After each 250 μl injection of human IL-17, the complex is allowed to dissociate for about 12 minutes by running buffer across the chip. At the end of the dissociation, a 20 μl injection of 100 mM glycine pH 1.5 is used to regenerate the chip before the next cycle of binding begins. Flow cell 1 is used as a reference flow cell. The data is fit using the "Bivalent analyte" model in the BIAevaluation Version 3.2 software. The results indicate that this interaction has an on-rate of $1.06 \times 10^5$ M$^{-1}$s$^{-1}$, a fast off-rate of 20.3 s$^{-1}$ and a slow off-rate of $1.63 \times 10^{-4}$ s$^{-1}$. Therefore, this interaction has a $K_D$ or binding affinity of 1.5 nM and 0.19 mM which is much weaker than the binding affinities of the antibodies of the invention to human IL-17.

Binding for the competition experiment is also measured in HBS-EP+1 mg/ml BSA at 25° C. on a BIACORE 2000 instrument with a CM4 chip. Approximately 1000 response units of an antibody of the invention is immobilized on flow cells 2, 3 and 4 of the chip; flow cell 1 is left blank. Using a flow rate of 50 μl/ml, 25 μl of 500 nM human IL-17 is injected over all four flow cells, forming the antibody:antigen complex on the surface of the chip. After the injection is complete and the complex formed, 250 μl of 500 nM human IL-17 receptor Fc fusion protein is injected over all four flow cells. At the end of this injection a 25 μl injection 100 mM glycine pH 1.5 is used to regenerate the chip. The same binding experiment is then repeated using a 250 μl injection of buffer rather than IL-17 receptor Fc fusion protein.

The binding profiles for both the receptor injection over the antibody:antigen complex and for the buffer control injection over the antibody:antigen complex are identical. This indicates that there are no binding sites available for the dimeric IL-17 to bind to its receptor once it is bound to an antibody of the invention. This result also indicates that the receptor is not able to "pull" IL-17 away from any of the antibodies once the complex is formed. These antibodies can inhibit human IL-17 from binding to its receptor, therefore neutralizing biological activity of human IL-17.

In Vitro IL-8 Reporter Assay

To test the ability of an antibody of the invention to neutralize or antagonize an IL-17 bioactivity, one can utilize the IL-8 reporter assay described herein. This approach can also be used to determine the potency of Fabs or mAbs of the invention in a cell-based assay. The human HS27 cell line (ATCC #CRL-1634) secretes IL-8 in response to IL-17. The IL-17-induced IL-8 secretion is inhibited by neutralizing anti-IL-17 antibodies (See, e.g., J. Imm. 155:5483-5486, 1995 or Cytokine 9:794-800, 1997). Accordingly, IL-17-induced IL-8 secretion should proceed unconstrained if sufficient IL-17 is added to HS27 cells in the absence of neutralizing anti-IL-17 antibody.

HS27 cells are maintained in assay medium: DMEM high glucose medium lacking phenol red (Invitrogen #31053-028) with 10% fetal bovine serum, 4 mM L-glutamine, 1 mM sodium pyruvate, penicillin G (100 U/500 ml) and streptomycin (100 mg/500 ml). Cells are grown in T150 flasks until they are about 80-90% confluent the day of the assay. Human IL-17 (R&D Systems, #317-IL-050) is reconstituted in sterile PBS without Ca$^{2+}$ and Mg$^{2+}$ stored frozen, freshly thawed for use and diluted to 200 ng/ml in assay medium. A 50 μl aliquot of the diluted IL-17 is added to each well of a 96-well flat-bottom tissue culture plate (Falcon #35-3072) with the outer wells left empty. Duplicate wells are used for a media-only control (100 μl/well) and IL-17-only control (1000 μl/well). Testing is carried out in duplicate or triplicate. Sterile full-length mAb proteins are diluted to a maximum concentration of 24 μg/ml in assay media. Serial dilutions (typically 1:5) are made in a separate assay plate and 50 μl of the Fab samples at the various dilutions are added to the wells containing IL-17 then incubated at 37° C. for 1 hour. Assay medium alone is used as a negative control.

HS27 cells (typically about 20,000 cells in 100 μl assay medium) are added to each well of the plate containing Fab+IL-17 (or controls) and incubated for about 48 hours at 37° C. The media supernatants are then collected after centrifugation of the 96 well plates for 5 minutes at 500 times gravity and diluted 1:15 or 1:10 in assay media. The level of IL-17 neutralization is measured by determination of IL-8 amounts in supernatant using a commercial ELISA kit according to manufacturer's instruction except assay medium is substituted for standard diluent and substrate volume is 100 μl/well (R&D Systems, ELISA D-8000C or R&D DuoSet ELISA #DY208hIL-8). ELISA measurements (450 nm) are taken on a microplate reader. Calibration curves are obtained using a 4-parameter logistic fit with IL-8 values (pg/ml) determined from the calibration curves using standard statistical techniques. IC$_{50}$ values are obtained using standard statistical techniques.

Full-length mabs 103, 104, 121 and 126 of the invention (with IgG4 Fc region), when tested in the assay described (2-4 replications), have an average IC$_{50}$ (based on an estimated molecular weight of 150 kD for each mAb) of between 450 and 500 pM with the range of all measured values between 365 and 618 pM.

In Vitro GROα Reporter Assay

To test the ability of an antibody of the invention to neutralize or antagonize an IL-17 bioactivity, one can utilize the following cell-based assay. IL-17 can stimulate epithelial cells and other cells to secrete GROα. The ability of an antibody of the invention to neutralize IL-17-induced GROα secretion from the human colorectal adenocarcinoma epithelial cell line HT-29 is tested in this assay.

To test whether human IL-17 dose-dependently induced GROα secretion from HT-29 cells, recombinant IL-17 (R&D Systems #317-IL-050/CF; reconstituted in sterile Dulbecco's PBS without Ca$^{2+}$ and Mg$^{2+}$ (D-PBS)) is diluted (to 4.5 µg/ml; 3× the highest test concentration) in assay/culture medium (McCoy's 5A (Invitrogen); 10% FBS (Invitrogen); penicillin G (100 U/500 ml); and streptomycin (100 µg/500 ml. IL-17 is further diluted serially (1:5) in assay medium. Various concentrations of IL-17 (0.096 ng/ml-1, 500 ng/ml; 3.0 pM-46,875 pM) are dispensed (50 µl each) into inner wells of a tissue-culture treated 96-well plate. Assay medium (50 µl) is dispensed into 3 wells for a "medium alone" treatment. Testing is carried out in triplicate (3 wells per treatment). The plate containing IL-17 in assay medium is incubated for approx. 60-90 minutes at 37° C., 5% $CO_2$, before the addition of HT-29 cells.

For evaluation of an antibody of the invention, a concentration of IL-17 that gave approximately 70% of maximal GROα secretion from HT-29 cells is used (60 ng/ml). Recombinant human IL-17 (R&D Systems) is diluted (to 240 ng/ml; 4× working concentration) in assay/culture medium. Diluted IL-17 is dispensed (50 µl) into 60 separate inner wells of tissue-culture treated 96-well plates (Becton Dickinson Falcon #35-3072). Assay medium (50 µl) is dispensed into 3 wells for a "medium alone" treatment.

A dose range of an antibody of the invention to be tested is typically from 2.56-40,000 pM. In a separate dilution plate, the antibody of the invention and control antibody (sterile, in 1×PBS, pH 7.4) are diluted to 160,000 pM in assay medium. The antibody of the invention and control antibody are further diluted serially (1:5) in assay medium. Each test concentration of the antibody of the invention to be tested is then added (50 µl) to wells containing IL-17. Testing is typically carried out in triplicate. Assay medium alone (50 µl) is used for "medium alone" and "IL-17 alone" controls. Plates containing IL-17 and antibody of the invention mixtures are incubated for 60-90 minutes at 37° C., 5% $CO_2$, before the addition of HT-29 cells.

HT-29 cells (human colorectal adenocarcinoma epithelial cells, ATCC #HTB-38), are maintained in culture/assay medium in tissue culture-treated flasks using standard techniques. HT-29 cells are grown in tissue culture flasks until they were 50-80% confluent on the day of the assay. On the day of the assay, the cells are rinsed with HBSS (Cambrex #CC-5024) and detached from the culture flasks with trypsin+EDTA. The trypsin is inactivated with complete assay medium. HT-29 cells are then centrifuged at 500×g for 5 min. at RT. The cell pellet is then re-suspended in assay medium and 20,000 HT-29 cells (in 100 µl) are added to each treatment well of the 96-well plates. An equal volume of D-PBS is added to each of the unused edge wells (without cells) to reduce edge effects resulting from evaporation. The 96-well plates were placed in a tissue culture incubator (37° C., 5% $CO_2$) for approximately 48 hours.

At the end of the assay, the plates are centrifuged (500×g for 5 min. at RT), and the cell culture media is transferred to polypropylene 96-well plates. GROα levels are measured with a GROα sandwich ELISA (R+D Systems DuoSet #DY275), as per the manufacturer's instructions, except for: using assay medium as the standard diluent, using 1×ELISA wash buffer from BioFX Labs, using a sample and standard volume of 50 µl per well, using a substrate from BioFX Labs (HRP substrate, #TMBW-1000-01), and using a stop solution from BioFX Labs (#LSTP-1000-01) (100 µl per well). At the end of the ELISA reactions, plates are read at 450 nm on a microplate reader. Calibration curves for GROα are obtained by performing a 4-parameter logistic fit. GROα values (concentration in pg/ml) for the samples are obtained from the calibration curves. The human colorectal adenocarcinoma epithelial cell line HT-29 secreted GROα when stimulated with IL-17, in a dose-dependent manner (Table 32). Control human IgG4 did not cause a decrease in IL-17-induced GROα secretion. These results (Table 33) demonstrate that antibodies of the present invention, e.g. mAb 126, is able to completely neutralize human IL-17-induced GROα secretion from HT-29 cells in vitro using the conditions described. The $IC_{50}$ value for mAb 126 in this assay is approximately 560 pM.

TABLE 32

| Human IL-17 (ng/mL) | AVG GROα (pg/mL) | STDEV |
|---|---|---|
| 1500.00 | 2,420.4 | 311.8 |
| 300.00 | 2,047.5 | 509.9 |
| 60.00 | 1,556.0 | 209.0 |
| 12.00 | 960.0 | 24.9 |
| 2.40 | 502.5 | 12.3 |
| 0.48 | 297.9 | 6.3 |
| 0.10 | 205.8 | 4.8 |
| 0 | 149.2 | 16.7 |

TABLE 33

| | mAb 126 | | IgG4 negative control | |
|---|---|---|---|---|
| Antibody Conc., pM | AVG GROα, pg/mL | STDEV | AVG GROα, pg/mL | STDEV |
| 40,000.0 | 123.8 | 1.4 | 1,297.3 | 29.4 |
| 8,000.0 | 134.1 | 6.4 | 1,419.9 | 133.4 |
| 1,600.0 | 151.3 | 9.5 | 1,370.4 | 114.7 |
| 320.0 | 1,170.6 | 56.0 | 1,388.6 | 54.1 |
| 64.0 | 1,340.8 | 59.1 | 1,380.4 | 36.0 |
| 12.8 | 1,362.0 | 21.1 | 1,346.2 | 81.6 |
| 2.56 | 1,280.9 | 56.1 | 1,243.4 | 118.3 |
| 0 (IL-17 alone) | 1,201.4 | 66.1 | | |
| Medium alone | 117.2 | 10.0 | | |

In Vivo Neutralization of hIL-17

Human IL-17 is able to bind and stimulate the mouse IL-17 receptor, leading to an elevation and subsequent secretion of mouse KC (CXCL1) chemokine. Time and dose ranging experiments are undertaken to identify the optimal dose of human IL-17 and the optimal time for induction of mouse KC. These experiments indicate that a 150 µg/kg dose of human IL-17 and a time of 2 hours post IL-17 administration gives maximal levels of KC in mouse serum. Full-length antibodies of the present invention (e.g., Fab 126 or Fab 121 with HCVR operably linked to human IgG4 Fc, and the LCVR operably linked to a human kappa constant region) are administered intravenously to mice at 1, 10, 100 and 1000 µg/kg, one hour prior to a subcutaneous injection of human IL-17. At two hours after human IL-17 administration, the mice are sacrificed and KC levels are determined by ELISA using a commercially available kit according to manufacturer's instruction (KC Quantikine, R&D). Isotype matched antibodies are used as negative controls. The antibodies block the ability of human IL-17 to stimulate the mouse IL-17 receptor, leading to inhibition of an elevation of mouse KC, in a dose dependent manner. Mab126 (a full length antibody comprising Fab 126), at a dose of 20 µg/mouse under the conditions described, decreases the mean KC level by approximately four-fold compared to a control antibody which had no effect. Mab 121, at a dose of 20 µg/mouse under the conditions described, decreases the mean KC level by approximately three-fold compared to a control antibody.

Anti-IL-17 mAb Purification

A vector expressing a mAb of the invention is stably incorporated into an appropriate host cell, (e.g., CHO DG44

(dhfr−) cells (Chasin) or NSO cells) using standard procedures and purified using Protein A affinity column Briefly, clarified conditioned media is applied to a 5 ml HiTrap rProtein A Sepharose FF column (Amersham Biosciences) that has been equilibrated with PBS (pH 7.4). The column is washed with 5 column volumes of equilibration buffer at a flow rate of 110 cm/hr to wash out nonspecific binding components. The bound antibody is eluted using a linear pH gradient (0.1 M sodium phosphate buffer pH 6.8 to 0.1 M sodium citrate buffer pH 2.5). The main protein peak in the elution is collected and its pH adjusted to neutrality with 1 M Tris buffer (pH 8.5). The protein pool is concentrated to 1-2 mg/ml using 10K Vivaspin membrane (Vivasciences) and sterile filtered (0.45 μm) before storage at 4° C.

For large preparations of a mAb of the invention, the cell free concentrate is purified over three sequential chromatography columns (Protein A, Anion Exchange, and Hydrophobic Interaction chromatography). The purity of the mAb after these chromatography steps is greater than 99% as assessed by analytical size exclusion chromatography. The mAb is exchanged into a buffer as listed below depending upon the concentration of the antibody. Chemical stability results indicate a preferred pH between 6.0 and 7.0 (inclusive); although for 20 mg/ml preparations, the pH may be between 5.5 and 7.0 (inclusive, e.g., 5.5, 5.6, 5.7, 5.8, 5.9, 6.0, 6.1, 6.2, 6.3, 6.4, 6.5, 6.6, 6.7, 6.8, 6, or 7.0). For lyophilized product, a sodium chloride level of 90-30 mM (90, 85, 80, 75, 70, 65, 60, 55, 50, 45, 40, 35 or 30 mM or any value between 30 and 90 mM) is preferred, while for a liquid formulation (e.g., to be administered subcutaneously) a sodium chloride level of 100-150 mM (100, 110, 120, 130, 140, or 150 mM or any value between 100 and 150 mM) is preferred. The product is then concentrated to a final concentration of about 10, 20 or 25 mg/ml (alternatively higher, 30, 40, 50, 60, 70, 80, 90, 100, 110, 120, 130, 140, 150 mg/ml or higher) and sterile filtered. The filtered product may be immediately frozen at −70° C. or may be lyophilized A minimal weight ratio of 1:2 for antibody to lyoprotectant, (e.g., sucrose or trehalose) is needed for stable lyophilized formulation but is not required for a liquid formulation. Additionally, 0.02% surfactant (w/v), i.e., polysorbate-80, is added for both solution formulations and solutions to be lyophilized. The lyophilized material is resuspended in sterile Water for Injection or sterile 0.9% sodium chloride prior to administration.

TABLE 34

| mAb conc. | Buffer | pH | NaCl (mM) |
|---|---|---|---|
| 10 mg/mL | 10 mM citrate (Na) | 6.0 | 30, 50-150 |
| 20 mg/mL | 10 mM citrate | 5.5 | 50-150 |
| 20 mg/mL | 10 mM citrate | 6.0 | 50-150 |
| 20 mg/mL | 10 mM citrate | 6.5 | 50-150 |
| 20 mg/mL | 10 mM citrate | 7.0 | 50-150 |
| 20 mg/mL | 10 mM histidine | 6.5 | 150 |
| >50 mg/mL | 10 mM citrate | 5.5 | 50-150 |
| >50 mg/mL | 10 mM citrate | 6.0 | 50-150 |
| >50 mg/mL | 10 mM citrate | 6.5 | 50-150 |
| >50 mg/mL | 10 mM histidine | 6.5 | 150 |

Antibody Half Life In Vivo

Serum pharmacokinetics of antibodies of the invention (e.g., mAb 126 and 121 [IgG4 Fc region with Fab 126 or 121 respectively]) are determined after intravenous or subcutaneous administration in male cynomolgus monkeys. Concentrations of the antibodies in the serum are determined using a standard antigen-capture ELISA assay in which plates are coated with human IL-17 and bound serum antibody is detected using an anti-IgG4 secondary antibody. Following intravenous administration of 1 mg/kg, mAb 126 is eliminated with a mean half-life of 6.5 days and mAb 121 is eliminated with a mean half-life of about 11 days. Following subcutaneous administration of 1 mg/kg, mAb 126 has a mean elimination half-life of 10.3 days and mAb 121 has a mean elimination half-life of 13 days.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient Example 17

Confirmation of Stability and Activity of TABALUMAB (LY2127399)

LY2127399 (TABALUMAB®) is a human monoclonal antibody that specifically binds to TNFSF13b polypeptides. TNFSF13b has high affinity for hTNFSF13b (e.g., $K_D=10^{-8}$ M or less), a slow off rate for TNFSF13b dissociation (e.g., $K_{off}=10^{-3}$ sec$^{-1}$ or less) and neutralizes TNFSF13b activity in vitro and in vivo. LY2127399 is useful in one embodiment for inhibiting TNFSF13b activity in a human subject suffering from a disorder in which hTNFSF13b activity is detrimental.

LY2127399 has a molecular weight of 146.25 kDa and a molecular formula of $C_{6518}H_{10008}N_{1724}O_{2032}S_{38}$. Examples of anti-hTNFSF13b human antibodies that meet the aforementioned kinetic and neutralization criteria include 4A5-3.1.1-B4 antibodies.

Pharmaceutical compositions may be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration. Therapeutic agents of the invention can all be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 6 and 8 is tolerated.

To determine the stability of IMCLY2127399 (TABALUMAB®), samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of LY2127399 (TABALUMAB®) is determined using methods and controls appropriate to the agent, for example, using methods provided in U.S. Pat. No. 7,317,089; U.S. Pat. No. 7,728,109; U.S. Pat. No. 8,173,124; and US Patent Publications US 2005/0070694; US 2008/0175841; US 2012/0195904; the entire contents of which are incorporated by reference herein, and from which the examples below are adapted.

Functional Activity of Anti-hTNFSF13b Human Antibodies

Neutralizing activity of the anti-hTNFSF13b human antibodies of the invention was measured using a murine Il-1 dependent B cell line, Ti 165.17. The cells were washed three times with assay media (RPMI1640 containing 10% FBS, 1 mM sodium pyruvate, $5\times10^{-5}$ M 2-mercaptoethanol and penicillin, streptomycin and fungizone) to remove IL-1. The cells were resuspended at 100,000 cells/ml in assay media containing 2.5 ng/ml soluble huTNFSF13b and plated at 5000 cells/well in a 96 well plate and incubated at 37° C. in 5% $CO_2$. Supernatants from ELISA positive hybridomas were included at a 1:4 dilution. Forty-eight hours later, 20 μl of Promega CellTiter 96 Aqueous One Solution (Madison, Wis.) was added and the plate incubated for 5 more hours at 37° C. in 5% $CO_2$. Absorbance was read at A490, to measure proliferation. As a control, the antibodies were added to IL-1 stimulated cells. There was no evidence of inhibition of IL-1 stimulated proliferation, only the hTNFSF13b stimulated proliferation.

The neutralizing antibodies were tested for the ability to inhibit TNFSF13b augmented primary human B cell proliferation in response to anti-IgM stimulation. Primary human B cells were isolated from human blood using CD19 positive selection using the MACS magnetic isolation system (Miltenyi Biotec, Auburn, Calif.). The B cells were added to wells of a 96-well plate at $2\times10^5$ cells per well in complete RPMI containing 10% FCS (complete RPMI is RPMI1640 containing 10 mM L-glutamine, 100 U/ml penicillin, 100 μg/ml streptomycin, 1 mM sodium puruvate, 0.1 mM nonessential amino acids, and $1\times10^5$ M P-mercaptoethanol). Some of the wells were coated with 10 μg/ml anti-human IgM in PBS (BD PharMingen, Clone G20-127), overnight at 4° C. and washed four times with PBS before use. Some of the cells were stimulated with soluble hTNFSF13b (25 ng/ml) in the presence or absence of neutralizing anti-hTNFSF13b antibody (2.5 μg/ml).

Characterization of Monoclonal Antibodies

All of the neutralizing anti-hTNFSF13b antibodies were either human IgG1 or human IgG4. They were also assayed for their ability to bind to hTNFSF13b in a denatured state, i.e., hTNFSF13b separated on SDS-PAGE and blotted onto nitrocellulose. All of the neutralizing antibodies failed to bind hTNFSF13b in a Western blot while several of the non-neutralizing antibodies were able to do so.

Experiments utilizing the BIACore system were performed to determine if non-neutralizing antibodies and neutralizing antibodies bound to the same site on hTNFSF13b. First, 4A5-3.1.1-B4 was coated onto a chip followed by injection of hTNFSF13b and then a saturating amount of non-neutralizing antibody. Once saturation was achieved, a high concentration of 4A5-3.1.1-B4 was run over the chip. Eleven of the non-neutralizing monoclonal antibodies were unable to compete for the same binding site as 4A5-3.1.1-B4. One non-neutralizing hybridoma was able to block the binding of 4A5-3.1.1-B4 by approximately 45%, indicating that it may have an epitope near the 4A5-3.1.1-B4 epitope.

Using the same experimental design, it was also determined that the neutralizing mAb, 4A5-3.1.1-B4, could compete for the same binding site as one of the receptors for hTNFSF13b, TACI. These experiments suggest that TACI-Fc and 4A5-3.1.1-B4 may have overlapping epitopes on hTNFSF13b.

4A5-3.1.1-B4 was immobilized on a solid phase by passing the antibody solution over an IMAC resin loaded with $Co^{+2}$. Following binding, the cobalt was oxidized to the +3 state by incubation of the resin with a dilute peroxide solution. After washing the resin, native hTNFSF13b and hTNFSF13b that was modified (by reduction/alkylation or by thermal denaturation) was passed over the column. After washing, the bound protein was eluted with an acidic solution and the eluted proteins were analyzed by MALDI MS. 4A5-3.1.1-B4 bound native recombinant hTNFSF13b, but did not bind either the chemically or thermally modified hTNFSF13b. Therefore, the 4A5-3.1.1-B4 appears to recognize a conformational epitope on soluble hTNFSF13b.

Recombinant soluble hTNFSF13b (RDI) was incubated with 4A5-3.1.1-B4 or anti-TNFSF13b rabbit polyclonal antibody (MoBiTec, Marco Island, Fla.; against amino acids 254 to 269 of hTNFSF13b) on ice for 2 hours and the protein mixture was applied to a size-exclusion HPLC (two, tandem TosoHaas TSK-GEL G3000PW columns) equilibrated in PBS at a flow rate of 0.25 ml/min. Proteins were eluted with PBS. As controls, antibody solutions and the solution of hTNFSF13b were analyzed separately. Human TNFSF13b eluted from the size exclusion column in a position consistent with a trimer of TNFSF13b molecules. The elution of trimeric hTNFSF13b shifted to an earlier timepoint in the presence of 4A5-3.1.1-B4 but not in the presence of anti-TNFSF13b polyclonal antibodies indicating the binding of trimeric hTNFSF13b to the 4A5-3.1.1-B4 antibody. This data suggests that the neutralizing mAb 4A5-3.1.1-B4 binds to a conformational epitope on hTNFSF13b.

Affinity Measurement of Monoclonal Antibodies by BIAcore

The affinity of various anti-hTNFSF13b human antibodies for hTNFSF13b was measured using a BIAcore 2000 instrument system. The system utilizes the optical properties of Surface Plasmon Resonance to detect alteration in protein concentration of interacting molecules within a dextran biosensor matrix. Except where noted, all reagents and materials were purchased from BIAcore AB (Uppsala, Sweden). All measurements were performed at 25° C. Samples were dissolved in HBS-EP buffer (150 mM NaCl, 3 mM EDTA, 0.005% (w/v) surfactant P-20, and 10 mM HEPES, pH 7.4). Goat anti-mouse IgG (Fc specific; Jackson Immunoresearch, West Grove, Pa.) was immobilized on flow cell 1 on a CM5 sensor chip using the amine coupling kit. Goat anti-human IgG (Fc specific; Jackson Immunoresearch) was immobilized on flow cell 2 also by amine coupling. Both antibodies were immobilized to reach 700 response units each.

Binding of recombinant hTNFSF13b (Research Diagnostics, Inc., Flanders, N.J.) was evaluated using multiple analytical cycles. Each cycle was performed at a flow rate of 30 μl/min. and consisted of the following steps: injection of 150 μl of 4A5-3.1.1-B4 at 20 μg/ml, injection of 250 μl of hTNFSF13b (starting at 50 nM and using 2 fold serial dilutions for each cycle) followed by 15 minutes for dissociation, and regeneration using 90 μl of 10 mM glycine HCl, pH 1.5.

Association and dissociation rates for each cycle were evaluated using a Langmuir 1:1 binding model in the BIAevaluation software. The $K_D$ of 4A5-3.1.1-B4 for hTNFSF13b was determined to be 38 μM.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient Example 18

Confirmation of Stability and Activity of NECITUMUMAB

IMC-11F8 (NECITUMUMAB®) is a fully human monoclonal antibody (IgG1) that binds to human EGFR with high affinity and that neutralizes activation of EGFR. IMC-11F8 may potentially induce cell-mediated cytotoxicity in cancer cells due to the fact that it contains an IgG1 moiety, and can therefore be useful in treating mammals with neoplastic growth and non-cancerous hyperproliferative disease.

IMC-11F8 has human $V_H$ and $V_L$ framework regions (FWs) as well as CDRs. The $V_H$ variable domain of IMC-11F8 has three CDRs and four FWs and the $V_L$ domain has three CDRs and four FWs.

To determine the stability of IMC-11F8 (NECITIMUMAB®), samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of IMC-11F8 (NECITIMUMAB®) is determined using methods and controls appropriate to the agent, for example, using methods provided in U.S. Pat. No. 7,598,350 and US Patent publication US 2007/0264253, the entire contents of which are incorporated by reference herein, and from which the below examples are adapted.

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et al., *Molecular Cloning: A Laboratory Manual*, 2nd ed., Cold Spring Harbor Laboratory Press (1989).

In Vitro Binding of Antibodies to EGFR (Adapted from U.S. Pat. No. 7,598,350)

Antibodies were screened in a solid state ELISA comparing the binding characteristics of IMC-11F8 and IMC-C225. Ninety six-well microtiter plate was coated overnight with 1 µg/mL in carbonate buffer at 4° C. Plates were blocked with phosphate buffered saline (PBS) supplemented with 10% new born calf serum for one hour at 37° C. Various amounts of IMC-11F8 or IMC-C225 were added to the plates and incubated at room temperature for a further 60 minutes, followed by washing with PBS. Mouse anti-human Fc antibody-horse radish peroxidase (HRP) conjugate were added and incubated for an additional 60 minutes at room temperature, followed by extensive washing with PBS. The plate was then incubated with HRP substrate for 30 sec.-2 min and the reaction stopped with 0.1 M $H_2SO_4$. The plates were read using an ELISA reader at $OD_{450nm}$.

Both IMC-11F8 and IMC-C225 exhibit comparable binding to EGFR.

Binding Kinetics of Anti-EGFR Antibodies

The binding kinetics of IMC-11F8 and IMC-C225 IgG antibodies and their respective Fab fragments were measured using a BIAcore sensor (Pharmacia Biosensor,) EGFR-AP fusion protein was immobilized onto a sensor chip and soluble IMC-11F8 and IMC-C225 antibodies were injected at concentrations ranging from 1.5 nM to 100 nM. Sensorgrams were obtained at each concentration and were analyzed with BIA Evaluation 2.0, a program to determine the rate constants, $k_{on}$ and $k_{off}$. The affinity constant, $K_d$, was calculated from the ratio of rate constants, $k_{off}/k_{on}$.

The binding kinetics of the anti-EGFR antibodies of the present invention are illustrated in Table 35. These show that both IgG antibodies have comparable binding kinetics to EGFR.

TABLE 35

| Antibody | Format | $K_{on}$ ($10^5$ $M^{-1}s^{-1}$) | $K_{off}$ ($10^{-4}s^{-1}$) | $K_d$ (nM) |
| --- | --- | --- | --- | --- |
| IMC-11F8 | Fab | 22.9 ± 9.9 | 36.7 ± 8.5 | 1.78 ± 0.5 |
| IMC-11F8 | IgG | 18.6 ± 7.7 | 5.8 ± 2.2 | 0.32 ± 0.06 |
| IMC-C225 | Fab | 23.1 ± 4.8 | 11.7 ± 3.4 | 0.53 ± 0.17 |
| IMC-C225 | IgG | 21.3 ± 7.3 | 5.4 ± 1.0 | 0.3 ± 0.2 |

Specificity of the Antibodies for EGFR

Antibody binding to EGFR was evaluated by a $^{125}$I-EGF competition assay. HT29 cells were seeded at $2 \times 10^4$ cells per well in 24-well COSTAR™ plates (Fisher Scientific, U.S.A.) in McCoy's 5a medium supplemented with 1.5 mM L-glutamine, 10% CS and antibiotics at 37° C. The cell monolayer was then incubated at room temperature for 1 hour with various concentrations of unlabeled EGF, 11F8 or IMC-C225 that were mixed with various amounts of $^{125}$I-labeled EGF. Cells were washed with cold PBS and cell-associated radioactivity was measured in a gamma counter.

At concentrations of between 10 to 100 nM, IMC-11F8 is as efficient as IMC-C225 in inhibiting $^{125}$I-EGF binding to EGFR on HT29 cells. Both antibodies are better at competing for binding than EGF, the natural ligand of EGFR. Similar results were observed for inhibition of $^{125}$I-EGF binding to EGFR on A431 cells.

EGFR Activation

Briefly, a kinase receptor activation assay (KIRA assay), or phosphorylation assay, was carried out using BxPC3 or A431 cells. Cells were first grown to 90% confluency in DME supplemented with 4 mM L-glutamine adjusted to contain 1.5 g/L sodium bicarbonate and 4.5 g/L glucose, 10% CS, at 37° C. Prior to experimentation, the cells were starved for 24 h in DME supplemented with 0.5% CS. To evaluate the effects of antibodies, IMC-11F8, IMC-C225 and IMC-1C11 on EGF-induced activation of EGFR, various concentrations of antibodies were prebound at room temperature for 30 minutes, followed by stimulation with EGF at 8 ng/mL for another 15 minutes. Following stimulation, cell monolayers were washed with ice cold PBS containing 1 mM sodium orthovanadate. Cells were lysed in lysis buffer [20 mM Tric-HCl, pH. 7.4, 1% Triton X-100, 137 mM NaCl, 10% glycerol, 10 mM EDTA, 2 mM sodium orthovanadate, 100 mM NaF, 100 mM sodium pyrophosphate, 5 mM PEFABLOC® SC (Boehringer Mannheim Biochemicals, Indianapolis, Ind.), 100 µg aprotinin and 100 µg/mL leupeptin] and centrifuged at 14,000×g for 10 minutes. Cleared cell lysates were added to wells of 96-well plates coated with polyclonal anti-EGFR antibody. The plates were washed to remove non-specifically bound proteins and the level of EGFR phosphorylation was assessed by the addition of anti-phosphotyrosine antibody. Upon extensive washing, the amount of bound anti-phoshotyrosine antibody was measure using an ELISA reader at $OD_{450}$ nm.

The results show a marked decrease in phosphorylation of EGFR by IMC-11F8 antibody in both BxPC3 and A431 cells tested as compared to control antibody, IMC-1C1.

Inhibition of EGF-stimulated EGFR phosphorylation was further evaluated by Western blot analysis of the immunoprecipitated EGFR. A431 cells were prebound with antibodies followed by stimulation with EGF as described above. A control antibody that binds to EGFR but does not inhibit EGFR phosphorylation was used. Protein (EGFR) was immunoprecipitated from the cleared lysates using polyclonal anti-EGFR antibody followed by Protein A Sepharose beads. The bound-beads were then washed once with 0.2% Triton X-100, 10 mM Tris-HCl, pH 8.0, 150 mM NaCl, 2 mM EDTA (Buffer A), twice with Buffer A containing 500 mM NaCl and twice with Tris-HCl, pH 8.0. Drained beads were mixed with 30 µL 2×SDS loading buffer, boiled and the supernatant was subjected to SDS-PAGE. After separation of proteins by electrophoresis, the protein bands were transferred onto nitrocellulose filters for Western Blot analysis. Filters were blocked overnight in blocking buffer, 50 mM Tris-HCl, pH7.4, 150 mM NaCl (TBS) containing 5% bovine serum albumin and 10% nonfat dried milk. To detect phosphorylated receptor, blots were probed with an anti-phosphotyrosine antibody in blocking buffer for 1 hour at room temperature. Blots were then washed extensively with 0.5×TBS containing 0.1% Tween-20 (TBS-T) and incubated with goat anti-mouse Ig conjugated to HRP (Ainersham, Little Chalfont, U.K.). Blots were washed with TBS and incubated for 1 minute with a chemiluminescence reagent (ECL, Amersham, Little Chalfont, U.K.). Anti-phosphotyrosine reacting with phosphorylated proteins was detected by exposure to a high performance luminescence detection film (Hyperfilm-ECL, Arnersham, Little Chalfont, U.K.) for 0.5 to 10 minutes.

Western blot analysis showed that IMC-11F8, like IMC-C225, inhibits EGFR phosphorylation. Neither EGF-antibody nor the control antibody-treated cells completely inhibits EGFR phosphorylation. Synthesis of EGFR is not inhibited with the addition of antibodies to the cells. Phosphorylation of EGFR is inhibited by IMC-11F8. Greater than 70% inhibition was observed for three tumor cell lines of different origin (A431, BxPC3, HT-29) at the lowest antibody concentration tested (0.8 mM).

The effect of IMC-11F8 on one of the major downstream signaling molecules of EGFR, MAP kinases p44/p42, was also examined. IMC-11F8 blocked p44/42 MAP kinases phosphorylation following EGF stimulation in A431, BxPC3 and HT-29 cells in a dose-dependent manner.

Inhibition of Cell Proliferation

The MTT Cell Proliferation Assay is measured colormetrically as a result of reduction of the yellow tetrazolium, MTT (3-(4,5-dimethylthiazolyl-2)-2,5-phenyltetrazolium bromide) by metabolically active cell to an intracellular purple formazan product, which can be solubilized and quantified by spectrophotometric means. Briefly, DiFi cells were cultured overnight in DMEM-10% CS. Antibodies, IMC-11F8, IMC-C225 or IMC-1C11 were added to triplicate wells and incubated for an additional 72 hours at 37° C., 5% $CO_2$. To measure cell growth, a 20 µL aliquot of tetrazolium dye was added to each well and the cells were incubated for 3 hours at 37° C. When the purple precipitate was clearly visible under a microscope, the cells were lysed by addition of 100 µl detergent reagent. Absorbance of the formazan product was measured at $OD_{570}$ nm as a quantitation of proliferation.

Unlike control antibody IMC-1C11, IMC-11F8 is as potent an inhibitor of cell proliferation as IMC-C225.

Antibody-Dependent Cellular Cytotoxicity (ADCC) Activity

One method of assessing cell death is via an antibody dependent cell-mediated cytotoxicity assay or ADCC, which generally use the radioisotope $^{51}Cr$. Target cells labeled with $^{51}Cr$ were mixed with antibody and the degree of killing was assessed by release of $^{51}Cr$. Briefly, approximately $3 \times 10^6$ DiFi cells were suspended in 0.5 µl culture medium and 0.5 mCi of $Na^{51}CrO_4$ was added. The mixture was incubated for 1 h at 37° C. with occasional shaking. The cells were then washed three times with cold culture medium. The labeled cells were then suspended in 100 µl culture medium containing varying concentrations of anti-EGFR antibodies (IMC-11F8 or IMC-C225) and incubated for 30 minutes at 4° C. The cells were then washed three times with culture medium by centrifugation. Rabbit complement was added and the treated cells were further incubated at 37° C. for 1 h. 50 µl of cold medium were then added and centrifuged. The supernatants were then removed and the radioactivity released by the cells into the supernatant was measured in a gamma counter. The maximum release of the radioactivity was obtained by adding 1% Triton X to the target cells. The percent cytotoxicity was calculated as cpm experimental release minus cpm background times 100%, which is then divided by the cpm maximum release minus cpm background.

IMC-11F8 and WC-C225 (or ERBITUX™) mediate cell death via activation of the Antibody Dependent Cellular Cytotoxicity or ADCC activity).

In Vivo Inhibition of Tumor Cell Growth in Mice

In vivo anti-tumor studies were designed to determine if IMC-11F8 would block the growth of tumor cells in a xenograft model. Athymic mice (nu/nu; Charles River Lab, Wilmington, Mass.) were injected subcutaneously with 1-2 million A431 or BxPC-3 cells in the flank. Anti-EGFR antibodies (IMC-11F8 and IMC-C225) or control antibody was administered intraperitoneally at either 1 mg/dose or 0.3 mg/dose, three times per week. Tumor size was measured at least three times per week with a caliper and tumor volume calculated (See, e.g. Baselga et al., J Natl. Cancer Inst. (1993) 85:1327-1333)

At 1 mg dose, IMC-11F8 is as effective as IMC-C225 (CETUXIMAB) in suppressing or inhibiting tumor growth as compared to control animals. At a lower dose of 0.3 mg, progression of tumor growth is retarded. A similar effect of IMC-11F8 and 1MC-C225 in a second tumor model (BxPC-3 xenograft) is observed. The kinetics of BxPC3 tumor growth is similar to that observed in the A431 tumor model. At the 1.0 mg/mouse/injection dose level IMC-11F8 led to 6 tumor regressions out of 8 A413-bearing animals, and 5 tumor regression out of 8 BxPC3-bearing mice.

Immunohistochemistry staining of both A431 and BxPC3 xenograft sections revealed that IMC-11F8 treatment markedly reduced the tumor cell density and increased the area of necrotic acellular debris within the tumors. Further, IMC-11F8 reduced the percentage of Ki-67 positive cells across the entire tumor section, indicating a reduction in cell proliferation within the tumors.

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient.

Example 19

Confirmation of Stability and Activity of IMC-A12

IMC-A12 (Cixutumumab) is a fully human IgG1/λ, monoclonal antibody. IMC-A12 binds to the insulin-like growth factor-I receptor (IGF-IR) with high affinity, thereby inhibiting binding between IGF-IR and its ligands and subsequent downstream signaling.

To determine the stability of IMC-A12 (Cixutumumab), samples are incubated in containers as described in the stability testing and/or stress testing methods provided in Example 6. Preferably, the samples are incubated both in standard glass vials with appropriate closures and glass vials such as those provided herein. At the desired intervals, samples are removed and assayed to determine the stability and/or activity of the agent. The stability and/or activity of IMC-A12 (Cixutumumab) is determined using methods and controls appropriate to the agent, for example, using methods provided in US Patent publication US 2010/0260766 and European Patent publication EP2136839A4, the entire contents of which are incorporated by reference herein, and from which the below examples are adapted.

The following examples further illustrate the invention, but should not be construed to limit the scope of the invention in any way. Detailed descriptions of conventional methods, such as those employed in the analysis of proteins can be obtained from numerous publications such as *Current Protocols in Immunology* (published by published by John Wiley & Sons), hereby incorporated by reference in its entirety.

For all liquid formulation screening studies, the protein concentration was fixed at 5 mg/mL. A multi-component buffer consisting of 10 mM Sodium Phosphate, 10 mM Sodium Citrate, 10 mM Sodium Acetate, 10 mM L-Histidine and 125 mM Sodium Chloride was used to screen for the optimal pH. Buffer type, requirement for TWEEN 80, glycine concentration, and NaCl concentration were examined using a design of experiment approach (DOE, IMP software). Linear regression analysis was performed to determine the significance of tested variables. The predicted formulation was confirmed using a traditional one-factor-at-a-time methodology. The effect of the tested variables on thermal stability was examined using differential scanning calorimetry (DSC) and real-time isothermal studies. Controlled agitation at 300 rpm at room temperature was used as a test for mechanical stability. Photo stability of the liquid formulations was examined per ICH guidelines. Freeze-thaw stability was determined by freezing test samples to −20° C. and −70° C. and thawing at 4° C.

For lyophilized IMC-A12 formulations, buffer type, stabilizers, and bulking agents were examined, using design of experiments fractional factorial model at IMC-A12 concentration of 20 mg/mL. The concentration of IMC-A12, ratio of trehalose concentration to IMC-A12 concentration, and the concentration of TWEEN 80 was optimized using mixture design model. The predicted optimal freeze-dried formulation was compared with PBS and Citrate solution formulations using one-factor-at-a-time methodology. The effect of variables on thermal stability was examined by real-time isothermal studies. Photo stability of the lyophilized formulation was examined per ICH guidelines.

TABLE 36

Materials, Grade and Vendors

| Materials | Grade | Vendor |
| --- | --- | --- |
| IMC-A12 | 1278-116, 1278-151 | N/A |
| Sodium Citrate Dihydrate | USP | J. T. Baker |
| Citric Acid Anhydrous | USP | J. T. Baker |
| Sodium Acetate | USP | J. T. Baker |
| L-Histidine | USP | J. T. Baker |
| Sodium dibasic phosphate | USP | J. T. Baker |
| Sodium monobasic phosphate | USP | J. T. Baker |
| NaCl | USP | J. T. Baker |
| Tween 80 | Multi Compendia | J. T. Baker |
| Glycine | USP | J. T. Baker |
| Sucrose | Multi Compendia | Ferro Pfanstiehl |
| Trehalose | Multi Compendia | Ferro Pfanstiehl |
| Manitol | Multi Compendia | J. T. Baker |

IMC-A12 for use in screening studies was prepared by buffer exchange into experimental buffers using 50K cut-off (YM 50) centriprep centrifugal filtration devices and an Allegra X-12R centrifuge (Beckman). The protein concentration was determined by absorbance at 280 nm using an extinction coefficient of 1.50 and the concentration adjusted to 0.5 mg/mL with the appropriate buffer. TWEEN 80 was added from a 10% (w/v) stock solution following protein concentration adjustments. IMC-A12 at 5 mg/mL in PBS formulation was used as a control. All samples were 0.22 μm filtered through a syringe filter (Durapore PVDF membrane).

The freeze-drying process was performed using Lyostar II-freeze-dryer. The product was loaded in to lyophilizer at room temperature. The shelf temperature was cooled to −50° C. with a cooling rate of 0.5° C./min Soaking time at −50° C. was 2 hours. Primary drying and secondary drying was performed at −30° C. and 20° C. for 12 hours each. The temperature was ramped at 0.5° C./min Chamber pressure during primary and secondary was 50 mT. After lyophilization was completed, lyophilizer chamber was backfilled to a half-atmospheric pressure with $N_2$ and capped.

pH Optimization Study

A multi-component buffer (MCB) consisting of 10 mM Sodium Phosphate, 10 mM Sodium Citrate, 10 mM Sodium Acetate, 10 mM L-Histidine and 125 mM Sodium Chloride was used to determine the optimal pH. This buffer system was intended to minimize counter ion (salt effects) that may have other wise had a greater effect than pH alone. The pH screening design matrix is shown in Table 37. IMC-A12 concentration was kept at 5 mg/mL. The pH range examined was 5.0-8.0, at 0.5 pH unit intervals. The effect of pH on thermal and mechanical stability was studied and the results presented below.

TABLE 37

Design matrix for pH Screening

| Buffer | [A12], (mg/mL) | pH |
| --- | --- | --- |
| MCB-1 | 5.0 | 5.0 |
| MCB-2 | 5.0 | 5.5 |
| MCB-3 | 5.0 | 6.0 |
| MCB-4 | 5.0 | 6.5 |

TABLE 37-continued

| Design matrix for pH Screening | | |
|---|---|---|
| Buffer | [A12], (mg/mL) | pH |
| MCB-4 | 5.0 | 7.0 |
| MCB-5 | 5.0 | 7.5 |
| MCB-6 | 5.0 | 8.0 |

Differential Scanning Calorimetry (DSC) Study

Thermal melting curves for IMC-A12 in experimental formulations (shown in Table 37) were assayed by Differential Scanning calorimetry (DSC) in order to assess the transition temperature (Tm) for IMC-A12 in the test conditions. The protein concentration was 5 mg/mL and temperature ramping was from 5° C. to 95° C. at a scan rate of 1.5° C./min. The melting curves were fitted to a sum of three Tm. The melting temperature; Tm1, corresponding to first transition peak as a function of pH was observed. Tm1 was comparable between pH 6.5-8.0.

Agitation Study

Samples were stressed by agitation on a platform shaker. Samples as described in Table 36 including 5 mL of IMC-A12 at 5 mg/mL in 27.5 mL glass vials were agitated at 300 RPM with Headspace set to be 81.8%. The study was performed at room temperature for 72 hours. Percent loss was least and percent monomer was highest between pH 6.0-7.0.

Real-Time Accelerated Temperature Stability at 40° C. and 50° C.

IMC-A12 at 5 mg/mL in various pH buffers (Table 37) was incubated at 40° C. for 3 weeks and at 50° C. for 1 week. The effect of pH on percent monomer was analyzed by SEC-HPLC. The variation of percent monomer remained as a function of pH after 3 week of incubation at 40° C. and 1 week of incubation at 50° C. are observed. The percent monomer remaining was largest between pH 6.0-6.5

Real-Time Freezing Temperature Stability at −20° C. and −70° C.

IMC-A12 at 5 mg/mL in various pH buffers (listed in Table 37) were incubated at −20° C. and −70° C. for three weeks. The effect of pH on percent monomer was analyzed by SEC-HPLC. The pH did not have significant effect on percent monomer either at −20° C. or at −70° C.

Summary of pH Optimization

The optimal pH for IMC-A12 at 5 mg/mL was found to be between 6.0 and 6.5.

Excipient Screening Study for Solution Formulations

The pH optimization studies above demonstrate that IMC-A12 has greatest stability between pH 6.0 and 6.5. In this Example, we study the effect of buffer type, citrate and histidine, on the stability of IMC-A12 at pH 6.0 and 6.5. Requirement for TWEEN 80 and NaCl and glycine concentration are also examined. Protein concentration are kept fixed at 5 mg/mL. The design matrix for excipient screening is shown in Table 38.

TABLE 38

| Design matrix for excipient optimization | | | | | | |
|---|---|---|---|---|---|---|
| Formulations | [A12], mg/mL | Buffer type (10 mM) | pH | Tween 80% | [NaCl] (mM) | [Glycine] (mM) |
| Formulation-1 | 5.0 | Histidine | 6.0 | 0 | 80 | 140 |
| Formulation-2 | 5.0 | Histidine | 6.0 | 0.01 | 100 | 75 |
| Formulation-3 | 5.0 | Histidine | 6.5 | 0.01 | 75 | 150 |
| Formulation-4 | 5.0 | Histidine | 6.5 | 0 | 150 | 0 |
| Formulation-5 | 5.0 | Histidine | 6.5 | 0.01 | 100 | 100 |
| Formulation-6 | 5.0 | Citrate | 6.5 | 0 | 150 | 0 |
| Formulation-7 | 5.0 | Citrate | 6.0 | 0.01 | 150 | 0 |
| Formulation-8 | 5.0 | Citrate | 6.0 | 0 | 50 | 150 |
| Formulation-9 | 5.0 | Citrate | 6.5 | 0.01 | 50 | 150 |
| Formulation-10 | 5.0 | Citrate | 6.5 | 0.01 | 100 | 100 |
| PBS | 5.0 | Phosphate | 7.2 | 0 | 145 | 0 |

Osmolality Measurement

The osmolality of the Table 38 formulations were measured using Wescor Vapor Pressure Osmometer. Results are shown in Table 39. Osmolality of tested formulations were within the desired range of 260-320 mOsmole/Kg.

TABLE 39

| Osmolality of the formulations in Table 38 | | | | | | | |
|---|---|---|---|---|---|---|---|
| Formulations | [A12], mg/mL | Buffer type (10 mM) | pH | Tween 80% | [NaCl] (mM) | [Glycine] (mM) | Osmolality (mOsmole/Kg) |
| Formulation-1 | 5.0 | Histidine | 6.0 | 0 | 80 | 140 | 302 |
| Formulation-2 | 5.0 | Histidine | 6.0 | 0.01 | 100 | 75 | 283 |
| Formulation-3 | 5.0 | Histidine | 6.5 | 0.01 | 75 | 150 | 304 |
| Formulation-4 | 5.0 | Histidine | 6.5 | 0 | 150 | 0 | 304 |
| Formulation-5 | 5.0 | Histidine | 6.5 | 0.01 | 100 | 100 | 296 |
| Formulation-6 | 5.0 | Citrate | 6.5 | 0 | 150 | 0 | 318 |
| Formulation-7 | 5.0 | Citrate | 6.0 | 0.01 | 150 | 0 | 318 |
| Formulation-8 | 5.0 | Citrate | 6.0 | 0 | 50 | 150 | 275 |
| Formulation-9 | 5.0 | Citrate | 6.5 | 0.01 | 50 | 150 | 276 |
| Formulation-10 | 5.0 | Citrate | 6.5 | 0.01 | 100 | 100 | 316 |
| PBS | 5.0 | Phosphate | 7.2 | 0 | 145 | 0 | 294 |

Differential Scanning calorimetry Study

Thermal melting curves for IMC-A12 in experimental formulations (listed in Table 38) were assayed using DSC to assess the transition temperature (Tm) for IMC-A12 in the test conditions. The protein concentration was 5 mg/mL and temperature ramping was from 5° C. to 95.° C. at a scan rate of 1.5° C./min. The melting temperature corresponding to the main transition peak was fitted to a linear regression model to estimate the effect of tested variables. The p and $R_{sq}$ for the fit was 0.003 and 0.99, respectively. The optimal buffer was determined to be citrate buffer at pH 6.5. Glycine increased the melting temperature, and TWEEN 80 slightly lowered the melting temperature. NaCl does not have significant effect on the melting temperature.

Agitation Study

Samples were stressed by agitation on a platform shaker. The samples described in Table 38 with 5 mL of IMC-A12 at 5 mg/mL in 27.5 mL glass vial were agitated at 300 RPM. The study was performed at room temperature for up to 72 hours. Solution turbidity and percent monomer were determined as a function of agitation time. The effects of tested variables on turbidity and percent monomer were estimated by fitting the response to a linear regression model using JMP software. The p value for the Actual vs. Predicted plot for both turbidity and percent monomer were <0.001. The statistically significant variables were buffer, TWEEN and time. Citrate buffer with 0.01% TWEEN had the least turbidity and highest monomer content.

Real-Time Accelerated Temperature Stability at 40° C. and 50° C.

IMC-A12 at 5 mg/mL in the Table 38 formulations was incubated at 40° C. for 4 weeks and 50° C. for 2 weeks. Percent monomer for starting material and tested formulations after 4 weeks of incubation at 40° C., and 2 weeks of incubation at 50° C. was observed. DOE analyses of temperature stressed samples were observed. At 40° C., percent monomer for most of the tested formulations was comparable but better than PBS. At 50° C., formulations in citrate buffer (formulation 6-10) were superior to histidine buffers (formulation 1-5). DOE analysis shows that IMC-A12 has comparable stability between pH 6.0-6.5, and that NaCl has a destabilizing effect, while glycine has relatively less effect. Formulations 9 and 10 were found to be comparable. However, formulation 10 was preferred since it has less glycine concentration (closer to physiological condition).

Summary of Excipient Screening Study

DSC studies showed that Citrate buffer, glycine and pH 6.5 have increased IMC-A12 thermal stability. TWEEN-80 has slightly lowered the stability while NaCl did not have much effect. IMC-A12 is sensitive to mechanical stress. Thus, TWEEN 80 is required to stabilize against mechanical stress. IMC-A12 has better stability in citrate formulation than in Histidine at accelerated temperatures. Both, histidine and citrate buffers are superior than PBS formulation. Formulation 10, which contains 5 mg/mL, IMC-A12, 10 mM Citrate, 100 mM Glycine, 100 mM NaCl, 0.01% TWEEN 80, pH 6.5 (Citrate) was selected as an optimal formulation.

Comparison Between PBS and Citrate Solution Formulations

As discussed above, we developed a new solution formulation for IMC-A12 that contains 5 mg/mL IMC-A12, 10 mM Sodium citrate, 100 mM Glycine, 100 mM NaCl, 0.01% TWEEN 80, at pH 6.5 (Citrate). In this Example, we compared the stability of IMC-A12 in Citrate formulation with a PBS formulation.

Agitation Study

Samples were stressed by agitation on a platform shaker. The samples containing IMC-A12 at 5 mg/mL, in 27.5 mL glass vials were agitated at 300 RPM. The study was performed at room temperature for up to 72 hours. Concentration and turbidity measurements were performed using a Shimatzu 1601 biospec spectrophotometer. The concentration of IMC-A12 solutions was calculated from the absorbance at 280 nm, using an extinction coefficient of 1.5. Solution turbidity was measured by absorbance at 350 nm. The solution turbidity, percent material loss (due to the formation of insoluble aggregate), and percent monomer remaining as a function of agitation time were observed. For PBS formulations of IMC-A12, solution turbidity and percent loss increased with agitation time, while percent monomer decreased. Turbidity, percent loss and percent monomer all remained unchanged for Citrate formulation.

Real-Time Accelerated Temperature Stability at 40° C.

IMC-A12 at 5 mg/mL in PBS or Citrate formulations were incubated at 40° C. for up to 3 months. Following incubation, samples were analyzed by SEC-HPLC, SDS-PAGE and IEF. Results are shown below.

SEC-HPLC Analysis: Size exclusion chromatography was performed using an Agilent 1100 Series LC chromatograph and a Tosoh Biosep G3000SWXL column. The mobile phase was 10 mM Sodium phosphate, 0.5M CsCl pH 7.0. Fifty µg of sample was injected in a volume of 10 µl. The variation of percent monomer, aggregate, and degradant as a function of incubation time were observed. Percent monomer decreased and percent aggregate and degradant increased for both the formulations, but the rate was slower for Citrate formulation compared to PBS formulation.

SDS-PAGE Analysis:

IMC-A12 in PBS and Citrate formulations following 3 months of incubation at 40° C. was analyzed by reduced and non-reduced SDS-PAGE on 4-20% tris-glycine gradient gel. Ten µg of sample was loaded in a volume of 10 µl. Gel was stained with Coomassie blue. In comparison, more intense impurity bands were detected in the PBS formulation than in Citrate formulation.

IEF Analysis:

Isoelectric, focusing (IEF) was performed using IsoGel® Agarose IEF plates with a pH range from 6.0 to 10.5. Test samples were buffer exchanged into miliQ water containing 0.5% TWEEN 80. The 10 µg sample was loaded in a volume of 10 µl. Gel was stained with Coomassie blue. IMC-A12 in PBS and Citrate formulations following 3 months of incubation at 40° C. was analyzed by IEF. In comparison, more diffused and less defined bands were detected for PBS formulation than in Citrate formulation.

Freezing Temperature Stability of IMC-A12 at −20° C. and −70° C.

IMC-A12 at 5 mg/mL in PBS and Citrate formulations was incubated at −20° C. and −70° C. for up to 3 months. Percent monomer, following incubation was analyzed by SEC-HPLC. The variation of percent monomer as a function of time at −20° C. and at −70° C. was observed. The percent monomer did not change with time in either formulation.

Freeze-Thaw Stability of IMC-A12 at −20° C. and −70° C.

Freeze-thaw stability of IMC-A12 was evaluated by freezing the test sample to either −20° C. or −70° C. in a freeze-dryer (Lyo-star II, manufactured by FTS) with a ramp rate of 1° C./min. The sample was allowed to incubate for 1 hour and thawed at 4° C. with a ramp rate of 1° C./min. The freeze-thaw process was repeated up to 15 times. The variation of percent monomer as a function of number of freeze-thaw cycle at −20° C. and −70° C. was observed. As shown, IMC-A12 in Citrate formulation has better freeze-thaw stability than in PBS formulation. The decrease in percent monomer for PBS formulation was mainly due to increase in percent aggregates.

Photo-Stability of IMC-A12 Solution Formulations

Photo stability study for IMC-A12 was performed per ICH guideline. IMC-A12 at 5 mg/mL in PBS and Citrate formulations was exposed to light at room temperature. The total light exposure was 200 Watt hours/m2 near UV+1.2 million lux hours fluorescent. Control samples were wrapped with black paper to block light. Control and test samples were placed inside the photo stability chamber (Caron 6500 series, Caron, Marietta, Ohio). Following light exposure, both controls and test samples were analyzed by SEC-HPLC. Percent monomer, aggregate, and degradant for controls and light exposed samples are given in Table 40. IMC-A12 was found to be light sensitive in both formulations. However, the photo stability was significantly improved in the Citrate formulation than the PBS formulation.

TABLE 40

Photo-stability for IMC-A12 in PBS and Citrate Formulations

| Formulations | Product Lot | Monomer (%) | Aggregates (%) | Degredents (%) |
|---|---|---|---|---|
| PBS-Control | 1278-116 | 96.6 | 1.5 | 2.0 |
| PBS-Sample | 1278-116 | 73.5 | 22.8 | 3.7 |
| Citrate-Control | 1278-151 | 95.7 | 1.4 | 2.9 |
| Citrate-Sample | 1278-151 | 81.9 | 14.2 | 3.9 |

Summary of Comparison Between PBS and Citrate Formulations

IMC-A12 demonstrates significantly better stability in 10 mM Sodium citrate, 100 mM Glycine, 100 mM NaCl, 0.01% TWEEN 80, pH 6.5 (Citrate) formulation than in PBS formulation. Citrate is an isotonic formulation that is particulate free, stable against mechanical induced aggregation or precipitation, has minimized temperature-induced aggregation and degradation, is stabilized against freeze-thaw instability, and has enhanced photo stability.

Screening of Buffers, Cryo- and -Lyo Protectents and Bulking Agents for Lyophilized Formulations The buffer type, stabilizers and bulking agents for freeze-dried formulation was examined at IMC-A12 concentration of 20 mg/mL. The design matrix is shown in Table 41, fractional factorial design model was used. The design matrix for concentration optimization for IMC-A12, ratio of trehalose concentration to IMC-A12 concentration, and TWEEN 80 concentration is shown in Table 42. A mixture design model was used.

TABLE 41

Design Matrix for Stabiliziers and bulking agents screening

| # | Buffer (10 mM) | [A12] (mg/mL) | Trehalose (%) | Sucrose (%) | Mannitol (%) | Glycine | pH |
|---|---|---|---|---|---|---|---|
| 1 | histidine | 20 | 4 | 0 | 2 | 0 | 6.5 |
| 2 | histidine | 20 | 0 | 2 | 3 | 0 | 6.5 |
| 3 | histidine | 20 | 1 | 1 | 0 | 0 | 6.5 |
| 4 | histidine | 20 | 0.5 | 3.5 | 0 | 2 | 6.5 |
| 5 | histidine | 20 | 4 | 0 | 0 | 0 | 6.5 |
| 6 | histidine | 20 | 0 | 4 | 0 | 0 | 6.5 |
| 7 | citrate | 20 | 1.5 | 0.5 | 0 | 4 | 6.5 |
| 8 | citrate | 20 | 0.5 | 1.5 | 4 | 0 | 6.5 |
| 9 | citrate | 20 | 0 | 0 | 0 | 0 | 6.5 |
| 10 | citrate | 20 | 4 | 4 | 0 | 0 | 6.5 |

TABLE 42

Design Matrix for optimization of A12 concentration, Trehalose to A12 molar ratio and Tween 80 concentration

| # | Buffer (mM) | pH | [A12] (mg/mL) | Trehalose to A12 molar ratio | Tween 80% |
|---|---|---|---|---|---|
| 1 | Histidine | 6.5 | 50.0 | 200 | 0.000 |
| 2 | Histidine | 6.5 | 10.0 | 1000 | 0.000 |
| 3 | Histidine | 6.5 | 10.0 | 200 | 0.010 |
| 4 | Histidine | 6.5 | 30.0 | 600 | 0.000 |
| 5 | Histidine | 6.5 | 10.0 | 600 | 0.005 |
| 6 | Histidine | 6.5 | 30.0 | 200 | 0.005 |
| 7 | Histidine | 6.5 | 22.9 | 460 | 0.003 |
| 8 | Histidine | 6.5 | 16.0 | 760 | 0.002 |
| 9 | Histidine | 6.5 | 10.0 | 440 | 0.007 |

For lyophilization, IMC-A12 was buffer exchanged into either neat 10 mM Histidine at pH 6.5, or 10 mM Citrate at pH 6.5 using Lab scale TFF and Pellicon® XL filter, 50K cut-off filter (Millipore, Corporation). Lyo and Cryo protectants were added from concentrated stock, after buffer exchange was done. Protein, concentration was determined by absorbance at 280 nm using an extinction coefficient of 1.50. TWEEN 80 was added from a 10% (w/v, in DI water) stock solution after protein concentration adjustments. All samples were filtered through 0.22 μm cutoff (Durapose PVDF membrane) syringe filter.

The buffer type, cryo- and lyo protectants and bulking agents were screened for effect on monomer, aggregate, degradant and turbidity of 20 mg/mL IMC-A12 in the formulations shown in Table 41. The lyophilized drug product was incubated at 40° C. and 50° C. for 3 months. Following incubation, lyophilized drug products were reconstituted into miliQ water to 5 mg/mL. Reconstituted products were analyzed by SEC-HPLC and Turbidity. The results were fitted using statistical software JMP. Results are summarized below.

Effects of Variables on Predicted Monomer, Aggregate, Degradant and Turbidity

The reconstituted drug products were analyzed by SEC-HPLC and turbidity analysis. The variation of percent monomer, aggregate, degradant and turbidity as a function of buffer type, cryo-and-lyo protectants, and bulking agents was observed. The results demonstrated that (1) Histidine buffer causes greater monomer and lesser aggregate than Citrate buffer. (2) Trehalose and Sucrose increase the monomer content and lower the aggregation. (3) The bulking agents, mannitol and glycine did not have significant effects of the percent monomer or aggregate. None of the tested variables has significant effect on degradant.

Confirmation of Predicted Results by One-Factor-at-a-Time Approach

In order to confirm statistical predicted results, the formulations 5, 6, 9 and 10 in Table 41 were analyzed using one-factor-at-a-time approach. The effect of incubation at 40° C. and 50° C. for up to 3 months on the percent monomer, aggregate, degradant and turbidity, was observed. Results confirmed that (1) histidine is a superior buffer than citrate and (2) thehalose is a better stabilizer than sucrose.

Summary of Buffer Type, Cryo- and Lyo-Protectant, and Bulking Agent Screening

Freeze-dried IMC-A12 formulations have greater stability in histidine buffer than citrate buffer. Trehalose has better stabilizing effect than sucrose. The presence of the bulking agents, mannitol and glycine, did not significantly effect stability.

Optimization for IMC-A12, Trehalose and TWEEN 80 Concentration for Optimal Freeze-Dried Formulation The mixture design model was used to optimize the IMC-A12 concentration, ratio of thehalose:IMC-A12, and concentration of TWEEN 80 for optimal formulation. The experiment design matrix is shown in Table 42. The lyophilized IMC-A12 was incubated at 4° C., 40° C. and 50° C. for up to 4 months. Results are discussed below.

Variation of Percent Monomer as a Function of Formulation

Lyophilized IMC-A12 formulations from Table 42 were incubated at 4° C., 40° C. and 50° C. for up to 4 months. The lyophilized samples were reconstituted with MiliQ water to 5 mg/mL. The reconstituted samples were analyzed by SEC-HPLC to determine the remaining monomer percent.

Effect of IMC-A12 Concentration, Ratio of Trehalose:A12 and TWEEN 80 Concentration on Rate of Monomer Change The rate of monomer change was defined as a slope of monomer variation as a function of time. The Excel software was used to calculate the slope. The rate of monomer change was smallest at lowest IMC-A12 concentration and at highest trehalose to IMC-A12 ratio. TWEEN 80 did not have significant effect.

Summary of Optimization Study

Predicted monomer content increased with decrease of IMC-A12 concentration and increase of Trehalose to IMC-A12 ratio. At fixed IMC-A12 concentration, monomer content increased by increasing trehalose to IMC-A12 ratio TWEEN 80 had minimal effect on percent monomer. Formulation 4 that has 30 mg/mL IMC-A12 and trehalose to IMC-A12 ratio of 600 was selected as a preferred formulation.

Characterization of Freeze-Dried IMC-A12

The moisture content of the lyophilized product as determined by Karl-Fisher analysis was found to be .about. 1.0%. The freeze-dried IMC-A12 was reconstituted to 5 mg/mL with miliQ water. Reconstitution time was about 1-2 min.

Effect of Lyophilization on IMC-A12 Stability

To ensure that the lyophilization process had not changed the IMC-A12 stability, the IMC-A12 was analyzed by SEC-HPLC before and after lyophilization. Lyophilized IMC-A12 was reconstituted prior to SEC-HPLC analysis. The percent monomer, aggregate and degradant for pre and post lyophilized A 12 are shown in Table 43.

TABLE 43

SEC-HPLC Analysis of Pre and Post Lyophilized IMC-A12

| | Monomer (%) | Aggregate (%) | Degradent (%) |
|---|---|---|---|
| Before Lyophilization | 95.7 | 3.0 | 1.4 |
| After Lyophilization | 95.6 | 3.1 | 1.5 |

Effect of Lyophilization on Conformational Stability of IMC-A12

To ensure that the lyophilization process has not altered the secondary structure of A12, secondary structure of pre and post lyophilized IMC-A12 was examined by circular dichorism. The CD spectrums were collected using a Jasco 810 circular dichorism spectrophotometer, the IMC-A12 concentration was 0.1 mg/mL. Secondary structure of IMC-A12 was not altered because of lyophilization.

Effect of Lyophilization on Particulate Counts for IMC-A12

The effect of lyophilization on particulate content for IMC-A12 was measured using HIAC ROYCO MODEL 9703 Liquid Particle System. IMC-A12 before and after lyophilization was diluted/reconstituted to 5 mg/mL. Results are shown in Table 44. The particulate counts did not changed significantly.

TABLE 44

HIAC Analysis of Pre and Post Lyophilized IMC-A12

| | =10 μm/mL | =25 μm/mL | =50 μm/mL |
|---|---|---|---|
| Before Lyophilization | 26.33 | 1.67 | 0.00 |
| After Lyophilization | 38.67 | 0.33 | 0.00 |

Comparison Between Solution and Lyophilized IMC-A12 Formulations

The following formulations were compared:
(1) PBS Solution formulation, 5 mg/mL IMC-A12 in PBS
(2) Citrate Solution formulation, 5 mg/mL IMC-A12 in 10 mM Sodium citrate, 100 mM NaCl, 100 mM Glycine, 0.01% TWEEN 80 (w/v), pH 6.5
(3) Lyophilized formulation, 30 mg/mL IMC-A12, 10 mM L-Histidine, 4.6% Trehalose, pH 6.5

Real-Time Accelerated Temperature Stability

The PBS and Citrate solution formulations, and the lyophilized formulation were incubated at 4° C., 40° C., 50° C. The lyophilized IMC-A12 was reconstituted to 5 mg/mL with milli-Q water prior to analysis. The solution and reconstituted lyophilized formulations were analyzed by SEC-HPLC and SDS-PAGE.

IMC-A12 solution formulations in PBS and citrate buffer, and IMC-A12 in the preferred lyophilized formulation were incubated at 40° C. and 50° C. for 4 months. The lyophilized samples were reconstituted in Milli-Q water and percent monomer was analyzed by SEC-HPLC.

SDS-page (reduced) analysis of the samples after incubation at 4° C., 40° C. and 50° C. for 4 months was observed. IMC-A12 solution formulations in PBS and citrate buffer, and IMC-A12 in the preferred lyophilized formulation were incubated at 4° C., 40° C. and 50° C. for 4 months. The lyophilized samples were reconstituted in Milli-Q water and 10 us were loaded into a 4-20% Tris-glycine gel. The gel was stained with Coomassie blue.

Photo-Stability of Lyophilized Formulation

Photo stability was performed as described above. The lyophilized IMC-A12 and solution formulations PBS and Citrate were exposed to light at room temperature. The total light exposure was 200 Watt hours/m2 near UV+1.2 million lux hours fluorescent. Controlled samples were wrapped with black paper to block light. Control and test samples were placed inside the photo stability chamber (Caron 6500 series, Caron, Marietta, Ohio). Following light exposure, both controls and test samples were analyzed by SEC-HPLC. Percent monomer, aggregate and degradant for controls and light exposed samples are given in Table 45. IMC-A12 was found to be light sensitive in both the formulation; however, the photo stability was significantly better in the citrate formulation than the PBS formulation.

TABLE 45

Photo-stability for IMC-A12 in lyophilized and solutions formulations

| Formulation | Monomer (%) | Aggregates (%) | Degradents (%) |
|---|---|---|---|
| PBS-Control | 96.6 | 1.5 | 2.0 |
| PBS-Light Exposed | 73.5 | 22.8 | 3.7 |

TABLE 45-continued

Photo-stability for IMC-A12 in lyophilized and solutions formulations

| Formulation | Monomer (%) | Aggregates (%) | Degradents (%) |
|---|---|---|---|
| Citrate-Control | 95.7 | 1.4 | 2.9 |
| Citrate-Light Exposed | 81.9 | 14.2 | 3.9 |
| Lyophilized-Control | 98.1 | 1.0 | 0.9 |
| Lyophilized-Light Exposed | 94.0 | 4.6 | 1.4 |

Comparison of Containers of the Present Disclosure with Conventional Containers

The above examples will be carried out using active pharmaceutical ingredient contained in conventional glass containers in addition to using active pharmaceutical ingredient contained in containers of the present disclosure. The results will be compared between the different vessels used to store the active pharmaceutical ingredient It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A pharmaceutical product comprising:
FORTEO ([rhPTH(1-34]), DULAGLUTIDE (LY2189265), recombinant human insulin glargine, RAMUCIRUMAB (IMC-1121B), SOLANEZUMAB (LY2062430), IXEKUZUMAB (LY2439821), TABALUMAB (LY2127399), NECITUMUMAB (IMC-11F8), or CIXUTUMUMAB (IMC-A12) and a pharmaceutically acceptable excipient;
contained within a glass pharmaceutical container comprising a glass composition comprising:
$SiO_2$ in an amount greater than or equal to about 72 mol. % and less than or equal to about 78 mol. %;
alkaline earth oxide comprising both MgO and CaO, wherein CaO is present in an amount up to about 1.0 mol. %, and a ratio (CaO (mol. %)/(CaO (mol. %)+MgO (mol. %))) is less than or equal to 0.5;
X mol. % $Al_2O_3$, wherein X is greater than or equal to about 5 mol. % and less than or equal to about 7 mol. %;
Y mol. % alkali oxide, wherein the alkali oxide comprises $Na_2O$ in an amount greater than about 8 mol. %; and
a ratio of a concentration of $B_2O_3$ (mol. %) in the glass container to (Y mol. %–X mol. %) is less than or equal to 0.3, wherein the delamination resistant pharmaceutical container comprises an active pharmaceutical ingredient.

2. The pharmaceutical product of claim 1, wherein the pharmaceutical container comprises a compressive stress greater than or equal to 150 MPa.

3. The pharmaceutical product of claim 1, wherein the pharmaceutical container comprises a compressive stress greater than or equal to 250 MPa.

4. The pharmaceutical product of claim 1, wherein the pharmaceutical container comprises a depth of layer greater than 30 μm.

5. The pharmaceutical product of claim 1, wherein the pharmaceutical product has increased stability, product integrity, or efficacy.

6. The pharmaceutical product of claim 1:
wherein the glass pharmaceutical container has a compressive stress greater than 150 MPa and a depth of layer greater than 10 μm, and wherein the pharmaceutical eetiipositieft product comprises increased stability, product integrity, or efficacy.

7. The pharmaceutical product of claim 1:
wherein the glass pharmaceutical container is substantially free of boron, and wherein the pharmaceutical product comprises increased stability, product integrity, or efficacy.

8. The pharmaceutical product of claim 7, wherein the glass pharmaceutical container comprises a compressive stress layer with a surface compressive stress greater than 150 MPa and a depth of layer greater than 25 μm.

9. The pharmaceutical product of claim 8, wherein the glass pharmaceutical container comprises a compressive stress layer with a surface compressive stress greater than 300 MPa and a depth of layer greater than 35 μm.

10. The pharmaceutical product of claim 7, wherein said glass pharmaceutical container comprises a substantially homogeneous inner layer.

11. The pharmaceutical product of claim 10, wherein said glass pharmaceutical container comprises a compressive stress layer with a surface compressive stress greater than 150 MPa and a depth of layer greater than 25 μm.

12. The pharmaceutical product of claim 1, wherein the pharmaceutical container comprises an internal homogeneous layer.

* * * * *

UNITED STATES PATENT AND TRADEMARK OFFICE
CERTIFICATE OF CORRECTION

Page 1 of 1

PATENT NO. : 9,700,485 B2
APPLICATION NO. : 14/259259
DATED : July 11, 2017
INVENTOR(S) : Wendell P. Weeks et al.

It is certified that error appears in the above-identified patent and that said Letters Patent is hereby corrected as shown below:

On the Title Page

On page 4, in Column 2, item (56), Other Publications, Line 42, delete "Editro:" and insert -- Editor: --, therefor.

In the Claims

In Column 99, Line 3, Claim 1, delete "([rhPTH(1-34])," and insert -- ([rhPTH(1-34)]), --, therefor.

In Column 100, Line 4, Claim 6, delete "claim 1:" and insert -- claim 1, --, therefor.

In Column 100, Line 8, Claim 6, delete "eetiipositieft product" and insert -- product --, therefor.

In Column 100, Line 10, Claim 7, delete "claim 1:" and insert -- claim 1, --, therefor.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*